United States Patent
Gelman et al.

(10) Patent No.: US 11,021,468 B2
(45) Date of Patent: Jun. 1, 2021

(54) TGF-ß INHIBITORS

(71) Applicant: Rigel Pharmaceuticals, Inc., South San Francisco, CA (US)

(72) Inventors: Marina Gelman, San Francisco, CA (US); Pingyu Ding, Foster City, CA (US); Todd Kinsella, Redwood City, CA (US); Rajinder Singh, Belmont, CA (US); Somasekhar Bhamidipati, Foster City, CA (US); Jeffrey Clough, Redwood City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/563,056

(22) PCT Filed: Mar. 29, 2016

(86) PCT No.: PCT/US2016/024755
§ 371 (c)(1),
(2) Date: Sep. 29, 2017

(87) PCT Pub. No.: WO2016/160833
PCT Pub. Date: Oct. 6, 2016

(65) Prior Publication Data
US 2018/0339979 A1    Nov. 29, 2018

Related U.S. Application Data

(60) Provisional application No. 62/141,441, filed on Apr. 1, 2015.

(51) Int. Cl.
| | | |
|---|---|---|
| A61P 35/02 | (2006.01) | |
| C07D 401/12 | (2006.01) | |
| C07D 403/12 | (2006.01) | |
| C07D 471/04 | (2006.01) | |

(52) U.S. Cl.
CPC .......... C07D 403/12 (2013.01); A61P 35/02 (2018.01); C07D 401/12 (2013.01); C07D 471/04 (2013.01)

(58) Field of Classification Search
CPC ... C07D 403/12; C07D 471/04; C07D 401/12
See application file for complete search history.

(56) References Cited

FOREIGN PATENT DOCUMENTS

| | | | | |
|---|---|---|---|---|
| CN | 103896856 A | * | 7/2014 | |
| WO | WO 00/12497 | | 3/2000 | |
| WO | WO 02/076976 | | 10/2002 | |
| WO | WO-03030909 A1 | * | 4/2003 | ........... C07D 401/14 |
| WO | WO 03/097615 | | 11/2003 | |
| WO | WO 2005/065691 | | 7/2005 | |
| WO | WO 2008/054599 | | 5/2008 | |
| WO | WO 2010/104851 | | 9/2010 | |
| WO | WO -2010104851 A1 | * | 9/2010 | ........... C07D 239/72 |
| WO | PCT/US2013/063755 A2 | | 4/2014 | |
| WO | WO-2014055996 A2 | * | 4/2014 | ........... A61K 31/506 |
| WO | PCT/US2015/025176 A1 | | 10/2015 | |

OTHER PUBLICATIONS

Chemical Abstract Service STN Database Registry No. 1638277-48-1 [Entered STN: Dec. 9, 2014]. (Year: 2014).*
Chemical Abstract Service STN Database Registry No. 1350644-83-5 [Entered STN: Dec. 12, 2011]. (Year: 2011).*
Long et al. "Preparation of multi-substituted pyrimidine compounds as JNK kinase inhibitors." CN 103896856 A (pub. Jul. 2, 2014). English machine translation downloaded from Dialog.com [downloaded on Jan. 21, 2021]. (Year: 2014).*
Partridge et al., "Cyclic Amidines, Part XVIII, The Synthesis of Tricycloquinazolines by Cyclodehydrogenation," Journal of the Chemical Society, Chemical Society, Letchworth; GB, Jan. 1, 1964, 2 pages.
International Search Report and Written Opinion dated May 31, 2016 for International Application No. PCT/US2016/024755 filed Mar. 29, 2016, 15 pages.

* cited by examiner

*Primary Examiner* — Amanda L. Aguirre
(74) *Attorney, Agent, or Firm* — Klarquist Sparkman, LLP

(57) ABSTRACT

Disclosed are aryl pyrimidine compounds, as well as pharmaceutical compositions and methods of use thereof. One embodiment is a compound having the structure (I) and pharmaceutically acceptable salts, prodrugs and N-oxides thereof (and solvates and hydrates thereof), wherein A, Z, R and R' are as described herein. In certain embodiments, a compound disclosed herein inhibits the activity of one or more members of the TGF-β superfamily, and can be used to treat disease by blocking such activity.

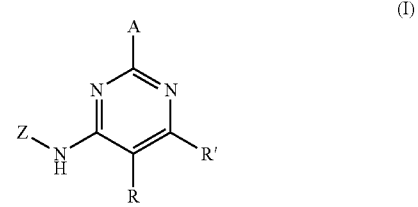

(I)

8 Claims, No Drawings

TGF-β INHIBITORS

This application is a U.S. national phase application under 35 U.S.C. 371 of International Patent Application no. PCT/US2016/024755 filed Mar. 29, 2016, which claims the benefit of U.S. Provisional Patent Application No. 62/141,441 filed Apr. 1, 2015.

BACKGROUND OF DISCLOSURE

Field of Invention

This invention relates to the field of compounds, pharmaceutical compositions comprising them, and methods of using the compounds and compositions. This invention relates more particularly to the field of aryl pyrimidine compounds and pharmaceutical compositions thereof, methods of inhibiting TGF-β receptor signaling with the compounds, and methods of treating and/or preventing disease with the compounds.

Technical Background

Growth and Differentiation Factor-8 (GDF-8), also known as myostatin, and TGF-β1 are members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim. Sci., 38: 752-757; McPherron and Lee (1997) Proc. Natl. Acad. Sci. USA, 94: 12457-12461; and Kambadur et al. (1997) Genome Res., 7: 910-915). Because GDF-8 is expressed in both developing and adult muscles, it is not clear whether it regulates muscle mass during development or in adults. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

There are also a number of conditions associated with a loss of bone, including osteoporosis, especially in the elderly and/or postmenopausal women. Currently available therapies for these conditions work by inhibiting bone resorption.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

U.S. Pat. No. 7,320,789 shows that GDF-8 antibodies in mouse models can increase muscle strength (e.g., for treating sarcopenia), increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

SUMMARY

We recognized that new therapeutic agents that inhibit the activity of one or more members of the TGF-β superfamily are useful for treating human or animal disorders in which TGF-β signaling is implicated. In one aspect, such disorders include those in which immunomodulation, regulation of fibrosis and/or an increase in muscle tissue would be therapeutically beneficial, particularly oncology, fibrotic diseases, muscle and adipose tissue disorders, bone degenerative diseases, neuromuscular disorders, and diabetes.

Accordingly, the present invention comprises compounds, pharmaceutical compositions comprising them, and methods of using them to inhibit TGF-β superfamily activity both in vitro and in vivo and to treat and/or prevent disease by inhibiting TGF-β superfamily activity.

Disclosed herein are compounds having structural formula (I):

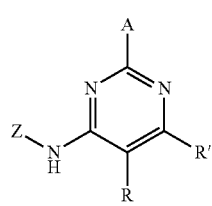

(I)

and pharmaceutically acceptable salts, prodrugs, and N-oxides thereof (and solvates and hydrates thereof), wherein A, Z, R and R' are as described herein.

Also disclosed herein are pharmaceutical compositions. Examples of such compositions include those having at least one pharmaceutically acceptable carrier, diluent, and/or excipient together with a compound, pharmaceutically acceptable salt, prodrug, or N-oxide (or solvate or hydrate) as described herein.

Another aspect of the present invention comprises methods for treating and/or preventing disease by blocking GDF 8, TGF-β, Activin, Nodal or combinations thereof. Accordingly, the invention also comprises methods for treating disease using the presently disclosed compounds and pharmaceutical compositions.

Another aspect of the invention is the use of the compounds described herein to block TGF-β superfamily activity in vitro and in vivo for the purpose of studying their role in biological processes.

All publications referenced herein are incorporated by reference in their entirety to the extent they are not inconsistent with the teachings presented herein.

DETAILED DESCRIPTION

In one aspect, the invention comprises compounds that inhibit TGF-β.

In embodiment $I_1$ of this first aspect, the compounds have structural formula (I):

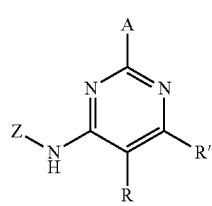

(I)

or a pharmaceutically acceptable salt, prodrug, or N-oxide thereof, or a solvate or hydrate thereof, wherein
A is phenyl optionally substituted with one to five $R^1$ groups, wherein each $R^1$ is independently halogen, cyano, —$OR^a$, —$SR^a$, —$N(R^a)_2$, $C_{1-6}$ alkyl, $C_{1-6}$haloalkyl or $C_{3-8}$cycloalkyl,
wherein each $R^a$ is independently hydrogen, $C_{1-6}$ alkyl or $C_{1-6}$ haloalkyl;
Z is
a fused bicyclic ring of the formula,

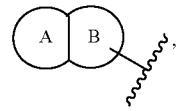

wherein
ring A is phenyl or pyrazole,
optionally substituted with one to four $R^2$ groups, wherein each $R^2$ is independently halogen, $C_{1-6}$ alkyl, $C_{1-6}$ haloalkyl, —$OR^b$, —$C(O)NR^b_2$, —$C(O)CH_2NR^b_2$, —$CH_2$—$OP(O)(OR)_2$, or heteroaryl,
wherein each $R^b$ is independently hydrogen, $C_{1-6}$ alkyl or $C_{1-6}$, and
wherein each $R^c$ is independently hydrogen or $C_{1-6}$ alkyl; ring B is phenyl or pyridyl, each optionally substituted with one to three $R^3$ groups, wherein each $R^3$ is independently halogen, $C_{1-6}$alkyl, $C_{1-6}$haloalkyl, cycloalkyl or heteroaryl;
R and R' are independently hydrogen, halogen, $C_{1-6}$alkyl or $C_{1-6}$ haloalkyl;
or R and R' taken together with the carbon atoms to which they are attached form a pyrrole or phenyl; and
wherein each alkyl, haloalkyl cycloalkyl or heteroaryl group is optionally substituted with one or two —$R^z$ groups that are each independently halogen, $C_{1-6}$alkyl or $C_{1-6}$haloalkyl.

In embodiment $I_2$, the compounds are of embodiment $I_1$, wherein
A is phenyl optionally substituted with one to five $R^1$ groups, wherein each $R^1$ is independently halogen, cyano, —$OR^a$, —$SR^a$, —$N(R^a)_2$, $C_{1-6}$ alkyl or $C_{1-6}$haloalkyl, wherein each $R^a$ is independently hydrogen, $C_{1-6}$ alkyl or $C_{1-6}$ haloalkyl;
Z is
a fused bicyclic ring of the formula,

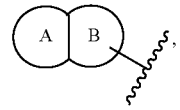

wherein
ring A is phenyl or pyrazole,
optionally substituted with one to four $R^2$ groups, wherein each $R^2$ is independently halogen, $C_{1-6}$alkyl, $C_{1-6}$haloalkyl, —$OR^b$, —$C(O)NR^b_2$, —$C(O)CH_2NR^b_2$ or —$CH_2$—$OP(O)(OR^c)_2$,
wherein each $R^b$ is independently hydrogen, $C_{1-6}$ alkyl or $C_{1-6}$, and
wherein each $R^c$ is independently hydrogen or $C_{1-6}$ alkyl;

ring B is phenyl or pyridyl, each optionally substituted with one to three $R^3$ groups, wherein each $R^3$ is independently halogen, $C_{1-6}$alkyl or $C_{1-6}$haloalkyl.

In embodiment $I_3$, the compounds are of any one of embodiments $I_1$ or $I_2$, wherein R' is hydrogen.

In embodiment $I_4$, the compounds are of any one of embodiments $I_1$-$I_3$, wherein ring A is phenyl; and ring B is phenyl.

In embodiment $I_5$, the compounds are of any one of embodiments $I_1$-$I_3$, wherein ring A is phenyl; and ring B is pyridyl.

In embodiment $I_6$, the compounds are of any one of embodiments $I_1$-$I_3$, wherein ring A is pyrazole; and ring B is phenyl.

In embodiment $I_7$, the compounds are of any one of embodiments $I_1$-$I_3$, wherein ring A is pyrazole; and ring B is pyridyl.

In embodiment $I_8$, the compounds are of any one of embodiments $I_1$-$I_7$, wherein wherein each alkyl, haloalkyl cycloalkyl and heteroaryl group is unsubstituted.

The invention further comprises subgenera of formula (I) in which from one to all of structural formula (I), A, Z, R and R' are independently selected from the groups (Ia) et seq., (1a) et seq., (2a) et seq., and (3a) et seq. defined hereinbelow (e.g., wherein the compound is of structural formula (I) as defined in any of the above embodiments and A is phenyl optionally substituted with one $R^1$ group, wherein $R^1$ is halogen; or the compound is formula (Ib), A is group (1c), Z is group (2b), and R/R' is group (3i)):

Formula (I) is One of Structural Formulae (Ia)-(Io):

(Ia)

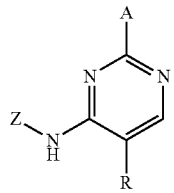

(Ib)

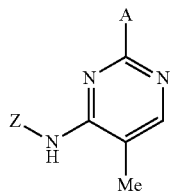

(Ic)

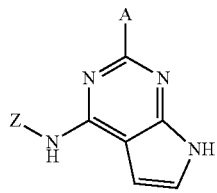

(Id)

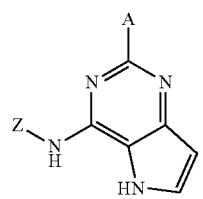

(Ie)

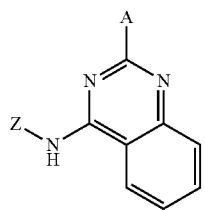

(If)

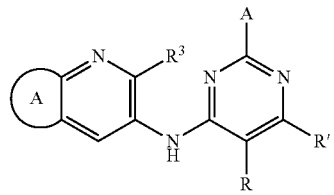

(Ig)

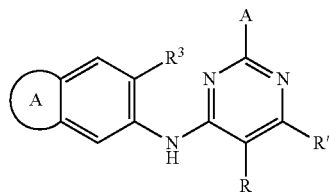

(Ih)

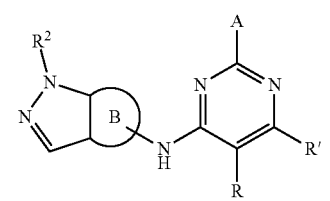

(Ii)

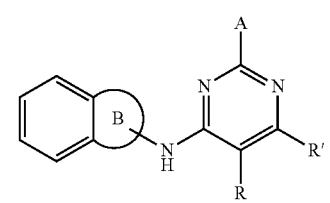

(Ij)

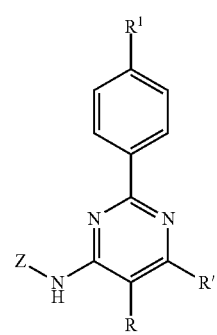

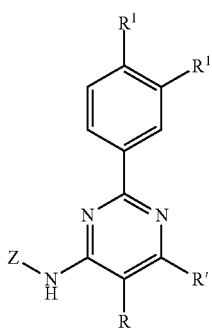

(Ik)

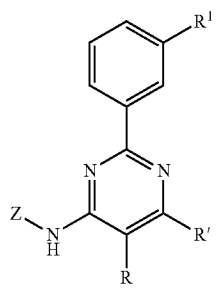

(Il)

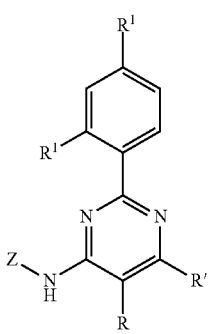

(Im)

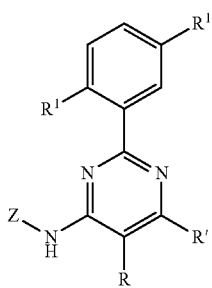

(In)

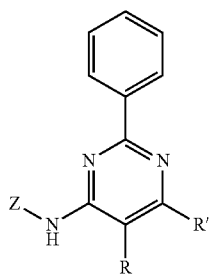

(Io)

A is Selected from One of the Following Groups (1a)-(1mm):

(1a) A is phenyl optionally substituted with one to five $R^1$ groups, wherein each $R^1$ is independently halogen, cyano, —$OR^a$, —$SR^a$, —$N(R^a)_2$, $C_{1-6}$ alkyl, $C_{1-6}$haloalkyl or $C_{3-8}$cycloalkyl,
wherein each $R^a$ is independently hydrogen, $C_{1-6}$ alkyl or $C_{1-6}$ haloalkyl.

(1b) A is phenyl optionally substituted with one to five $R^1$ groups, wherein each $R^1$ is independently halogen, cyano, —$OR^a$, —$SR^a$, —$N(R^a)_2$, $C_{1-6}$ alkyl or $C_{1-6}$haloalkyl,
wherein each $R^a$ is independently hydrogen, $C_{1-6}$ alkyl or $C_{1-6}$ haloalkyl.

(1c) A is phenyl substituted with one to five $R^1$ groups, wherein each $R^1$ is independently halogen, cyano, —$OR^a$, —$SR^a$, —$N(R^a)_2$, $C_{1-6}$ alkyl, $C_{1-6}$haloalkyl or $C_{3-8}$cycloalkyl,
wherein each $R^a$ is independently hydrogen, $C_{1-6}$ alkyl or $C_{1-6}$ haloalkyl.

(1d) A is phenyl substituted with one to five $R^1$ groups, wherein each $R^1$ is independently halogen, cyano, —$OR^a$, —$SR^a$, —$N(R^a)_2$, $C_{1-6}$ alkyl or $C_{1-6}$haloalkyl,
wherein each $R^a$ is independently hydrogen, $C_{1-6}$ alkyl or $C_{1-6}$ haloalkyl.

(1e) Any of groups of (1a)-(1d), wherein each $R^1$ is independently halogen, cyano, —$OR^a$, —$SR^a$, —$N(R^a)_2$, $C_{1-6}$ alkyl or $C_{1-6}$haloalkyl.

(1f) Any of groups of (1a)-(1d), wherein each $R^1$ is independently halogen, cyano, —$OR^a$, —$N(R^a)_2$, $C_{1-6}$ alkyl or $C_{1-6}$haloalkyl.

(1g) Any of groups of (1a)-(1d), wherein each $R^1$ is independently halogen, cyano, —$OR^a$, $C_{1-6}$ alkyl or $C_{1-6}$haloalkyl.

(1h) Any of groups of (1a)-(1d), wherein each $R^1$ is independently halogen, cyano, $C_{1-6}$ alkyl or $C_{1-6}$haloalkyl.

(1i) Any of groups of (1a)-(1d), wherein each $R^1$ is independently halogen or cyano.

(1j) Any of groups of (1a)-(1d), wherein each $R^1$ is halogen or cyano.

(1k) Any of groups of (1a)-(1d), wherein each $R^1$ is cyano.

(1l) Any of groups of (1a)-(1d), wherein each $R^1$ is independently halogen, cyano, —$OR^a$, —$SR^a$, —$N(R^a)_2$ or $C_{1-6}$ alkyl.

(1m) Any of groups of (1a)-(1d), wherein each $R^1$ is independently halogen, cyano, —$OR^a$, or $C_{1-6}$ alkyl.

(1n) Any of groups of (1a)-(1d), wherein each $R^1$ is independently halogen or $C_{1-6}$ alkyl.

(1o) Any of groups of (1a)-(1d), wherein each $R^1$ is independently halogen, —$OR^a$, —$SR^a$, —$N(R^a)_2$, $C_{1-6}$ alkyl or $C_{1-6}$haloalkyl.

(1p) Any of groups of (1a)-(1d), wherein each $R^1$ is independently cyano, —$OR^a$, —$SR^a$, —$N(R^a)_2$, $C_{1-6}$ alkyl or $C_{1-6}$haloalkyl.

(1q) Any of groups of (1a)-(1d), wherein each $R^1$ is independently —$OR^a$, —$SR^a$, —$N(R^a)_2$, $C_{1-6}$ alkyl or $C_{1-6}$haloalkyl.

(1r) Any of groups of (1a)-(1d), wherein each $R^1$ is independently —$OR^a$, —$N(R^a)_2$ or $C_{1-6}$ alkyl.

(1s) Any of groups of (1a)-(1d), wherein each $R^1$ is independently —$OR^a$ or $C_{1-6}$ alkyl (1t) Any of groups of (1a)-(1d), wherein each $R^1$ is independently —$OR^a$, —$N(R^a)_2$, $C_{1-6}$ alkyl or $C_{1-6}$haloalkyl.

(1u) Any of groups of (1a)-(1d), wherein each $R^1$ is independently halogen, $C_{1-6}$ alkyl or $C_{1-6}$haloalkyl.

(1v) Any of groups of (1a)-(1d), wherein each $R^1$ is independently halogen or $C_{1-6}$ alkyl.
(1w) Any of groups of (1a)-(1d), wherein each $R^1$ is independently halogen or $C_{1-6}$haloalkyl.
(1x) Any of groups of (1a)-(1d), wherein each $R^1$ is halogen.
(1y) Any of groups of (1a)-(1d), wherein each $R^1$ is $C_{1-6}$ alkyl.
(1z) Any of groups of (1a)-(1d), wherein each $R^1$ is independently —$OR^a$ or —$C_{1-6}$ alkyl.
(1aa) Any of groups of (1a)-(1d), wherein each $R^1$ is independently —$OR^a$, —$N(R^a)_2$.
(1bb) Any of groups of (1a)-(1d), wherein each $R^1$ is independently —$OR^a$.
(1cc) Any of groups of (1a)-(1d), wherein each $R^1$ is independently —$N(R^a)_2$.
(1dd) Any of groups of (1a)-(1cc), wherein each $R^a$ is independently hydrogen, $C_{1-6}$ alkyl or $C_{1-6}$ haloalkyl.
(1ee) Any of groups of (1a)-(1cc), wherein each $R^a$ is independently hydrogen or $C_{1-6}$ alkyl.
(1ff) Any of groups of (1a)-(1cc), wherein each $R^a$ is hydrogen.
(1gg) Any of groups of (1a)-(1cc), wherein each $R^a$ is $C_{1-6}$ alkyl.
(1hh) Any of groups of (1a)-(1cc), wherein each $R^a$ is independently hydrogen or methyl.
(1ii) The group of (1a)-(1hh), wherein A is phenyl substituted with one to four $R^1$ groups.
(1jj) The group of (1a)-(1hh), wherein A is phenyl substituted with one to three $R^1$ groups.
(1kk) The group of (1a)-(1hh), wherein A is phenyl substituted with one or two $R^1$ groups.
(1ll) The group of (1a)-(1hh), wherein A is phenyl substituted with one $R^1$ group.
(1 mm) A is unsubstituted phenyl.

Z is Selected from One of the Following Groups (2a)-(2oo):

(2a) Z is
a fused bicyclic ring of the formula,

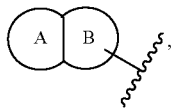

wherein
ring A is phenyl or pyrazole,
optionally substituted with one to four $R^2$ groups,
wherein each $R^2$ is independently halogen, $C_{1-6}$alkyl, $C_{1-6}$haloalkyl, —$OR^b$, —$C(O)NR^b_2$, —$C(O)CH_2NR^b_2$, —$CH_2$—$OP(O)(OR)_2$, or heteroaryl,
wherein each $R^b$ is independently hydrogen, $C_{1-6}$ alkyl or $C_{1-6}$ haloalkyl, and
wherein each $R^c$ is independently hydrogen or $C_{1-6}$ alkyl;
ring B is phenyl or pyridyl,
optionally substituted with one to three $R^3$ groups, wherein each $R^3$ is independently halogen, $C_{1-6}$alkyl, $C_{1-6}$haloalkyl, cycloalkyl or heteroaryl.

(2b) Z is
a fused bicyclic ring of the formula,

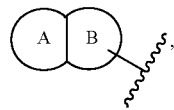

wherein
ring A is phenyl or pyrazole,
optionally substituted with one to four $R^2$ groups,
wherein each $R^2$ is independently halogen, $C_{1-6}$alkyl, $C_{1-6}$haloalkyl, —$OR^b$, —$C(O)NR^b_2$, —$C(O)CH_2NR^b_2$ or —$CH_2$—$OP(O)(OR^c)_2$,
wherein each $R^b$ is independently hydrogen, $C_{1-6}$ alkyl or $C_{1-6}$ haloalkyl, and
wherein each $R^c$ is independently hydrogen or $C_{1-6}$ alkyl;
ring B is phenyl or pyridyl,
optionally substituted with one to three $R^3$ groups, wherein each $R^3$ is independently halogen, $C_{1-6}$alkyl or $C_{1-6}$haloalkyl.
(2c) Any of groups of (2a)-(2b), wherein
ring A is phenyl; and
ring B is phenyl or pyridyl.
(2d) Any of groups of (2a)-(2b), wherein
ring A is pyrazole; and
ring B is phenyl or pyridyl.
(2e) Any of groups of (2a)-(2b), wherein
ring A is phenyl or pyrazole; and
ring B is phenyl.
(2f) Any of groups of (2a)-(2b), wherein
ring A is phenyl or pyrazole; and
ring B is pyridyl.
(2g) Any of groups of (2a)-(2b), wherein
ring A is phenyl; and
ring B is phenyl.
(2h) Any of groups of (2a)-(2b), wherein
ring A is phenyl; and
ring B is pyridyl.
(2i) Any of groups of (2a)-(2b), wherein
ring A is pyrazole; and
ring B is phenyl.
(2j) Any of groups of (2a)-(2b), wherein
ring A is pyrazole; and
ring B is pyridyl.
(2k) Any of groups of (2a)-(2j), wherein
each $R^2$ is independently halogen, $C_{1-6}$alkyl, $C_{1-6}$haloalkyl, —$OR^b$, —$C(O)NR^b_2$, —$C(O)CH_2NR^b_2$, —$CH_2$—$OP(O)(OR)_2$, or heteroaryl.
(2l) Any of groups of (2a)-(2j), wherein
each $R^2$ is independently halogen, $C_{1-6}$alkyl, —$OR^b$, —$C(O)NR^b_2$, —$C(O)CH_2NR^b_2$ or —$CH_2$—$OP(O)(OR)_2$.
(2m) Any of groups of (2a)-(2j), wherein
each $R^2$ is independently halogen, $C_{1-6}$alkyl, —$OR^b$, —$C(O)NR^b_2$, —$C(O)CH_2NR^b_2$ or —$CH_2$—$OP(O)(OR)_2$.
(2n) Any of groups of (2a)-(2j), wherein
each $R^2$ is independently $C_{1-6}$alkyl, —$C(O)NR^b_2$ or —$C(O)CH_2NR^b_2$.
(2o) Any of groups of (2a)-(2j), wherein
each $R^2$ is independently $C_{1-6}$alkyl, —$C(O)NR^b_2$ or —$C(O)CH_2NR^b_2$.

(2p) Any of groups of (2a)-(2j), wherein
each $R^2$ is $C_{1-6}$alkyl.
(2q) Any of groups of (2a)-(2j), wherein
each $R^2$ is —C(O)$NR^b{}_2$.
(2r) Any of groups of (2a)-(2j), wherein
each $R^2$ is —C(O)$CH_2NR^b{}_2$.
(2s) Any of groups of (2a)-(2r), wherein
each $R^3$ is independently halogen, $C_{1-6}$alkyl, $C_{1-6}$haloalkyl, cycloalkyl or heteroaryl.
(2t) Any of groups of (2a)-(2r), wherein
each $R^3$ is independently halogen, $C_{1-6}$alkyl, $C_{1-6}$haloalkyl or cycloalkyl.
(2u) Any of groups of (2a)-(2r), wherein
each $R^3$ is independently halogen, $C_{1-6}$alkyl, $C_{1-6}$haloalkyl or heteroaryl.
(2v) Any of groups of (2a)-(2r), wherein
each $R^3$ is independently halogen, $C_{1-6}$alkyl or $C_{1-6}$haloalkyl.
(2w) Any of groups of (2a)-(2r), wherein
each $R^3$ is independently halogen or $C_{1-6}$haloalkyl.
(2x) Any of groups of (2a)-(2r), wherein
each $R^3$ is $C_{1-6}$haloalkyl.
(2y) Any of groups of (2a)-(2r), wherein
each $R^3$ is independently halogen or $C_{1-6}$alkyl.
(2z) Any of groups of (2a)-(2r), wherein
each $R^3$ is halogen.
(2aa) Any of groups of (2a)-(2r), wherein
each $R^3$ is $C_{1-6}$alkyl.
(2bb) Any of groups of (2a)-(2aa), wherein
ring A is substituted with one to four $R^2$ groups.
(2cc) Any of groups of (2a)-(2aa), wherein
ring A is substituted with one to three $R^2$ groups.
(2dd) Any of groups of (2a)-(2aa), wherein
ring A is substituted with one or two $R^2$ groups.
(2ee) Any of groups of (2a)-(2aa), wherein
ring A is substituted with one $R^2$ group.
(2ff) Any of groups of (2a)-(2aa), wherein
ring A is unsubstituted.
(2gg) Any of groups of (2a)-(2ff), wherein
ring B is substituted with one to three $R^3$ groups.
(2hh) Any of groups of (2a)-(2ff), wherein
ring B is substituted with one or two $R^3$ groups.
(2ii) Any of groups of (2a)-(2ff), wherein
ring B is substituted with one $R^3$ group.
(2jj) Any of groups of (2a)-(2ff), wherein
ring B is unsubstituted.
(2kk) Any of groups of (2a)-(2jj), wherein
wherein each $R^b$ is independently hydrogen or $C_{1-6}$ alkyl, and
wherein each $R^c$ is independently hydrogen or $C_{1-6}$ alkyl.
(2ll) Any of groups of (2a)-(2jj), wherein
wherein each $R^b$ is $C_{1-6}$ alkyl, and
wherein each $R^c$ is independently hydrogen or $C_{1-6}$ alkyl.
(2 mm) Any of groups of (2a)-(2jj), wherein
wherein each $R^b$ is independently hydrogen or $C_{1-6}$ alkyl, and
wherein each $R^c$ is $C_{1-6}$ alkyl.
(2nn) Any of groups of (2a)-(2jj), wherein
wherein each $R^b$ is hydrogen, and
wherein each $R^c$ is independently hydrogen or $C_{1-6}$ alkyl.
(2oo) Any of groups of (2a)-(2jj), wherein
wherein each $R^b$ is independently hydrogen or $C_{1-6}$ alkyl, and
wherein each $R^c$ is hydrogen.

R and R' are Selected from One of the Following Groups (3a)-(3ii):

(3a) R and R' are independently hydrogen, halogen, $C_{1-6}$alkyl or $C_{1-6}$ haloalkyl;
or R and R' taken together with the carbon atoms to which they are attached form a pyrrole or phenyl.
(3b) R and R' are independently hydrogen, halogen, $C_{1-6}$alkyl or $C_{1-6}$ haloalkyl.
(3c) R and R' taken together with the carbon atoms to which they are attached form a pyrrole or phenyl.
(3d) R and R' are independently hydrogen, halogen or $C_{1-6}$alkyl;
or R and R' taken together with the carbon atoms to which they are attached form a pyrrole or phenyl.
(3e) R and R' are independently hydrogen or halogen;
or R and R' taken together with the carbon atoms to which they are attached form a pyrrole or phenyl.
(3f) R and R' are independently hydrogen or $C_{1-6}$alkyl;
or R and R' taken together with the carbon atoms to which they are attached form a pyrrole or phenyl.
(3g) R and R' are independently halogen or $C_{1-6}$alkyl;
or R and R' taken together with the carbon atoms to which they are attached form a pyrrole or phenyl.
(3h) R and R' are independently hydrogen, halogen or $C_{1-6}$alkyl;
or R and R' taken together with the carbon atoms to which they are attached form a pyrrole or phenyl.
(3i) R and R' are independently hydrogen, halogen, $C_{1-6}$alkyl or $C_{1-6}$ haloalkyl;
or R and R' taken together with the carbon atoms to which they are attached form a pyrrole.
(3j) R and R' are independently hydrogen, halogen, $C_{1-6}$alkyl or $C_{1-6}$ haloalkyl.
(3k) R and R' taken together with the carbon atoms to which they are attached form a pyrrole.
(3l) R and R' are independently hydrogen, halogen or $C_{1-6}$alkyl;
or R and R' taken together with the carbon atoms to which they are attached form a pyrrole.
(3m) R and R' are independently hydrogen or halogen;
or R and R' taken together with the carbon atoms to which they are attached form a pyrrole.
(3n) R and R' are independently hydrogen or $C_{1-6}$alkyl;
or R and R' taken together with the carbon atoms to which they are attached form a pyrrole.
(3o) R and R' are independently halogen or $C_{1-6}$alkyl;
or R and R' taken together with the carbon atoms to which they are attached form a pyrrole.
(3p) R and R' are independently hydrogen, halogen or $C_{1-6}$alkyl;
or R and R' taken together with the carbon atoms to which they are attached form a pyrrole.
(3q) R and R' are independently hydrogen, halogen, $C_{1-6}$alkyl or $C_{1-6}$ haloalkyl;
or R and R' taken together with the carbon atoms to which they are attached form a phenyl.
(3r) R and R' are independently hydrogen, halogen, $C_{1-6}$alkyl or $C_{1-6}$ haloalkyl.
(3s) R and R' taken together with the carbon atoms to which they are attached form a phenyl.
(3t) R and R' are independently hydrogen, halogen or $C_{1-6}$alkyl;
or R and R' taken together with the carbon atoms to which they are attached form a phenyl.
(3u) R and R' are independently hydrogen or halogen;
or R and R' taken together with the carbon atoms to which they are attached form a phenyl.

(3v) R and R' are independently hydrogen or $C_{1-6}$alkyl; or R and R' taken together with the carbon atoms to which they are attached form a phenyl.
(3w) R and R' are independently halogen or $C_{1-6}$alkyl; or R and R' taken together with the carbon atoms to which they are attached form a phenyl.
(3x) R and R' are independently hydrogen, halogen or $C_{1-6}$alkyl; or R and R' taken together with the carbon atoms to which they are attached form a phenyl.
(3y) R' is hydrogen and $R^1$ is hydrogen, halogen, $C_{1-6}$alkyl or $C_{1-6}$ haloalkyl.
(3z) R' is hydrogen and $R^1$ is halogen, $C_{1-6}$alkyl or $C_{1-6}$ haloalkyl.
(3aa) R' is hydrogen and $R^1$ is halogen or $C_{1-6}$alkyl.
(3bb) R' is hydrogen and $R^1$ is halogen or $C_{1-6}$ haloalkyl.
(3cc) R' is hydrogen and $R^1$ is $C_{1-6}$alkyl or $C_{1-6}$ haloalkyl.
(3dd) R' is hydrogen and $R^1$ is halogen.
(3ee) R' is hydrogen and $R^1$ is $C_{1-6}$alkyl.
(3ff) R' is hydrogen and $R^1$ is methyl.
(3gg) R' is hydrogen and $R^1$ is ethyl.
(3hh) R' is hydrogen and $R^1$ is $C_{1-6}$ haloalkyl.
(3ii) R' is hydrogen and $R^1$ is hydrogen.

Particular embodiments of this aspect of the invention comprise compounds of any one of the formulae (I) and (Ia)-(Io), each as defined in each of the following rows (or a pharmaceutically acceptable salt, prodrug, or N-oxide thereof, or a solvate or hydrate thereof), wherein each entry is a group number as defined above (e.g., (3gg) refers to R' is hydrogen and $R^1$ is ethyl), and a dash "-" indicates that the variable is as defined in embodiment $I_1$ or defined according to any one of the applicable variable definitions (1a)-(1mm), (2a)-(2oo) and (3a)-(3ii) [e.g., when A is a dash, it can be either as defined in any of embodiments $I_1$-$I_8$ or any one of applicable definitions (1a)-(1mm)]:

|  | (I) | A | Z | R/R' |
|---|---|---|---|---|
| (1)-1 | (Ia) | (1a) | (2a) | (3a) |
| (1)-2 | (Ia) | (1b) | (2b) | (3b) |
| (1)-3 | (Ia) | (1c) | (2d) | (3c) |
| (1)-4 | (Ia) | (1d) | (2i) | (3f) |
| (1)-5 | (Ia) | (1f) | (2j) | (3k) |
| (1)-6 | (Ia) | (1n) | (2l) | (3n) |
| (1)-7 | (Ia) | (1r) | (2n) | (3s) |
| (1)-8 | (Ia) | (1s) | (2p) | (3v) |
| (1)-9 | (Ia) | (1v) | (2r) | (3y) |
| (1)-10 | (Ia) | (1x) | (2y) | (3aa) |
| (1)-11 | (Ia) | (1y) | (2z) | (3ee) |
| (1)-12 | (Ia) | (1z) | (2aa) | (3c) |
| (1)-13 | (Ia) | (1ee) | (2dd) | (3f) |
| (1)-14 | (Ia) | (1ff) | (2ee) | (3k) |
| (1)-15 | (Ia) | (1gg) | (2ff) | (3n) |
| (1)-16 | (Ia) | (1ii) | (2ii) | (3s) |
| (1)-17 | (Ia) | (1jj) | (2jj) | (3b) |
| (1)-18 | (Ia) | (1kk) | (2ll) | (3c) |
| (1)-19 | (Ia) | (1ll) | (2nn) | (3a) |
| (1)-20 | (Ia) | (1mm) | (2ii) | (3b) |
| (1)-21 | (Ib) | (1a) | (2jj) | (3c) |
| (1)-22 | (Ib) | (1b) | (2ff) | (3b) |
| (1)-23 | (Ib) | (1c) | (2ii) | (3c) |
| (1)-24 | (Ib) | (1d) | (2jj) | (3f) |
| (1)-25 | (Ib) | (1f) | (2jj) | (3k) |
| (1)-26 | (Ib) | (1n) | (2ll) | (3n) |
| (1)-27 | (Ib) | (1r) | (2nn) | (3s) |
| (1)-28 | (Ib) | (1s) | (2ee) | (3v) |
| (1)-29 | (Ib) | (1v) | (2ff) | (3y) |
| (1)-30 | (Ib) | (1x) | (2jj) | (3aa) |
| (1)-31 | (Ib) | (1y) | (2ll) | (3ee) |
| (1)-32 | (Ib) | (1z) | (2nn) | (3c) |
| (1)-33 | (Ib) | (1ee) | (2d) | (3f) |
| (1)-34 | (Ib) | (1ff) | (2i) | (3k) |
| (1)-35 | (Ib) | (1gg) | (2j) | (3n) |
| (1)-36 | (Ib) | (1ii) | (2l) | (3s) |
| (1)-37 | (Ib) | (1jj) | (2n) | (3c) |
| (1)-38 | (Ib) | (1kk) | (2ii) | (3f) |
| (1)-39 | (Ib) | (1ll) | (2jj) | (3k) |
| (1)-40 | (Ib) | (1mm) | (2j) | (3n) |
| (1)-41 | (Ic) | (1a) | (2l) | (3s) |
| (1)-42 | (Ic) | (1b) | (2n) | (3c) |
| (1)-43 | (Ic) | (1c) | (2r) | (3k) |
| (1)-44 | (Ic) | (1d) | (2y) | (3a) |
| (1)-45 | (Ic) | (1f) | (2z) | (3b) |
| (1)-46 | (Ic) | (1n) | (2aa) | (3c) |
| (1)-47 | (Ic) | (1r) | (2aa) | (3f) |
| (1)-48 | (Ic) | (1s) | (2dd) | (3k) |
| (1)-49 | (Ic) | (1v) | (2ee) | (3n) |
| (1)-50 | (Ic) | (1x) | (2ff) | (3s) |
| (1)-51 | (Ic) | (1y) | (2ii) | (3v) |
| (1)-52 | (Ic) | (1z) | (2jj) | (3y) |
| (1)-53 | (Ic) | (1ee) | (2ll) | (3aa) |
| (1)-54 | (Ic) | (1ff) | (2nn) | (3ee) |
| (1)-55 | (Ic) | (1gg) | (2ee) | (3v) |
| (1)-56 | (Ic) | (1ii) | (2ff) | (3y) |
| (1)-57 | (Ic) | (1jj) | (2ii) | (3aa) |
| (1)-58 | (Ic) | (1kk) | (2jj) | (3ee) |
| (1)-59 | (Ic) | (1ll) | (2ll) | (3b) |
| (1)-60 | (Ic) | (1mm) | (2nn) | (3c) |
| (1)-61 | (Id) | (1a) | (2d) | (3f) |
| (1)-62 | (Id) | (1b) | (2i) | (3k) |
| (1)-63 | (Id) | (1c) | (2j) | (3n) |
| (1)-64 | (Id) | (1d) | (2l) | (3s) |
| (1)-65 | (Id) | (1f) | (2n) | (3v) |
| (1)-66 | (Id) | (1n) | (2p) | (3y) |
| (1)-67 | (Id) | (1r) | (2ii) | (3aa) |
| (1)-68 | (Id) | (1s) | (2jj) | (3ee) |
| (1)-69 | (Id) | (1v) | (2z) | (3s) |
| (1)-70 | (Id) | (1x) | (2aa) | (3v) |
| (1)-71 | (Id) | (1y) | (2r) | (3y) |
| (1)-72 | (Id) | (1z) | (2y) | (3aa) |
| (1)-73 | (Id) | (1ee) | (2z) | (3ee) |
| (1)-74 | (Id) | (1ff) | (2aa) | (3n) |
| (1)-75 | (Id) | (1gg) | (2jj) | (3a) |
| (1)-76 | (Id) | (1ii) | (2ll) | (3b) |
| (1)-77 | (Id) | (1jj) | (2nn) | (3c) |
| (1)-78 | (Id) | (1kk) | (2nn) | (3c) |
| (1)-79 | (Id) | (1ll) | (2ee) | (3f) |
| (1)-80 | (Id) | (1mm) | (2ff) | (3k) |
| (1)-81 | (Ie) | (1a) | (2jj) | (3n) |
| (1)-82 | (Ie) | (1b) | (2d) | (3s) |
| (1)-83 | (Ie) | (1c) | (2i) | (3c) |
| (1)-84 | (Ie) | (1d) | (2j) | (3f) |
| (1)-85 | (Ie) | (1f) | (2l) | (3k) |
| (1)-86 | (Ie) | (1n) | (2n) | (3n) |
| (1)-87 | (Ie) | (1r) | (2ee) | (3s) |
| (1)-88 | (Ie) | (1s) | (2ff) | (3v) |
| (1)-89 | (Ie) | (1v) | (2b) | (3y) |
| (1)-90 | (Ie) | (1x) | (2d) | (3aa) |
| (1)-91 | (Ie) | (1y) | (2i) | (3ee) |
| (1)-92 | (Ie) | (1z) | (2j) | (3f) |
| (1)-93 | (Ie) | (1ee) | (2l) | (3k) |
| (1)-94 | (Ie) | (1ff) | (2n) | (3n) |
| (1)-95 | (Ie) | (1gg) | (2ii) | (3s) |
| (1)-96 | (Ie) | (1ii) | (2jj) | (3b) |
| (1)-97 | (Ie) | (1jj) | (2y) | (3c) |
| (1)-98 | (Ie) | (1kk) | (2z) | (3f) |
| (1)-99 | (Ie) | (1ll) | (2aa) | (3k) |
| (1)-100 | (Ie) | (1mm) | (2dd) | (3n) |
| (1)-101 | (If) | (1a) | (2ee) | (3s) |
| (1)-102 | (If) | (1b) | (2ff) | (3f) |
| (1)-103 | (If) | (1c) | (2ii) | (3k) |
| (1)-104 | (If) | (1d) | (2jj) | (3n) |
| (1)-105 | (If) | (1f) | (2ll) | (3s) |
| (1)-106 | (If) | (1n) | (2nn) | (3f) |
| (1)-107 | (If) | (1r) | (2nn) | (3k) |
| (1)-108 | (If) | (1s) | (2ee) | (3n) |
| (1)-109 | (If) | (1v) | (2ff) | (3c) |
| (1)-110 | (If) | (1x) | (2jj) | (3f) |
| (1)-111 | (If) | (1y) | (2ii) | (3k) |

-continued

|  | (I) | A | Z | R/R' |
|---|---|---|---|---|
| (1)-112 | (If) | (1z) | (2jj) | (3n) |
| (1)-113 | (If) | (1ee) | (2ll) | (3s) |
| (1)-114 | (If) | (1ff) | (2nn) | (3c) |
| (1)-115 | (If) | (1gg) | (2b) | (3f) |
| (1)-116 | (If) | (1ii) | (2d) | (3k) |
| (1)-117 | (If) | (1jj) | (2i) | (3n) |
| (1)-118 | (If) | (1kk) | (2j) | (3s) |
| (1)-119 | (If) | (1ll) | (2l) | (3v) |
| (1)-120 | (If) | (1mm) | (2ii) | (3y) |
| (1)-121 | (Ig) | (1a) | (2jj) | (3aa) |
| (1)-122 | (Ig) | (1b) | (2r) | (3ee) |
| (1)-123 | (Ig) | (1c) | (2y) | (3c) |
| (1)-124 | (Ig) | (1d) | (2r) | (3f) |
| (1)-125 | (Ig) | (1f) | (2y) | (3k) |
| (1)-126 | (Ig) | (1n) | (2z) | (3n) |
| (1)-127 | (Ig) | (1r) | (2aa) | (3s) |
| (1)-128 | (Ig) | (1s) | (2r) | (3n) |
| (1)-129 | (Ig) | (1v) | (2y) | (3c) |
| (1)-130 | (Ig) | (1x) | (2z) | (3f) |
| (1)-131 | (Ig) | (1y) | (2aa) | (3k) |
| (1)-132 | (Ig) | (1z) | (2nn) | (3n) |
| (1)-133 | (Ig) | (1ee) | (2d) | (3s) |
| (1)-134 | (Ig) | (1ff) | (2i) | (3v) |
| (1)-135 | (Ig) | (1gg) | (2j) | (3y) |
| (1)-136 | (Ig) | (1ii) | (2l) | (3aa) |
| (1)-137 | (Ig) | (1jj) | (2n) | (3ee) |
| (1)-138 | (Ig) | (1kk) | (2aa) | (3v) |
| (1)-139 | (Ig) | (1ll) | (2i) | (3y) |
| (1)-140 | (Ig) | (1mm) | (2j) | (3aa) |
| (1)-141 | (Ih) | (1a) | (2l) | (3ee) |
| (1)-142 | (Ih) | (1b) | (2ii) | (3c) |
| (1)-143 | (Ih) | (1c) | (2jj) | (3v) |
| (1)-144 | (Ih) | (1d) | (2r) | (3y) |
| (1)-145 | (Ih) | (1f) | (2y) | (3aa) |
| (1)-146 | (Ih) | (1n) | (2z) | (3c) |
| (1)-147 | (Ih) | (1r) | (2aa) | (3v) |
| (1)-148 | (Ih) | (1s) | (2dd) | (3y) |
| (1)-149 | (Ih) | (1v) | (2ee) | (3aa) |
| (1)-150 | (Ih) | (1x) | (2ff) | (3ee) |
| (1)-151 | (Ih) | (1y) | (2ii) | (3b) |
| (1)-152 | (Ih) | (1z) | (2jj) | (3ee) |
| (1)-153 | (Ih) | (1ee) | (2ll) | (3b) |
| (1)-154 | (Ih) | (1ff) | (2nn) | (3c) |
| (1)-155 | (Ih) | (1gg) | (2ee) | (3f) |
| (1)-156 | (Ih) | (1ii) | (2ff) | (3k) |
| (1)-157 | (Ih) | (1jj) | (2i) | (3n) |
| (1)-158 | (Ih) | (1kk) | (2j) | (3s) |
| (1)-159 | (Ih) | (1ll) | (2l) | (3v) |
| (1)-160 | (Ih) | (1mm) | (2n) | (3y) |
| (1)-161 | (Ii) | (1a) | (2b) | (3aa) |
| (1)-162 | (Ii) | (1b) | (2ii) | (3ee) |
| (1)-163 | (Ii) | (1c) | (2jj) | (3c) |
| (1)-164 | (Ii) | (1d) | (2r) | (3f) |
| (1)-165 | (Ii) | (1f) | (2y) | (3k) |
| (1)-166 | (Ii) | (1n) | (2z) | (3n) |
| (1)-167 | (Ii) | (1r) | (2aa) | (3s) |
| (1)-168 | (Ii) | (1s) | (2r) | (3b) |
| (1)-169 | (Ii) | (1v) | (2y) | (3c) |
| (1)-170 | (Ii) | (1x) | (2z) | (3v) |
| (1)-171 | (Ii) | (1y) | (2aa) | (3y) |
| (1)-172 | (Ii) | (1z) | (2dd) | (3aa) |
| (1)-173 | (Ii) | (1ee) | (2ee) | (3ee) |
| (1)-174 | (Ii) | (1ff) | (2ff) | (3b) |
| (1)-175 | (Ii) | (1gg) | (2ii) | (3c) |
| (1)-176 | (Ii) | (1ii) | (2jj) | (3f) |
| (1)-177 | (Ii) | (1jj) | (2ll) | (3k) |
| (1)-178 | (Ii) | (1kk) | (2nn) | (3n) |
| (1)-179 | (Ii) | (1ll) | (2ee) | (3s) |
| (1)-180 | (Ii) | (1l) | (2ff) | (3v) |
| (1)-181 | (Ij) | (1a) | (2d) | (3y) |
| (1)-182 | (Ij) | (1b) | (2i) | (3aa) |
| (1)-183 | (Ij) | (1c) | (2j) | (3ee) |
| (1)-184 | (Ij) | (1d) | (2l) | (3c) |
| (1)-185 | (Ij) | (1f) | (2n) | (3f) |
| (1)-186 | (Ij) | (1n) | (2ee) | (3k) |
| (1)-187 | (Ij) | (1r) | (2ff) | (3n) |
| (1)-188 | (Ij) | (1s) | (2b) | (3s) |
| (1)-189 | (Ij) | (1v) | (2d) | (3c) |
| (1)-190 | (Ij) | (1x) | (2ii) | (3f) |
| (1)-191 | (Ij) | (1y) | (2jj) | (3k) |
| (1)-192 | (Ij) | (1z) | (2l) | (3n) |
| (1)-193 | (Ij) | (1ee) | (2r) | (3s) |
| (1)-194 | (Ij) | (1ff) | (2y) | (3v) |
| (1)-195 | (Ij) | (1gg) | (2z) | (3y) |
| (1)-196 | (Ij) | (1ii) | (2aa) | (3aa) |
| (1)-197 | (Ij) | (1jj) | (2z) | (3ee) |
| (1)-198 | (Ij) | (1kk) | (2aa) | (3s) |
| (1)-199 | (Ij) | (1ll) | (2dd) | (3v) |
| (1)-200 | (Ij) | (1mm) | (2ee) | (3y) |
| (1)-201 | (Ik) | (1a) | (2ff) | (3aa) |
| (1)-202 | (Ik) | (1b) | (2ii) | (3ee) |
| (1)-203 | (Ik) | (1c) | (2jj) | (3c) |
| (1)-204 | (Ik) | (1d) | (2ll) | (3f) |
| (1)-205 | (Ik) | (1f) | (2nn) | (3k) |
| (1)-206 | (Ik) | (1n) | (2ii) | (3n) |
| (1)-207 | (Ik) | (1r) | (2jj) | (3s) |
| (1)-208 | (Ik) | (1s) | (2ll) | (3b) |
| (1)-209 | (Ik) | (1v) | (2nn) | (3c) |
| (1)-210 | (Ik) | (1x) | (2b) | (3f) |
| (1)-211 | (Ik) | (1y) | (2d) | (3k) |
| (1)-212 | (Ik) | (1z) | (2i) | (3n) |
| (1)-213 | (Ik) | (1ee) | (2j) | (3s) |
| (1)-214 | (Ik) | (1ff) | (2l) | (3v) |
| (1)-215 | (Ik) | (1gg) | (2ii) | (3y) |
| (1)-216 | (Ik) | (1ii) | (2jj) | (3aa) |
| (1)-217 | (Ik) | (1jj) | (2r) | (3ee) |
| (1)-218 | (Ik) | (1kk) | (2r) | (3b) |
| (1)-219 | (Ik) | (1ll) | (2y) | (3c) |
| (1)-220 | (Ik) | (1mm) | (2z) | (3f) |
| (1)-221 | (Il) | (1a) | (2aa) | (3k) |
| (1)-222 | (Il) | (1b) | (2ee) | (3n) |
| (1)-223 | (Il) | (1c) | (2ff) | (3s) |
| (1)-224 | (Il) | (1d) | (2ii) | (3v) |
| (1)-225 | (Il) | (1f) | (2jj) | (3y) |
| (1)-226 | (Il) | (1n) | (2ll) | (3aa) |
| (1)-227 | (Il) | (1r) | (2nn) | (3ee) |
| (1)-228 | (Il) | (1s) | (2ii) | (3f) |
| (1)-229 | (Il) | (1v) | (2jj) | (3k) |
| (1)-230 | (Il) | (1x) | (2y) | (3n) |
| (1)-231 | (Il) | (1y) | (2z) | (3s) |
| (1)-232 | (Il) | (1z) | (2aa) | (3a) |
| (1)-233 | (Il) | (1ee) | (2ii) | (3b) |
| (1)-234 | (Il) | (1ff) | (2jj) | (3c) |
| (1)-235 | (Il) | (1gg) | (2j) | (3f) |
| (1)-236 | (Il) | (1ii) | (2l) | (3k) |
| (1)-237 | (Il) | (1jj) | (2n) | (3n) |
| (1)-238 | (Il) | (1kk) | (2j) | (3s) |
| (1)-239 | (Il) | (1ll) | (2l) | (3v) |
| (1)-240 | (Il) | (1mm) | (2n) | (3c) |
| (1)-241 | (Im) | (1a) | (2ii) | (3v) |
| (1)-242 | (Im) | (1b) | (2jj) | (3y) |
| (1)-243 | (Im) | (1c) | (2ii) | (3aa) |
| (1)-244 | (Im) | (1d) | (2jj) | (3ee) |
| (1)-245 | (Im) | (1f) | (2ll) | (3b) |
| (1)-246 | (Im) | (1n) | (2nn) | (3c) |
| (1)-247 | (Im) | (1r) | (2ee) | (3f) |
| (1)-248 | (Im) | (1s) | (2ff) | (3k) |
| (1)-249 | (Im) | (1v) | (2ii) | (3n) |
| (1)-250 | (Im) | (1x) | (2jj) | (3s) |
| (1)-251 | (Im) | (1y) | (2ll) | (3v) |
| (1)-252 | (Im) | (1z) | (2nn) | (3y) |
| (1)-253 | (Im) | (1ee) | (2d) | (3aa) |
| (1)-254 | (Im) | (1ff) | (2i) | (3ee) |
| (1)-255 | (Im) | (1gg) | (2ii) | (3f) |
| (1)-256 | (Im) | (1ii) | (2jj) | (3k) |
| (1)-257 | (Im) | (1jj) | (2n) | (3n) |
| (1)-258 | (Im) | (1kk) | (2i) | (3c) |
| (1)-259 | (Im) | (1ll) | (2j) | (3f) |
| (1)-260 | (Im) | (1mm) | (2l) | (3k) |
| (1)-261 | (In) | (1a) | (2n) | (3n) |
| (1)-262 | (In) | (1b) | (2p) | (3s) |
| (1)-263 | (In) | (1c) | (2r) | (3c) |
| (1)-264 | (In) | (1d) | (2ii) | (3v) |
| (1)-265 | (In) | (1f) | (2jj) | (3y) |

|  | (I) | A | Z | R/R' |
|---|---|---|---|---|
| (1)-266 | (In) | (1n) | (2aa) | (3aa) |
| (1)-267 | (In) | (1r) | (2dd) | (3ee) |
| (1)-268 | (In) | (1s) | (2ee) | (3b) |
| (1)-269 | (In) | (1v) | (2ff) | (3a) |
| (1)-270 | (In) | (1x) | (2ii) | (3b) |
| (1)-271 | (In) | (1y) | (2jj) | (3c) |
| (1)-272 | (In) | (1z) | (2ll) | (3f) |
| (1)-273 | (In) | (1ee) | (2nn) | (3k) |
| (1)-274 | (In) | (1ff) | (2aa) | (3n) |
| (1)-275 | (In) | (1gg) | (2d) | (3s) |
| (1)-276 | (In) | (1ii) | (2ee) | (3v) |
| (1)-277 | (In) | (1jj) | (2ff) | (3y) |
| (1)-278 | (In) | (1kk) | (2aa) | (3aa) |
| (1)-279 | (In) | (1ll) | (2d) | (3ee) |
| (1)-280 | (In) | (1mm) | (2y) | (3f) |
| (1)-281 | (Io) | (1a) | (2z) | (3k) |
| (1)-282 | (Io) | (1b) | (2aa) | (3n) |
| (1)-283 | (Io) | (1c) | (2ii) | (3s) |
| (1)-284 | (Io) | (1d) | (2jj) | (3f) |
| (1)-285 | (Io) | (1f) | (2ll) | (3k) |
| (1)-286 | (Io) | (1n) | (2nn) | (3n) |
| (1)-287 | (Io) | (1r) | (2i) | (3a) |
| (1)-288 | (Io) | (1s) | (2j) | (3b) |
| (1)-289 | (Io) | (1v) | (2l) | (3c) |
| (1)-290 | (Io) | (1x) | (2n) | (3f) |
| (1)-291 | (Io) | (1y) | (2ee) | (3k) |
| (1)-292 | (Io) | (1z) | (2ff) | (3n) |
| (1)-293 | (Io) | (1ee) | (2i) | (3s) |
| (1)-294 | (Io) | (1ff) | (2j) | (3v) |
| (1)-295 | (Io) | (1gg) | (2l) | (3y) |
| (1)-296 | (Io) | (1ii) | (2n) | (3aa) |
| (1)-297 | (Io) | (1jj) | (2ii) | (3a) |
| (1)-298 | (Io) | (1kk) | (2jj) | (3a) |
| (1)-299 | (Io) | (1ll) | (2ll) | (3b) |
| (1)-300 | (Io) | (1mm) | (2nn) | (3c) |

In some embodiments, the compound of formulae (I) or (Ia)-(Io) is one of the following compounds (or a pharmaceutically acceptable salt, prodrug, or N-oxide thereof, or a solvate or hydrate thereof):

| No. | Structure | Name |
|---|---|---|
| 1 | 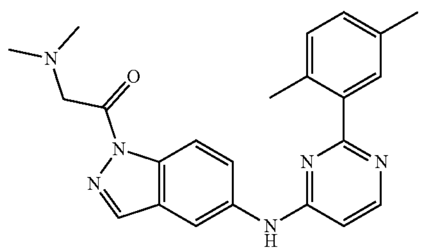 | 2-(Dimethylamino)-1-(5-((2-(2,5-dimethylphenyl)pyrimidin-4-yl)amino)-1H-indazol-1-yl)ethan-1-one |
| 2 | 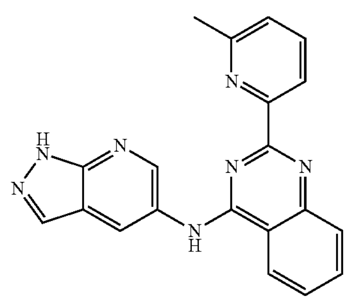 [SMILES: Cc1cccc(-c2nc(Nc3cnc4[nH]ncc4c3)c3ccccc3n2)n1] | 2-(6-Methylpyridin-2-yl)-N-(1H-pyrazolo[3,4-b]pyridin-5-yl)quinazolin-4-amine |
| 3 | 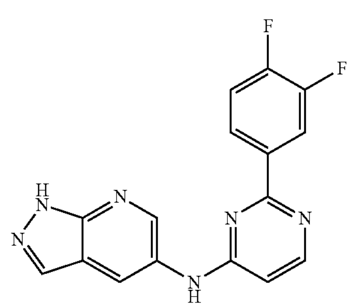 [SMILES: Fc1ccc(-c2nccc(Nc3cnc4[nH]ncc4c3)n2)cc1F] | N-(2-(3,4-Difluorophenyl)pyrimidin-4-yl)-1H-pyrazolo[3,4-b]pyridin-5-amine |

-continued
| No. | Structure | Name |
|---|---|---|
| 4 | 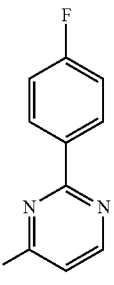 | N-(2-(4-Fluorophenyl)pyrimidin-4-yl)-1H-pyrazolo[3,4-b]pyridin-5-amine |
| 5 | 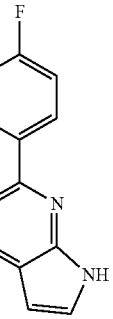 | 2-(4-Fluorophenyl)-N-(1H-indazol-5-yl)-7H-pyrrolo[2,3-d]pyrimidin-4-amine |
| 6 | 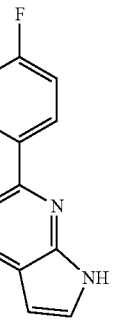 | 2-(3,4-Difluorophenyl)-N-(1H-indazol-5-yl)-7H-pyrrolo[2,3-d]pyrimidin-4-amine |
| 7 | 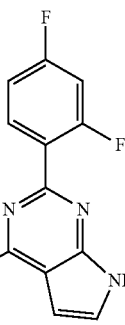 | 2-(2,4-Difluorophenyl)-N-(1H-indazol-5-yl)-7H-pyrrolo[2,3-d]pyrimidin-4-amine |
| 8 | 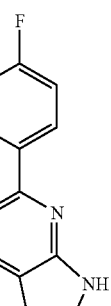 | 2-(4-Fluoro-3-methylphenyl)-N-(1H-indazol-5-yl)-7H-pyrrolo[2,3-d]pyrimidin-4-amine |

-continued
| No. | Structure | Name |
|---|---|---|
| 9 | 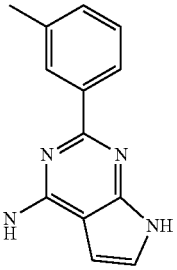 | N-(1H-Indazol-5-yl)-2-(3-methylphenyl)-7H-pyrrolo[2,3-d]pyrimidin-4-amine |
| 10 | 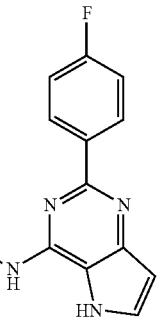 | 2-(4-Fluorophenyl)-N-(1H-indazol-5H-pyrrolo[3,2-d]pyrimidin-4-amine |
| 11 | 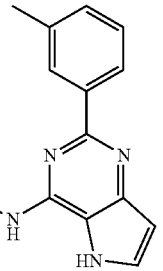 | N-(1H-Indazol-5-yl)-2-(3-methylphenyl)-5H-pyrrolo[3,2-d]pyrimidin-4-amine |
| 12 | 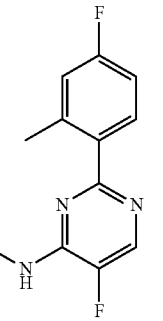 | N-(5-Fluoro-2-(4-fluoro-2-methylphenyl)pyrimidin-4-yl)-1H-pyrazolo[3,4-b]pyridin-5-amine |
| 13 | 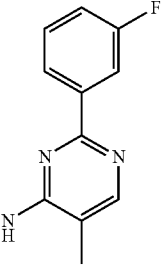 | N-(2-(3-Fluorophenyl)-5-methylpyrimidin-4-yl)-1H-pyrazolo[3,4-b]pyridin-5-amine |

-continued
| No. | Structure | Name |
|---|---|---|
| 14 | 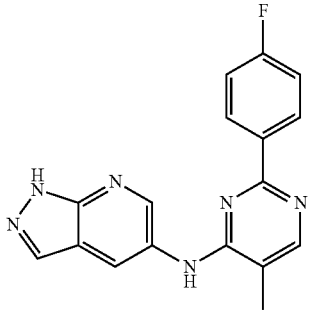 [SMILES: Cc1cnc(-c2ccc(F)cc2)nc1Nc1cnc2[nH]ncc2c1] | N-(2-(4-Fluorophenyl)-5-methylpyrimidin-4-yl)-1H-pyrazolo[3,4-b]pyridin-5-amine |
| 15 | 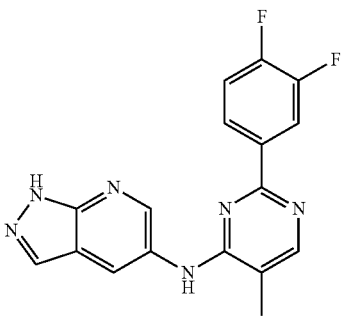 [SMILES: Cc1cnc(-c2ccc(F)c(F)c2)nc1Nc1cnc2[nH]ncc2c1] | N-(2-(3,4-Difluorophenyl)-5-methylpyrimidin-4-yl)-1H-pyrazolo[3,4-b]pyridin-5-amine |
| 16 | 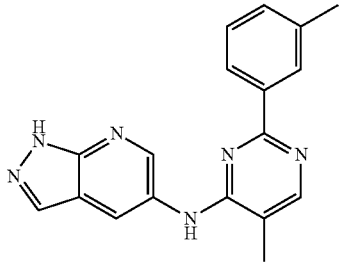 [SMILES: Cc1cccc(-c2ncc(C)c(Nc3cnc4[nH]ncc4c3)n2)c1] | N-(2-(3-Methylphenyl)-5-methylpyrimidin-4-yl)-1H-pyrazolo[3,4-b]pyridin-5-amine |
| 17 | 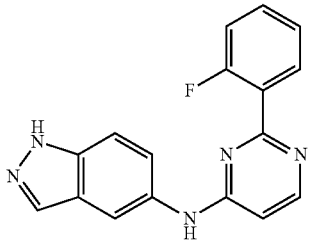 [SMILES: Fc1ccccc1-c1nccc(Nc2ccc3[nH]ncc3c2)n1] | N-(2-(2-Fluorophenyl)pyrimidin-4-yl)-1H-indazol-5-amine |
| 18 | 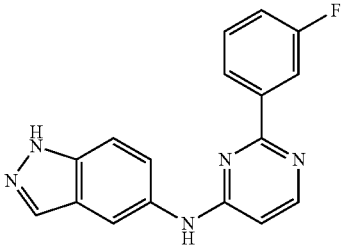 | N-(2-(3-Fluorophenyl)pyrimidin-4-yl)-1H-indazol-5-amine |

-continued

| No. | Structure | Name |
|---|---|---|
| 19 | 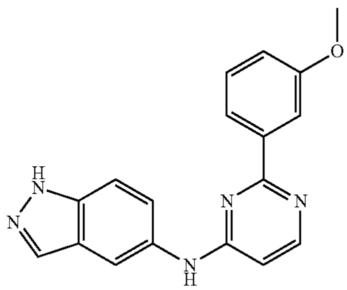 [SMILES: COc1cccc(-c2nccc(Nc3ccc4[nH]ncc4c3)n2)c1] | N-(2-(3-Methoxyphenyl)pyrimidin-4-yl)-1H-indazol-5-amine |
| 20 | 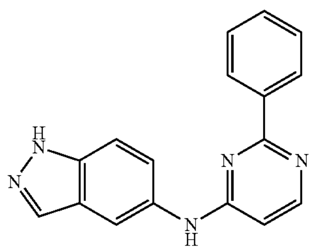 [SMILES: c1ccc(-c2nccc(Nc3ccc4[nH]ncc4c3)n2)cc1] | N-(2-Phenylpyrimidin-4-yl)-1H-indazol-5-amine |
| 21 | 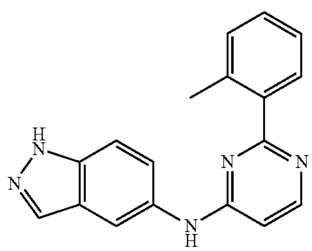 [SMILES: Cc1ccccc1-c1nccc(Nc2ccc3[nH]ncc3c2)n1] | N-(2-(2-Methylphenyl)pyrimidin-4-yl)-1H-indazol-5-amine |
| 22 | 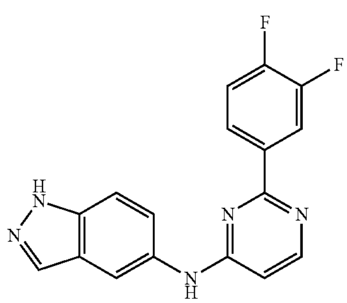 [SMILES: Fc1ccc(-c2nccc(Nc3ccc4[nH]ncc4c3)n2)cc1F] | N-(2-(3,4-Difluorophenyl)pyrimidin-4-yl)-1H-indazol-5-amine |
| 23 | 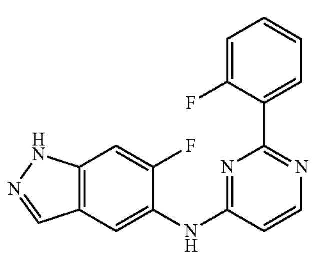 [SMILES: Fc1cc2[nH]ncc2cc1Nc1ccnc(-c2ccccc2F)n1] | 6-Fluoro-N-(2-(2-fluorophenyl)pyrimidin-4-yl)-1H-indazol-5-amine |

-continued

| No. | Structure | Name |
|---|---|---|
| 24 | 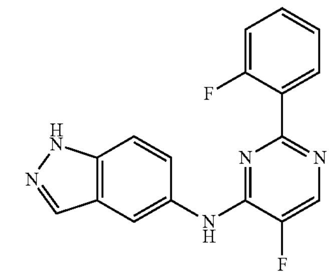 [SMILES: Fc1ccccc1-c1ncc(F)c(Nc2ccc3[nH]ncc3c2)n1] | N-(5-Fluoro-2-(2-fluorophenyl)pyrimidin-4-yl)-1H-indazol-5-amine |
| 25 | 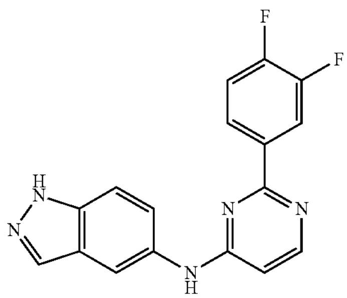 [SMILES: Fc1ccc(-c2nccc(Nc3ccc4[nH]ncc4c3)n2)cc1F] | N-(2-(3,4-Difluorophenyl)pyrimidin-4-yl)-1H-indazol-5-amine |
| 26 | 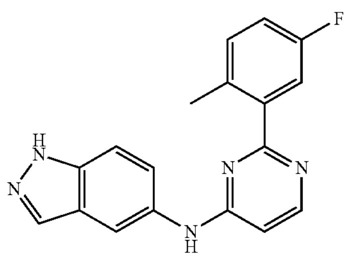 [SMILES: Cc1ccc(F)cc1-c1nccc(Nc2ccc3[nH]ncc3c2)n1] | N-(2-(5-fluoro-2-methylphenyl)pyrimidin-4-yl)-1H-indazol-5-amine |
| 27 | 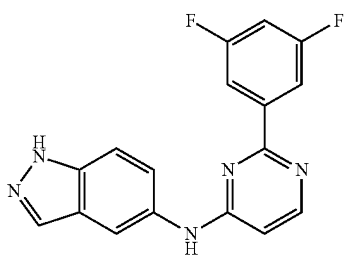 [SMILES: Fc1cc(F)cc(-c2nccc(Nc3ccc4[nH]ncc4c3)n2)c1] | N-(2-(3,5-Difluorophenyl)pyrimidin-4-yl)-1H-indazol-5-amine |
| 28 | 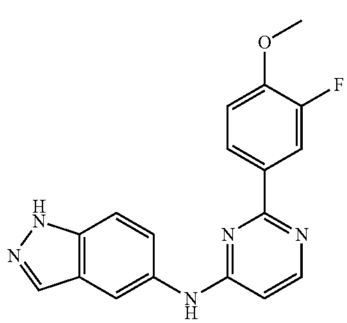 [SMILES: COc1ccc(-c2nccc(Nc3ccc4[nH]ncc4c3)n2)cc1F] | N-(2-(3-Fluoro-4-methoxyphenyl)pyrimidin-4-yl)-1H-indazol-5-amine |

-continued

| No. | Structure | Name |
|---|---|---|
| 29 | 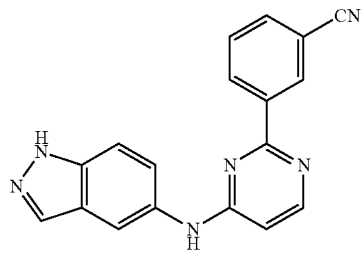 [SMILES: N#Cc1cccc(-c2nccc(Nc3ccc4[nH]ncc4c3)n2)c1] | N-(2-(3-Cyanophenyl)pyrimidin-4-yl)-1H-indazol-5-amine |
| 30 | 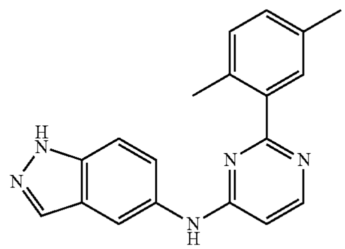 [SMILES: Cc1ccc(C)c(-c2nccc(Nc3ccc4[nH]ncc4c3)n2)c1] | N-(2-(2,5-Dimethylphenyl)pyrimidin-4-yl)-1H-indazol-5-amine |
| 31 | 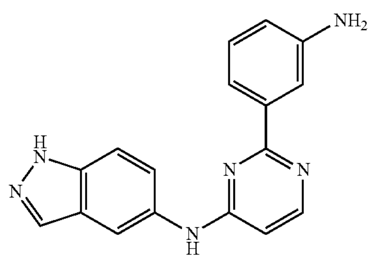 [SMILES: Nc1cccc(-c2nccc(Nc3ccc4[nH]ncc4c3)n2)c1] | N-(2-(3-Aminophenyl)pyrimidin-4-yl)-1H-indazol-5-amine |
| 32 | 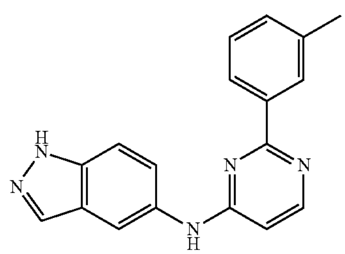 [SMILES: Cc1cccc(-c2nccc(Nc3ccc4[nH]ncc4c3)n2)c1] | N-(2-(3-Methylphenyl)pyrimidin-4-yl)-1H-indazol-5-amine |
| 33 | 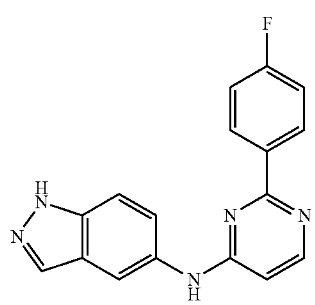 [SMILES: Fc1ccc(-c2nccc(Nc3ccc4[nH]ncc4c3)n2)cc1] | N-(2-(4-Fluorophenyl)pyrimidin-4-yl)-1H-indazol-5-amine |
| 34 | 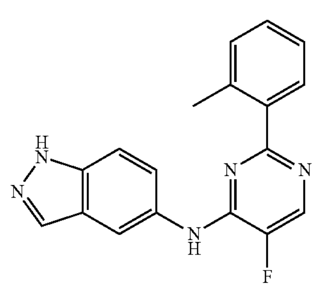 [SMILES: Cc1ccccc1-c1ncc(F)c(Nc2ccc3[nH]ncc3c2)n1] | N-(5-Fluoro-2-(methylphenyl)pyrimidin-4-yl)-1H-indazol-5-amine |

-continued

| No. | Structure | Name |
|---|---|---|
| 35 | 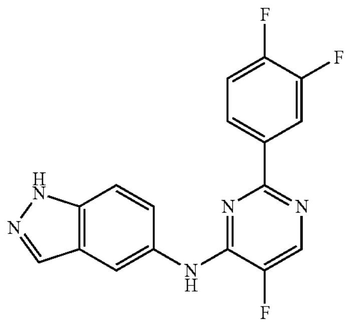 [SMILES: Fc1ccc(-c2ncc(F)c(Nc3ccc4[nH]ncc4c3)n2)cc1F] | N-(2-(3,4-Difluorophenyl)-5-fluoropyrimidin-4-yl)-1H-indazol-5-amine |
| 36 | 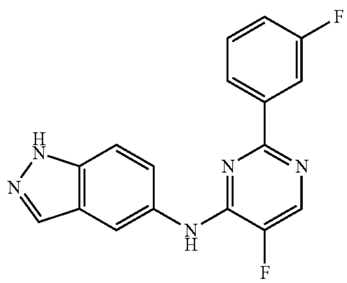 [SMILES: Fc1cccc(-c2ncc(F)c(Nc3ccc4[nH]ncc4c3)n2)c1] | N-(5-Fluoro-2-(3-fluorophenyl)pyrimidin-4-yl)-1H-indazol-5-amine |
| 37 | 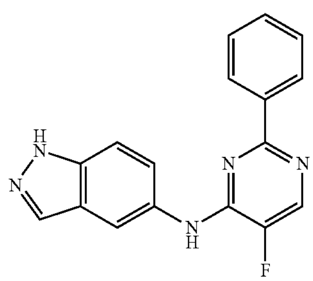 [SMILES: Fc1cnc(-c2ccccc2)nc1Nc1ccc2[nH]ncc2c1] | N-(5-Fluoro-2-phenylpyrimidin-4-yl)-1H-indazol-5-amine |
| 38 | 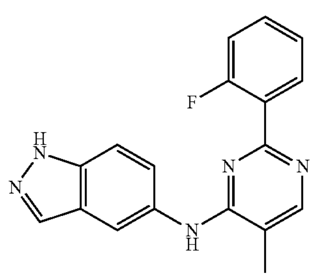 [SMILES: Cc1cnc(-c2ccccc2F)nc1Nc1ccc2[nH]ncc2c1] | N-(2-(2-Fluorophenyl)-5-methylpyrimidin-4-yl)-1H-indazol-5-amine |
| 39 | 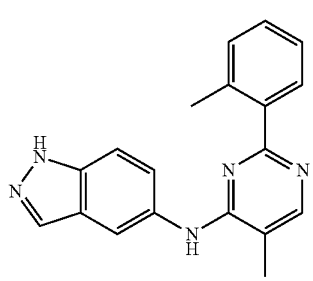 [SMILES: Cc1ccccc1-c1ncc(C)c(Nc2ccc3[nH]ncc3c2)n1] | N-(2-(2-Methylphenyl)-5-methylpyrimidin-4-yl)-1H-indazol-5-amine |

-continued

| No. | Structure | Name |
|---|---|---|
| 40 | 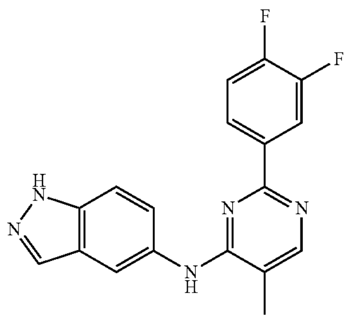 [SMILES: Cc1cnc(-c2ccc(F)c(F)c2)nc1Nc1ccc2[nH]ncc2c1] | N-(2-(3,4-Difluorophenyl)-5-methylpyrimidin-4-yl)-1H-indazol-5-amine |
| 41 | 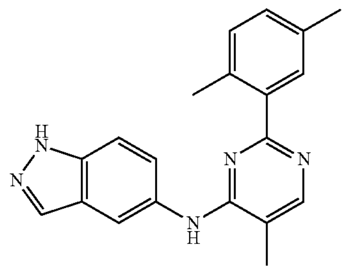 [SMILES: Cc1ccc(C)c(-c2ncc(C)c(Nc3ccc4[nH]ncc4c3)n2)c1] | N-(2-(2,5-Dimethylphenyl)-5-methylpyrimidin-4-yl)-1H-indazol-5-amine |
| 42 | 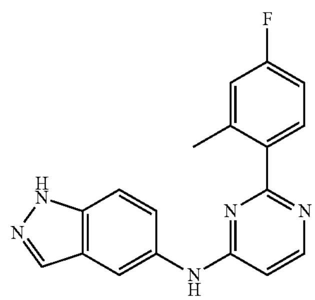 [SMILES: Cc1cc(F)ccc1-c1nccc(Nc2ccc3[nH]ncc3c2)n1] | N-(2-(4-Fluoro-2-methylphenyl)pyrimidin-4-yl)-1H-indazol-5-amine |
| 43 | 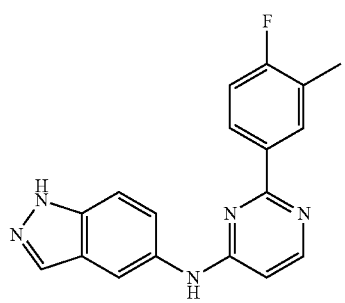 [SMILES: Cc1cc(-c2nccc(Nc3ccc4[nH]ncc4c3)n2)ccc1F] | N-(2-(4-Fluoro-3-methylphenyl)pyrimidin-4-yl)-1H-indazol-5-amine |
| 44 | 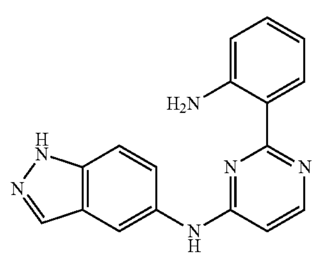 [SMILES: Nc1ccccc1-c1nccc(Nc2ccc3[nH]ncc3c2)n1] | N-(2-(2-Aminophenyl)pyrimidin-4-yl)-1H-indazol-5-amine |

| No. | Structure | Name |
|---|---|---|
| 45 | 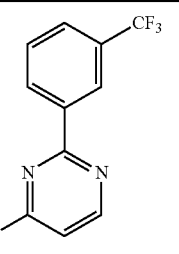 | N-(2-(3-Trifluoromethylphenyl)pyrimidin-4-yl)-1H-indazol-5-amine |
| 46 | 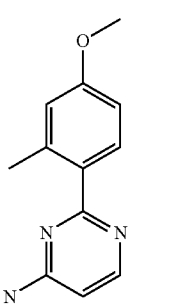 | N-(2-(4-Methoxy-2-methylphenyl)pyrimidin-4-yl)-1H-indazol-5-amine |
| 47 | 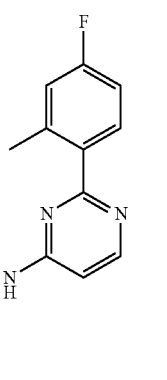 | N-(2-(4-Fluoro-2-methylphenyl)pyrimidin-4-yl)-6,7-dimethoxyquinolin-4-amine |
| 48 | 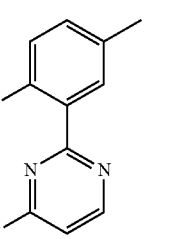 | N-(2-(2-Fluoro-5-methylphenyl)pyrimidin-4-yl)-1H-indazol-5-amine |
| 49 | 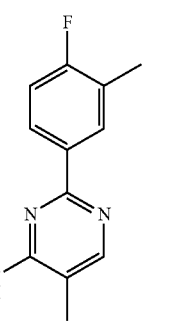 | N-(2-(4-Fluoro-3-methylphenyl)-5-methylpyrimidin-4-yl)-1H-pyrazolo[3,4-b]pyridin-5-amine |

-continued
| No. | Structure | Name |
|---|---|---|
| 50 | 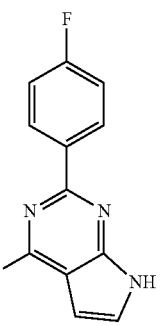 | N-(2-(4-Fluorophenyl)-7H-pyrrolo[2,3-d]pyrimidin-4-yl)-1H-pyrazolo[3,4-b]pyridin-5-amine |
| 51 | 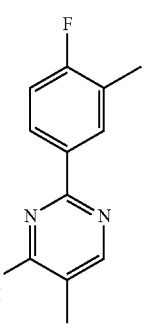 | N-(2-(4-Fluoro-3-methylphenyl)-5-methylpyrimidin-4-yl)-6-methyl-1H-indazol-5-amine |
| 52 | 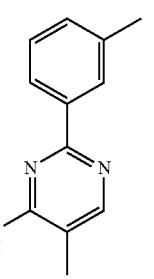 | N-(2-(3-Methylphenyl)-5-methylpyrimidin-4-yl)-6-methyl-1H-indazol-5-amine |
| 53 | 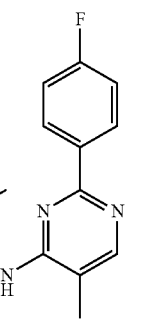 | N-(2-(4-Fluorophenyl)-5-methylpyrimidin-4-yl)-6-methyl-1H-indazol-5-amine |
| 54 | 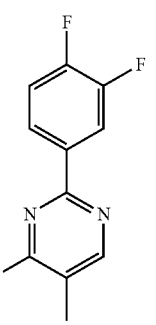 | N-(2-(3,4-Difluorophenyl)-5-methylpyrimidin-4-yl)-6-methyl-1H-indazol-5-amine |

-continued

| No. | Structure | Name |
|---|---|---|
| 55 | 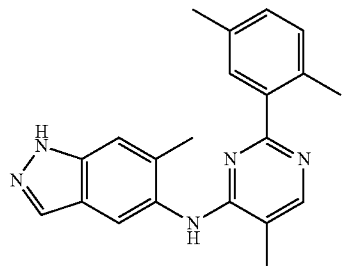 [SMILES: Cc1ccc(C)c(-c2ncc(C)c(Nc3cc4cn[nH]c4cc3C)n2)c1] | N-(2-(2,5-Dimethylphenyl)-5-methylpyrimidin-4-yl)-6-methyl-1H-indazol-5-amine |
| 56 | 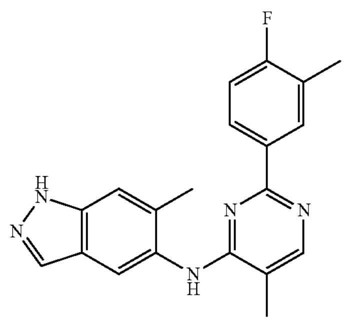 [SMILES: Cc1cc(-c2ncc(C)c(Nc3cc4cn[nH]c4cc3C)n2)ccc1F] | N-(2-(4-Fluoro-3-methylphenyl)-5-methylpyrimidin-4-yl)-6-methyl-1H-indazol-5-amine |
| 57 | 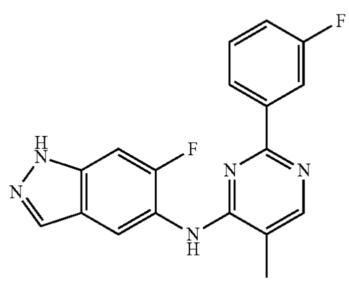 [SMILES: Cc1cnc(-c2cccc(F)c2)nc1Nc1cc2cn[nH]c2cc1F] | 6-Fluoro-N-(2-(3-fluorophenyl)-5-methylpyrimidin-4-yl)-1H-indazol-5-amine |
| 58 | 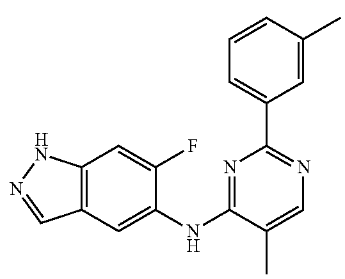 [SMILES: Cc1cccc(-c2ncc(C)c(Nc3cc4cn[nH]c4cc3F)n2)c1] | 6-Fluoro-N-(2-(3-methylphenyl)-5-methylpyrimidin-4-yl)-1H-indazol-5-amine |
| 59 | 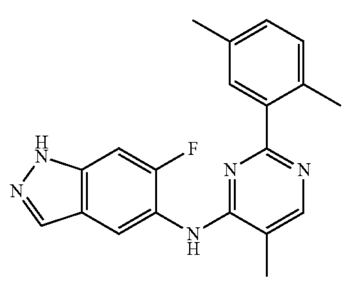 [SMILES: Cc1ccc(C)c(-c2ncc(C)c(Nc3cc4cn[nH]c4cc3F)n2)c1] | 6-Fluoro-N-(2-(2,5-dimethylphenyl)-5-methylpyrimidin-4-yl)-1H-indazol-5-amine |

-continued
| No. | Structure | Name |
|---|---|---|
| 60 | 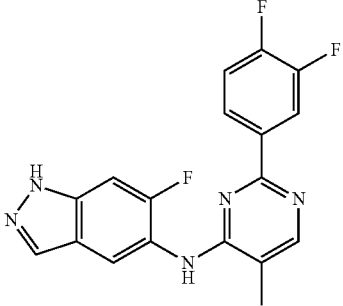 [SMILES: Cc1cnc(-c2ccc(F)c(F)c2)nc1Nc1cc2cn[nH]c2cc1F] | 6-Fluoro-N-(2-(3,4-difluorophenyl)-5-methylpyrimidin-4-yl)-1H-indazol-5-amine |
| 61 | 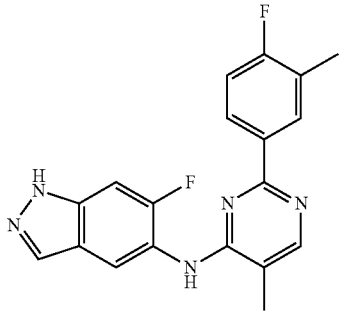 [SMILES: Cc1cc(-c2ncc(C)c(Nc3cc4cn[nH]c4cc3F)n2)ccc1F] | 6-Fluoro-N-(2-(4-fluoro-3-methylphenyl)-5-methylpyrimidin-4-yl)-1H-indazol-5-amine |
| 62 | 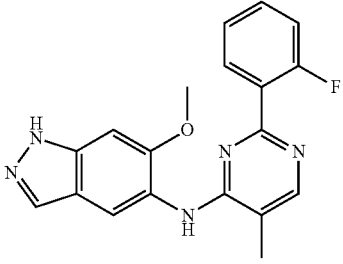 [SMILES: COc1cc2[nH]ncc2cc1Nc1nc(-c2ccccc2F)ncc1C] | N-(2-(2-Fluorophenyl)-5-methylpyrimidin-4-yl)-6-methoxy-1H-indazol-5-amine |
| 63 | 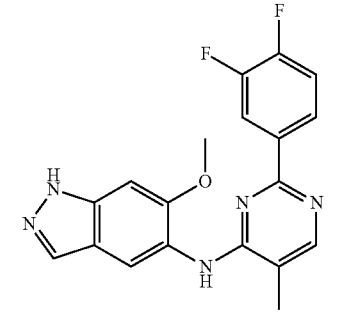 [SMILES: COc1cc2[nH]ncc2cc1Nc1nc(-c2ccc(F)c(F)c2)ncc1C] | N-(2-(3,4-Difluorophenyl)-5-methylpyrimidin-4-yl)-6-methoxy-1H-indazol-5-amine |

In embodiment II₁ of this aspect, the invention comprises compounds having the structure of formula (II):

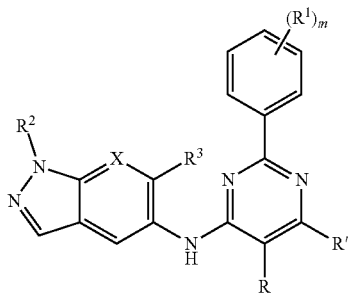

(II)

or a pharmaceutically acceptable salt, prodrug or N-oxide thereof, or solvate or hydrate thereof,
wherein
R and R' are independently hydrogen, halogen, $C_{1-6}$ alkyl or $C_{1-6}$ haloalkyl;
or R and R' taken together with the carbon atoms to which they are attached form a pyrrole;
$R^1$ is halogen, cyano, —$OR^a$, —$SR^a$, —$N(R^a)_2$, $C_{1-6}$ alkyl, $C_{1-6}$haloalkyl or $C_{3-8}$cycloalkyl, wherein each $R^a$ is independently hydrogen, $C_{1-6}$ alkyl or $C_{1-6}$ haloalkyl;
m is 0, 1, 2, 3 or 4;
X is N or C(H);
$R^2$ is hydrogen, —C(O)CH₂N$R^b{}_2$, —CH₂—OP(O)(OR)₂, $C_{1-6}$ alkyl, $C_{1-6}$haloalkyl, $C_{3-8}$cycloalkyl or heteroaryl,
wherein each $R^b$ is independently hydrogen or $C_{1-6}$ alkyl, and
wherein each $R^c$ is independently hydrogen or $C_{1-6}$ alkyl; and
$R^3$ is hydrogen, halogen, $C_{1-6}$alkyl, $C_{1-6}$haloalkyl, cycloalkyl or heteroaryl.

In embodiment II₂ of this aspect, the invention comprises compounds having the structure of formula (IIa):

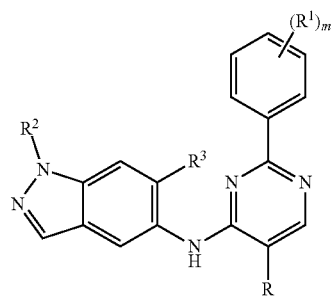

(IIa)

R is hydrogen, halogen, $C_{1-6}$ alkyl or $C_{1-6}$ haloalkyl;
$R^1$ is halogen, cyano, —$OR^a$, $C_{1-6}$ alkyl, —NH₂, $C_{1-6}$ haloalkyl or $C_{3-6}$ cycloalkyl, wherein each $R^a$ is independently hydrogen, $C_{1-6}$ alkyl or $C_{1-6}$ haloalkyl;
m is 0, 1, 2, 3 or 4;
$R^2$ is hydrogen, $C_{1-6}$ alkyl, —C(O)(CH₂)$_s$N$R^b{}_2$, —CH₂—OP(O)(OR)₂, $C_{1-6}$ haloalkyl, $C_{3-6}$ cycloalkyl or $C_{5-6}$ heteroaryl,
wherein each $R^b$ is independently hydrogen or $C_{1-6}$ alkyl, and
wherein each $R^c$ is independently hydrogen or $C_{1-6}$ alkyl; and
$R^3$ is hydrogen, halogen, $C_{1-6}$ alkyl, $C_{1-6}$ haloalkyl, piperidinyl, piperazinyl or morpholinyl.

In embodiment II₃ of this aspect, the invention comprises compounds of embodiment II₂, wherein
R is hydrogen, halogen, $C_{1-6}$ alkyl or $C_{1-6}$ haloalkyl;
$R^1$ is halogen, cyano, —$OR^a$, $C_{1-6}$ alkyl or —NH₂, wherein $R^a$ is $C_{1-6}$ alkyl;
m is 0, 1, 2, 3 or 4;
$R^2$ is hydrogen, $C_{1-6}$ alkyl, —C(O)(CH₂)$_s$N$R^b{}_2$ or —CH₂—OP(O)(OR)₂,
wherein each $R^b$ is independently hydrogen or $C_{1-6}$ alkyl, and
wherein each $R^c$ is independently hydrogen or $C_{1-6}$ alkyl; and
$R^3$ is hydrogen, halogen or $C_{1-6}$ alkyl.

In embodiment II₄ of this aspect, the invention comprises compounds of any of embodiments II₁-II₃, wherein $R^2$ is hydrogen.

In embodiment II₅ of this aspect, the invention comprises compounds of any of embodiments II₁-II₄, wherein $R^3$ is hydrogen.

In embodiment II₆, the compounds of the invention are one of formulae (IIb)-(IIn):

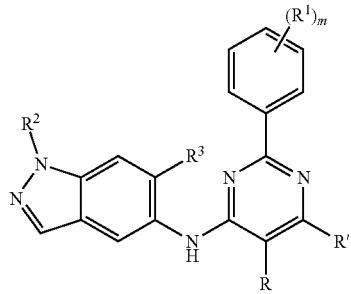

(IIb)

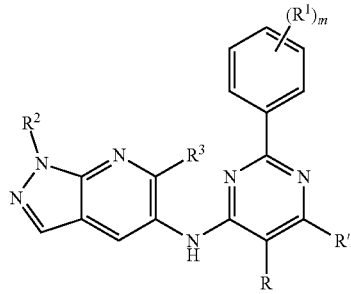

(IIc)

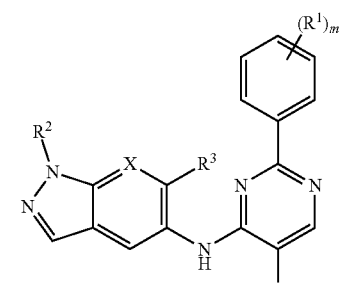

(IId)

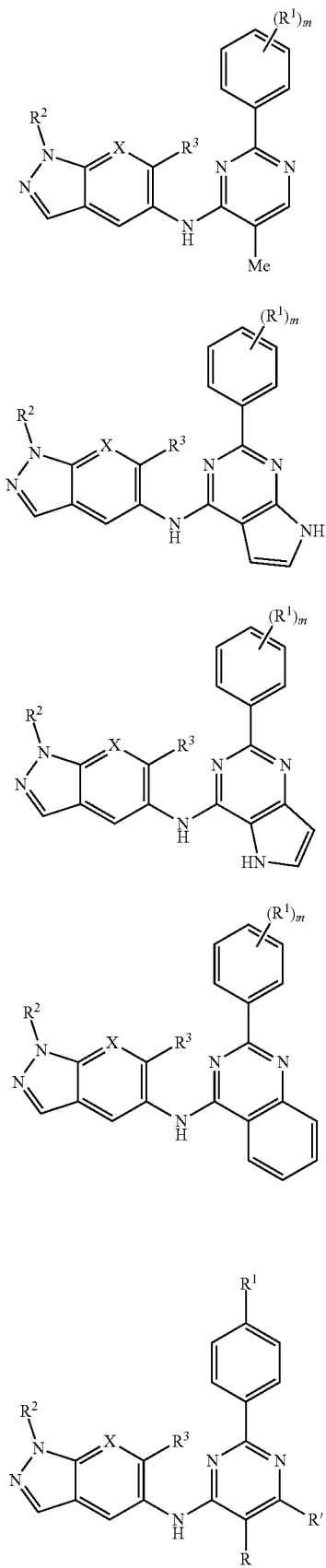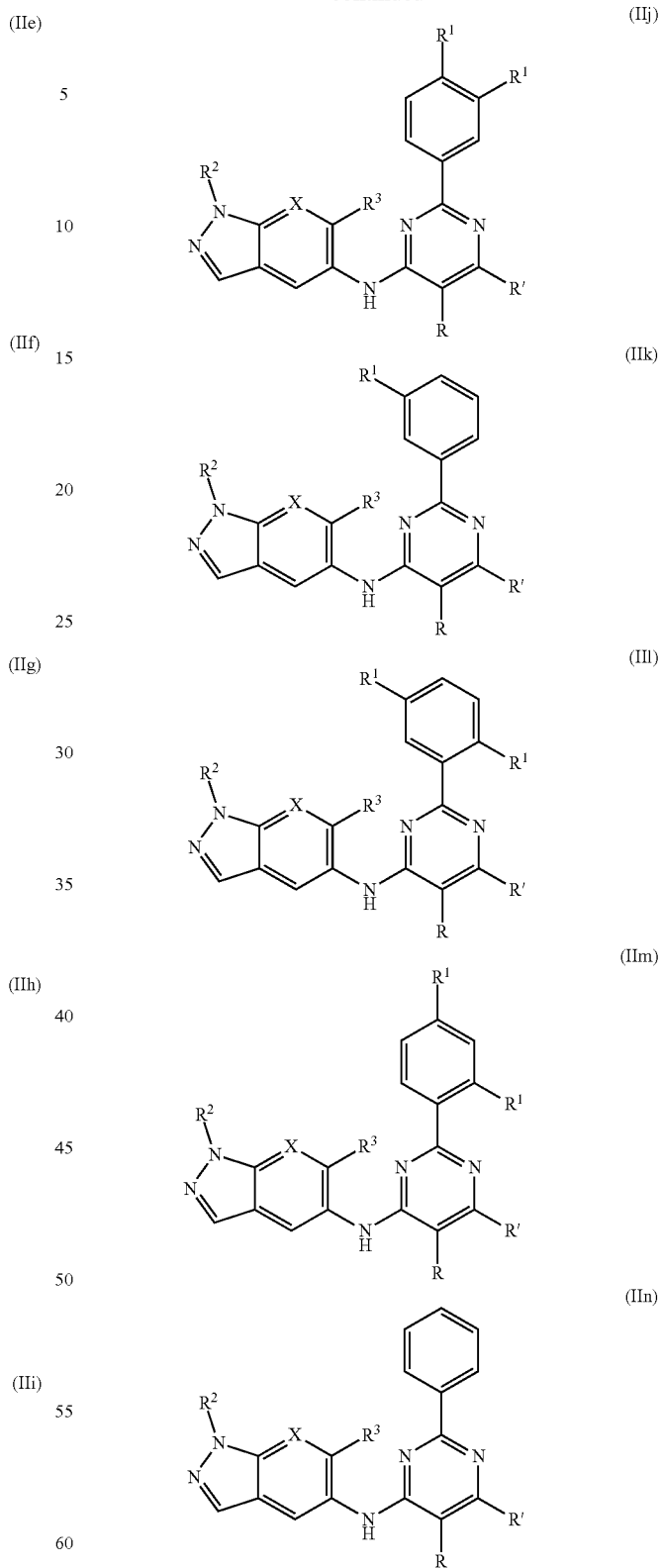
wherein R, R' R¹, R², R³ and X are as defined in embodiments II₁-II₅ above.
Particular embodiments of this aspect of the invention comprise compounds of any one of the formulae (II), and (IIa)-(IIn), each as defined in each of the following rows (or a pharmaceutically acceptable salt, prodrug, or N-oxide thereof, or a solvate or hydrate thereof), wherein each entry is a group number as defined above (e.g., (3gg) refers to R' is hydrogen and $R^1$ is ethyl), an "X" indicates that the variable is defined by another group in the embodiment (e.g., in embodiment (3)-83 below, R/R' is defined in the structure of formula (IIe)) and a dash "-" indicates that the variable is as defined in embodiment $II_1$ or defined according to any one of the applicable variable definitions (1a)-(1mm), (2a)-(2oo) and (3a)-(3ii) [e.g., when A is a dash, it can be either as defined in any of embodiments $II_1$-$II_6$ or any one of the applicable definitions (1a)-(1mm)]:

|  | (II) | A | Z | R/R' |
|---|---|---|---|---|
| (2)-1 | (IIb) | (1a) | (2l) | (3a) |
| (2)-2 | (IIb) | (1b) | (2n) | (3b) |
| (2)-3 | (IIb) | (1c) | (2p) | (3c) |
| (2)-4 | (IIb) | (1d) | (2r) | (3f) |
| (2)-5 | (IIb) | (1f) | (2y) | (3k) |
| (2)-6 | (IIb) | (1n) | (2z) | (3n) |
| (2)-7 | (IIb) | (1r) | (2aa) | (3a) |
| (2)-8 | (IIb) | (1s) | (2dd) | (3b) |
| (2)-9 | (IIb) | (1v) | (2ee) | (3c) |
| (2)-10 | (IIb) | (1x) | (2ff) | (3f) |
| (2)-11 | (IIb) | (1y) | (2ii) | (3k) |
| (2)-12 | (IIb) | (1z) | (2jj) | (3n) |
| (2)-13 | (IIb) | (1ee) | (2ll) | (3s) |
| (2)-14 | (IIb) | (1ff) | (2nn) | (3v) |
| (2)-15 | (IIb) | (1gg) | (2ii) | (3y) |
| (2)-16 | (IIb) | (1ii) | (2jj) | (3aa) |
| (2)-17 | (IIb) | (1jj) | (2ll) | (3ee) |
| (2)-18 | (IIb) | (1kk) | (2nn) | (3c) |
| (2)-19 | (IIb) | (1ll) | (2r) | (3f) |
| (2)-20 | (IIb) | (1mm) | (2y) | (3k) |
| (2)-21 | (IIb) | (1a) | (2z) | (3n) |
| (2)-22 | (IIb) | (1b) | (2aa) | (3s) |
| (2)-23 | (IIb) | (1c) | (2dd) | (3b) |
| (2)-24 | (IIb) | (1d) | (2ee) | (3c) |
| (2)-25 | (IIb) | (1f) | (2ff) | (3a) |
| (2)-26 | (IIc) | (1n) | (2ii) | (3b) |
| (2)-27 | (IIc) | (1r) | (2jj) | (3a) |
| (2)-28 | (IIc) | (1s) | (2y) | (3b) |
| (2)-29 | (IIc) | (1v) | (2z) | (3c) |
| (2)-30 | (IIc) | (1x) | (2aa) | (3f) |
| (2)-31 | (IIc) | (1y) | (2dd) | (3k) |
| (2)-32 | (IIc) | (1z) | (2ee) | (3n) |
| (2)-33 | (IIc) | (1ee) | (2ff) | (3s) |
| (2)-34 | (IIc) | (1ff) | (2ii) | (3v) |
| (2)-35 | (IIc) | (1gg) | (2jj) | (3y) |
| (2)-36 | (IIc) | (1ii) | (2jj) | (3aa) |
| (2)-37 | (IIc) | (1jj) | (2n) | (3ee) |
| (2)-38 | (IIc) | (1kk) | (2p) | (3c) |
| (2)-39 | (IIc) | (1ll) | (2r) | (3f) |
| (2)-40 | (IIc) | (1mm) | (2p) | (3k) |
| (2)-41 | (IIc) | (1a) | (2r) | (3n) |
| (2)-42 | (IIc) | (1b) | (2y) | (3s) |
| (2)-43 | (IIc) | (1c) | (2z) | (3b) |
| (2)-44 | (IIc) | (1d) | (2aa) | (3c) |
| (2)-45 | (IIc) | (1f) | (2dd) | (3a) |
| (2)-46 | (IIc) | (1n) | (2ee) | (3b) |
| (2)-47 | (IIc) | (1r) | (2ff) | (3ee) |
| (2)-48 | (IIc) | (1s) | (2ii) | (3c) |
| (2)-49 | (IIc) | (1v) | (2jj) | (3f) |
| (2)-50 | (IIc) | (1x) | (2ll) | (3k) |
| (2)-51 | (IId) | (1y) | (2nn) | (3y) |
| (2)-52 | (IId) | (1z) | (2ff) | (3z) |
| (2)-53 | (IId) | (1ee) | (2jj) | (3aa) |
| (2)-54 | (IId) | (1ff) | (2n) | (3bb) |
| (2)-55 | (IId) | (1gg) | (2p) | (3ee) |
| (2)-56 | (IId) | (1ii) | (2r) | (3ff) |
| (2)-57 | (IId) | (1jj) | (2ff) | (3ii) |
| (2)-58 | (IId) | (1kk) | (2jj) | (3y) |
| (2)-59 | (IId) | (1ll) | (2n) | (3z) |
| (2)-60 | (IId) | (1mm) | (2p) | (3aa) |
| (2)-61 | (IId) | (1a) | (2r) | (3bb) |
| (2)-62 | (IId) | (1b) | (2n) | (3ee) |
| (2)-63 | (IId) | (1c) | (2p) | (3ff) |
| (2)-64 | (IId) | (1d) | (2r) | (3ii) |
| (2)-65 | (IId) | (1f) | (2y) | (3y) |
| (2)-66 | (IId) | (1n) | (2z) | (3z) |
| (2)-67 | (IId) | (1r) | (2aa) | (3aa) |
| (2)-68 | (IId) | (1s) | (2dd) | (3bb) |
| (2)-69 | (IId) | (1v) | (2ee) | (3ee) |
| (2)-70 | (IId) | (1x) | (2ff) | (3ff) |
| (2)-71 | (IId) | (1y) | (2ii) | (3ii) |
| (2)-72 | (IId) | (1z) | (2jj) | (3y) |
| (2)-73 | (IId) | (1ee) | (2ll) | (3z) |
| (2)-74 | (IId) | (1ff) | (2nn) | (3aa) |
| (2)-75 | (IIe) | (1gg) | (2r) | X |
| (2)-76 | (IIe) | (1ii) | (2y) | X |
| (2)-77 | (IIe) | (1jj) | (2z) | X |
| (2)-78 | (IIe) | (1kk) | (2aa) | X |
| (2)-79 | (IIe) | (1ll) | (2dd) | X |
| (2)-80 | (IIe) | (1mm) | (2ee) | X |
| (2)-81 | (IIe) | (1a) | (2ff) | X |
| (2)-82 | (IIe) | (1b) | (2ii) | X |
| (2)-83 | (IIe) | (1c) | (2jj) | X |
| (2)-84 | (IIe) | (1d) | (2ll) | X |
| (2)-85 | (IIe) | (1f) | (2ff) | X |
| (2)-86 | (IIe) | (1n) | (2jj) | X |
| (2)-87 | (IIe) | (1r) | (2ff) | X |
| (2)-88 | (IIe) | (1s) | (2jj) | X |
| (2)-89 | (IIe) | (1v) | (2p) | X |
| (2)-90 | (IIe) | (1x) | (2r) | X |
| (2)-91 | (IIe) | (1y) | (2y) | X |
| (2)-92 | (IIe) | (1z) | (2n) | X |
| (2)-93 | (IIe) | (1ee) | (2p) | X |
| (2)-94 | (IIe) | (1ff) | (2r) | X |
| (2)-95 | (IIe) | (1gg) | (2y) | X |
| (2)-96 | (IIe) | (1ii) | (2z) | X |
| (2)-97 | (IIe) | (1jj) | (2aa) | X |
| (2)-98 | (IIe) | (1kk) | (2dd) | X |
| (2)-99 | (IIe) | (1ll) | (2ee) | X |
| (2)-100 | (IIe) | (1mm) | (2ff) | X |
| (2)-101 | (IIf) | (1a) | (2ii) | X |
| (2)-102 | (IIf) | (1b) | (2jj) | X |
| (2)-103 | (IIf) | (1c) | (2ll) | X |
| (2)-104 | (IIf) | (1d) | (2nn) | X |
| (2)-105 | (IIf) | (1f) | (2ff) | X |
| (2)-106 | (IIf) | (1n) | (2jj) | X |
| (2)-107 | (IIf) | (1r) | (2p) | X |
| (2)-108 | (IIf) | (1s) | (2r) | X |
| (2)-109 | (IIf) | (1v) | (2y) | X |
| (2)-110 | (IIf) | (1x) | (2jj) | X |
| (2)-111 | (IIf) | (1y) | (2n) | X |
| (2)-112 | (IIf) | (1z) | (2p) | X |
| (2)-113 | (IIf) | (1ee) | (2r) | X |
| (2)-114 | (IIf) | (1ff) | (2p) | X |
| (2)-115 | (IIf) | (1gg) | (2r) | X |
| (2)-116 | (IIf) | (1ii) | (2y) | X |
| (2)-117 | (IIf) | (1jj) | (2z) | X |
| (2)-118 | (IIf) | (1kk) | (2aa) | X |
| (2)-119 | (IIf) | (1ll) | (2dd) | X |
| (2)-120 | (IIf) | (1mm) | (2ee) | X |
| (2)-121 | (IIg) | (1a) | (2ff) | X |
| (2)-122 | (IIg) | (1b) | (2ii) | X |
| (2)-123 | (IIg) | (1c) | (2jj) | X |
| (2)-124 | (IIg) | (1d) | (2ll) | X |
| (2)-125 | (IIg) | (1f) | (2nn) | X |
| (2)-126 | (IIg) | (1n) | (2ff) | X |
| (2)-127 | (IIg) | (1r) | (2jj) | X |
| (2)-128 | (IIg) | (1s) | (2l) | X |
| (2)-129 | (IIg) | (1v) | (2n) | X |
| (2)-130 | (IIg) | (1x) | (2p) | X |
| (2)-131 | (IIg) | (1y) | (2r) | X |
| (2)-132 | (IIg) | (1z) | (2y) | X |
| (2)-133 | (IIg) | (1ee) | (2z) | X |
| (2)-134 | (IIg) | (1ff) | (2aa) | X |
| (2)-135 | (IIg) | (1gg) | (2dd) | X |
| (2)-136 | (IIg) | (1ii) | (2ee) | X |
| (2)-137 | (IIg) | (1jj) | (2ff) | X |
| (2)-138 | (IIg) | (1kk) | (2ii) | X |
| (2)-139 | (IIg) | (1ll) | (2jj) | X |
| (2)-140 | (IIg) | (1mm) | (2ll) | X |

-continued

|  | (II) | A | Z | R/R' |
|---|---|---|---|---|
| (2)-141 | (IIh) | (1a) | (2nn) | X |
| (2)-142 | (IIh) | (1b) | (2ff) | X |
| (2)-143 | (IIh) | (1c) | (2ii) | X |
| (2)-144 | (IIh) | (1d) | (2jj) | X |
| (2)-145 | (IIh) | (1f) | (2r) | X |
| (2)-146 | (IIh) | (1n) | (2y) | X |
| (2)-147 | (IIh) | (1r) | (2z) | X |
| (2)-148 | (IIh) | (1s) | (2n) | X |
| (2)-149 | (IIh) | (1v) | (2p) | X |
| (2)-150 | (IIh) | (1x) | (2r) | X |
| (2)-151 | (IIi) | (1y) | (2y) | (3b) |
| (2)-152 | (IIi) | (1z) | (2z) | (3ee) |
| (2)-153 | (IIi) | (1ee) | (2n) | (3b) |
| (2)-154 | (IIi) | (1ff) | (2p) | (3c) |
| (2)-155 | (IIi) | (1gg) | (2r) | (3f) |
| (2)-156 | (IIi) | (1ii) | (2y) | (3k) |
| (2)-157 | (IIi) | (1jj) | (2z) | (3n) |
| (2)-158 | (IIi) | (1kk) | (2aa) | (3s) |
| (2)-159 | (IIi) | (1ll) | (2dd) | (3v) |
| (2)-160 | (IIi) | (1ll) | (2ee) | (3y) |
| (2)-161 | (IIi) | (1a) | (2ff) | (3aa) |
| (2)-162 | (IIi) | (1b) | (2ii) | (3ee) |
| (2)-163 | (IIi) | (1c) | (2jj) | (3c) |
| (2)-164 | (IIi) | (1d) | (2ll) | (3f) |
| (2)-165 | (IIi) | (1f) | (2nn) | (3k) |
| (2)-166 | (IIi) | (1n) | (2p) | (3n) |
| (2)-167 | (IIi) | (1r) | (2r) | (3s) |
| (2)-168 | (IIi) | (1s) | (2y) | (3b) |
| (2)-169 | (IIi) | (1v) | (2n) | (3c) |
| (2)-170 | (IIi) | (1x) | (2p) | (3v) |
| (2)-171 | (IIi) | (1y) | (2r) | (3y) |
| (2)-172 | (IIi) | (1z) | (2y) | (3aa) |
| (2)-173 | (IIi) | (1ee) | (2z) | (3ee) |
| (2)-174 | (IIi) | (1ff) |  | (3b) |
| (2)-175 | (IIi) | (1gg) | (2l) | (3c) |
| (2)-176 | (IIj) | (1ii) | (2n) | (3f) |
| (2)-177 | (IIj) | (1jj) | (2p) | (3k) |
| (2)-178 | (IIj) | (1kk) | (2r) | (3n) |
| (2)-179 | (IIj) | (1kk) | (2y) | (3s) |
| (2)-180 | (IIj) | (1kk) | (2z) | (3v) |
| (2)-181 | (IIj) | (1a) | (2aa) | (3y) |
| (2)-182 | (IIj) | (1b) | (2dd) | (3aa) |
| (2)-183 | (IIj) | (1c) | (2ee) | (3ee) |
| (2)-184 | (IIj) | (1d) | (2ff) | (3c) |
| (2)-185 | (IIj) | (1f) | (2ii) | (3f) |
| (2)-186 | (IIj) | (1n) | (2jj) | (3k) |
| (2)-187 | (IIj) | (1r) | (2ll) | (3n) |
| (2)-188 | (IIj) | (1s) | (2nn) | (3s) |
| (2)-189 | (IIj) | (1v) | (2ff) | (3c) |
| (2)-190 | (IIj) | (1x) | (2ii) | (3f) |
| (2)-191 | (IIj) | (1y) | (2jj) | (3k) |
| (2)-192 | (IIj) | (1z) | (2p) | (3n) |
| (2)-193 | (IIj) | (1ee) | (2r) | (3s) |
| (2)-194 | (IIj) | (1ff) | (2y) | (3v) |
| (2)-195 | (IIj) | (1gg) | (2z) | (3y) |
| (2)-196 | (IIj) | (1ii) | (2ff) | (3aa) |
| (2)-197 | (IIj) | (1jj) | (2jj) | (3ee) |
| (2)-198 | (IIj) | (1kk) | (2jj) | (3s) |
| (2)-199 | (IIj) | (1kk) | (2l) | (3v) |
| (2)-200 | (IIj) | (1kk) | (2n) | (3y) |
| (2)-201 | (IIk) | (1a) | (2p) | (3aa) |
| (2)-202 | (IIk) | (1b) | (2r) | (3ee) |
| (2)-203 | (IIk) | (1c) | (2y) | (3c) |
| (2)-204 | (IIk) | (1d) | (2z) | (3f) |
| (2)-205 | (IIk) | (1f) | (2aa) | (3k) |
| (2)-206 | (IIk) | (1n) | (2dd) | (3n) |
| (2)-207 | (IIk) | (1r) | (2ee) | (3s) |
| (2)-208 | (IIk) | (1s) | (2ff) | (3b) |
| (2)-209 | (IIk) | (1v) | (2ii) | (3c) |
| (2)-210 | (IIk) | (1x) | (2jj) | (3f) |
| (2)-211 | (IIk) | (1y) | (2ll) | (3k) |
| (2)-212 | (IIk) | (lz) | (2nn) | (3n) |
| (2)-213 | (IIk) | (1ee) | (2ff) | (3s) |
| (2)-214 | (IIk) | (1ff) | (2ii) | (3v) |
| (2)-215 | (IIk) | (1gg) | (2jj) | (3y) |
| (2)-216 | (IIk) | (1ii) | (2p) | (3aa) |
| (2)-217 | (IIk) | (1jj) | (2r) | (3ee) |
| (2)-218 | (IIk) | (1kk) | (2y) | (3b) |
| (2)-219 | (IIk) | (1ll) | (2z) | (3c) |
| (2)-220 | (IIk) | (1ll) | (2ff) | (3f) |
| (2)-221 | (IIk) | (1a) | (2ii) | (3k) |
| (2)-222 | (IIk) | (1b) | (2jj) | (3n) |
| (2)-223 | (IIk) | (1c) | (2r) | (3s) |
| (2)-224 | (IIk) | (1d) | (2y) | (3v) |
| (2)-225 | (IIk) | (1f) | (2z) | (3y) |
| (2)-226 | (III) | (1n) | (2n) | (3aa) |
| (2)-227 | (III) | (1r) | (2p) | (3ee) |
| (2)-228 | (III) | (1s) | (2r) | (3f) |
| (2)-229 | (III) | (1v) | (2y) | (3k) |
| (2)-230 | (III) | (1x) | (2z) | (3n) |
| (2)-231 | (III) | (1y) | (2aa) | (3s) |
| (2)-232 | (III) | (1z) | (2dd) | (3a) |
| (2)-233 | (III) | (1ee) | (2ee) | (3b) |
| (2)-234 | (III) | (1ff) | (2ff) | (3c) |
| (2)-235 | (III) | (1gg) | (2ii) | (3f) |
| (2)-236 | (III) | (1ii) | (2jj) | (3k) |
| (2)-237 | (III) | (1jj) | (2ll) | (3n) |
| (2)-238 | (III) | (1kk) | (2nn) | (3s) |
| (2)-239 | (III) | (1kk) | (2ff) | (3v) |
| (2)-240 | (III) | (1kk) | (2ii) | (3c) |
| (2)-241 | (III) | (1a) | (2jj) | (3v) |
| (2)-242 | (III) | (1b) | (2r) | (3y) |
| (2)-243 | (III) | (1c) | (2y) | (3aa) |
| (2)-244 | (III) | (1d) | (2z) | (3ee) |
| (2)-245 | (III) | (1f) | (2ff) | (3b) |
| (2)-246 | (III) | (1n) | (2ii) | (3c) |
| (2)-247 | (III) | (1r) | (2jj) | (3f) |
| (2)-248 | (III) | (1s) | (2l) | (3k) |
| (2)-249 | (III) | (1v) | (2n) | (3n) |
| (2)-250 | (III) | (1x) | (2p) | (3s) |
| (2)-251 | (IIm) | (1y) | (2r) | (3v) |
| (2)-252 | (IIm) | (1z) | (2y) | (3y) |
| (2)-253 | (IIm) | (1ee) | (2z) | (3aa) |
| (2)-254 | (IIm) | (1ff) | (2aa) | (3ee) |
| (2)-255 | (IIm) | (1gg) | (2dd) | (3f) |
| (2)-256 | (IIm) | (1ii) | (2ee) | (3k) |
| (2)-257 | (IIm) | (1jj) | (2ff) | (3n) |
| (2)-258 | (IIm) | (1kk) | (2ii) | (3c) |
| (2)-259 | (IIm) | (1kk) | (2jj) | (3f) |
| (2)-260 | (IIm) | (1kk) | (2ll) | (3k) |
| (2)-261 | (IIm) | (1a) | (2nn) | (3n) |
| (2)-262 | (IIm) | (1b) | (2p) | (3s) |
| (2)-263 | (IIm) | (1c) | (2r) | (3c) |
| (2)-264 | (IIm) | (1d) | (2y) | (3v) |
| (2)-265 | (IIm) | (1f) | (2p) | (3y) |
| (2)-266 | (IIm) | (1n) | (2r) | (3aa) |
| (2)-267 | (IIm) | (1r) | (2y) | (3ee) |
| (2)-268 | (IIm) | (1s) | (2z) | (3b) |
| (2)-269 | (IIm) | (1v) | (2l) | (3a) |
| (2)-270 | (IIm) | (1x) | (2n) | (3b) |
| (2)-271 | (IIm) | (1y) | (2p) | (3c) |
| (2)-272 | (IIm) | (1z) | (2r) | (3f) |
| (2)-273 | (IIm) | (1ee) | (2y) | (3k) |
| (2)-274 | (IIm) | (1ff) | (2z) | (3n) |
| (2)-275 | (IIm) | (1gg) | (2aa) | (3s) |
| (2)-276 | (IIn) | X | (2dd) | (3v) |
| (2)-277 | (IIn) | X | (2ee) | (3y) |
| (2)-278 | (IIn) | X | (2ff) | (3aa) |
| (2)-279 | (IIn) | X | (2ii) | (3ee) |
| (2)-280 | (IIn) | X | (2jj) | (3f) |
| (2)-281 | (IIn) | X | (2ll) | (3k) |
| (2)-282 | (IIn) | X | (2nn) | (3n) |
| (2)-283 | (IIn) | X | (2ff) | (3s) |
| (2)-284 | (IIn) | X | (2ii) | (3f) |
| (2)-285 | (IIn) | X | (2jj) | (3k) |
| (2)-286 | (IIn) | X | (2r) | (3n) |
| (2)-287 | (IIn) | X | (2y) | (3a) |
| (2)-288 | (IIn) | X | (2z) | (3b) |
| (2)-289 | (IIn) | X | (2n) | (3c) |
| (2)-290 | (IIn) | X | (2p) | (3f) |
| (2)-291 | (IIn) | X | (2r) | (3k) |
| (2)-292 | (IIn) | X | (2y) | (3n) |
| (2)-293 | (IIn) | X | (2z) | (3s) |
| (2)-294 | (IIn) | X | (2ff) | (3v) |

| | (II) | A | Z | R/R' |
|---|---|---|---|---|
| (2)-295 | (IIn) | X | (2ii) | (3y) |
| (2)-296 | (IIn) | X | (2jj) | (3aa) |
| (2)-297 | (IIn) | X | (2p) | (3a) |
| (2)-298 | (IIn) | X | (2r) | (3a) |
| (2)-299 | (IIn) | X | (2y) | (3b) |
| (2)-300 | (IIn) | X | (2z) | (3c) |

In embodiment III$_1$ of this aspect, the invention comprises compounds having the structure of formula (III):

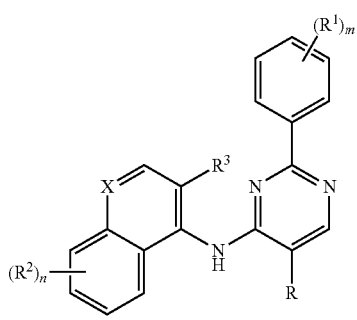

(III)

or a pharmaceutically acceptable salt, prodrug or N-oxide thereof, or solvate or hydrate thereof, wherein R is hydrogen, halogen, C$_{1-6}$alkyl or C$_{1-6}$ haloalkyl;

R$^1$ is halogen, —OR$^a$, C$_{1-6}$ alkyl or C$_{1-6}$haloalkyl,
  wherein each R$^a$ is independently hydrogen, C$_{1-6}$ alkyl or C$_{1-6}$ haloalkyl;

m is 0, 1, 2, 3 or 4;

X is N or C(H);

R$^2$ is hydrogen, —OR$^b$, C$_{1-6}$ alkyl or C$_{1-6}$haloalkyl,
  wherein R$^b$ is hydrogen, C$_{1-6}$ alkyl or C$_{1-6}$ haloalkyl;

n is 0, 1, 2, 3 or 4; and

R$^3$ is hydrogen, halogen, C$_{1-6}$alkyl or C$_{1-6}$haloalkyl.

In embodiment III$_2$, the compounds of the invention are of embodiment III$_1$, wherein R is hydrogen.

In embodiment III$_3$, the compounds of the invention are of embodiments III$_1$ or III$_2$, wherein R$^1$ is halogen or C$_{1-6}$ alkyl, and m is 0, 1 or 2.

In embodiment III$_4$, the compounds of the invention are of any one of embodiments III$_1$-III$_3$, wherein X is N.

In embodiment III$_5$, the compounds of the invention are of any one of embodiments III$_1$-III$_4$, wherein
  R$^2$ is hydrogen or —OR$^b$,
    wherein R$^b$ is hydrogen or C$_{1-6}$ alkyl; and
  n is 0, 1 or 2.

In embodiment III$_6$, the compounds of the invention are of any one of embodiments III$_1$-III$_4$, wherein R$^2$ is —OMe, and n is 2.

In embodiment III$_7$, the compounds of the invention are of any one of embodiments III$_1$-III$_6$, wherein R$^3$ is hydrogen.

In embodiment III$_8$, the compounds of the invention are of any one of embodiments III$_1$-III$_6$, wherein R$^3$ is C$_{1-6}$alkyl.

In embodiment IV$_1$ of this aspect, the invention comprises compounds having the structure of formula (IV):

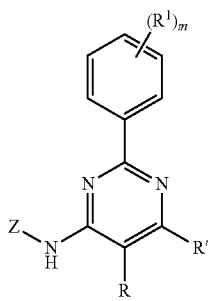

(IV)

or a pharmaceutically acceptable salt, prodrug or N-oxide thereof, or solvate or hydrate thereof, wherein Z is:

a)

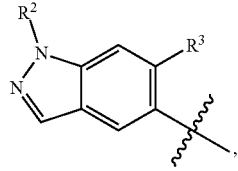

wherein

R$^2$ is hydrogen or —C(O)CH$_2$NR$^b$$_2$,
  wherein R$^b$ is C$_{1-6}$ alkyl; and R$^3$ is hydrogen or C$_{1-6}$alkyl; or b)

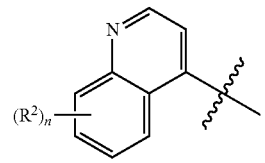

wherein

R$^2$ is hydrogen or —OR$^b$,
  wherein R$^b$ is hydrogen or C$_{1-6}$ alkyl; and n is 0, 1 or 2;

R and R' are independently hydrogen or C$_{1-6}$alkyl;

or R and R' when taken together with the carbon atoms to which they are attached, form a pyrrole;

R$^1$ is halogen, cyano, —OR$^a$, or C$_{1-6}$ alkyl,
  wherein each R$^a$ is independently hydrogen or C$_{1-6}$ alkyl; and m is 0, 1 or 2.

In embodiment IV$_2$, the compounds of the invention are of one of formulae (IVa)-(IVj):

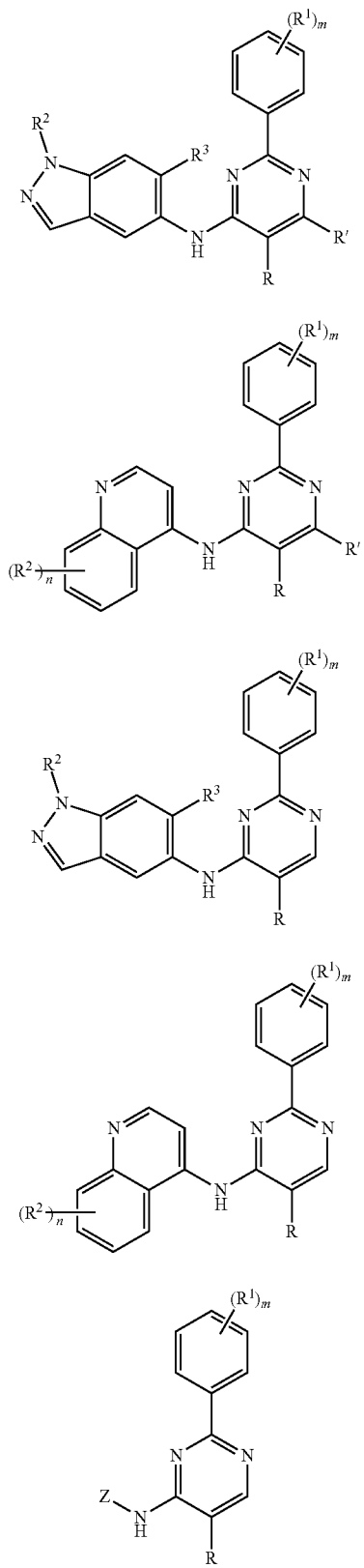

(IVa)
(IVb)
(IVc)
(IVd)
(IVe)

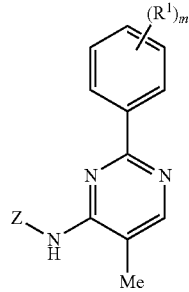

(IVf)

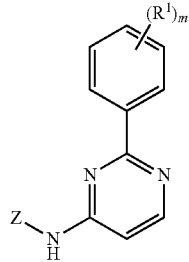

(IVg)

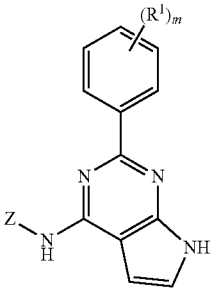

(IVh)

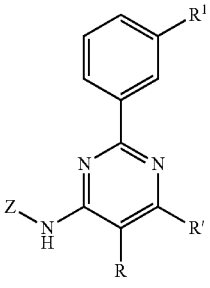

(IVi)

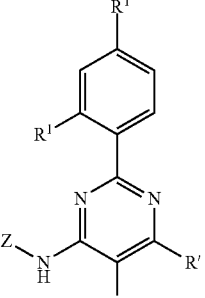

(IVj)

Particular embodiments of this aspect of the invention comprise compounds of any one of the formulae (IV), and (IVa)-(IVj), each as defined in each of the following rows (or a pharmaceutically acceptable salt, prodrug, or N-oxide thereof, or a solvate or hydrate thereof), wherein each entry is a group number as defined above (e.g., (3gg) refers to R' is hydrogen and $R^1$ is ethyl), an "X" indicates that the variable is defined by another group in the embodiment (e.g., in embodiment (3)-103 below, R/R' is defined in the structure of formula (IVf)) and a dash "-" indicates that the variable is as defined in embodiment $I_1$ or defined according to any one of the applicable variable definitions (1a)-(1mm), (2a)-(2oo) and (3a)-(3ii) [e.g., when A is a dash, it can be either as defined in embodiment $IV_1$ or $IV_2$, or any one of the applicable definitions (1a)-(1mm)]:

|        | (IV)  | A      | Z     | R/R'  |
|--------|-------|--------|-------|-------|
| (3)-1  | (IVa) | (1a)   | (2l)  |       |
| (3)-2  | (IVa) | (1b)   | (2n)  | (3a)  |
| (3)-3  | (IVa) | (1c)   | (2p)  | (3b)  |
| (3)-4  | (IVa) | (1d)   | (2r)  | (3c)  |
| (3)-5  | (IVa) | (1f)   | (2y)  | (3f)  |
| (3)-6  | (IVa) | (1n)   | (2z)  | (3k)  |
| (3)-7  | (IVa) | (1r)   | (2aa) | (3n)  |
| (3)-8  | (IVa) | (1s)   | (2dd) | (3a)  |
| (3)-9  | (IVa) | (1v)   | (2ee) | (3b)  |
| (3)-10 | (IVa) | (1x)   | (2ff) | (3c)  |
| (3)-11 | (IVa) | (1y)   | (2ii) | (3f)  |
| (3)-12 | (IVa) | (1z)   | (2jj) | (3k)  |
| (3)-13 | (IVa) | (1ee)  | (2ll) | (3n)  |
| (3)-14 | (IVa) | (1ff)  | (2nn) | (3s)  |
| (3)-15 | (IVa) | (1gg)  | (2ii) | (3v)  |
| (3)-16 | (IVa) | (1ii)  | (2jj) | (3y)  |
| (3)-17 | (IVa) | (1jj)  | (2ll) | (3aa) |
| (3)-18 | (IVa) | (1kk)  | (2nn) | (3ee) |
| (3)-19 | (IVa) | (1ll)  | (2r)  | (3c)  |
| (3)-20 | (IVa) | (1mm)  | (2y)  | (3f)  |
| (3)-21 | (IVb) | (1a)   | (2l)  | (3k)  |
| (3)-22 | (IVb) | (1b)   | (2m)  | (3n)  |
| (3)-23 | (IVb) | (1c)   | (2n)  | (3s)  |
| (3)-24 | (IVb) | (1d)   | (2o)  | (3b)  |
| (3)-25 | (IVb) | (1f)   | (2p)  | (3c)  |
| (3)-26 | (IVb) | (1n)   | (2q)  | (3a)  |
| (3)-27 | (IVb) | (1r)   | (2r)  | (3b)  |
| (3)-28 | (IVb) | (1s)   | (2l)  | (3a)  |
| (3)-29 | (IVb) | (1v)   | (2m)  | (3b)  |
| (3)-30 | (IVb) | (1x)   | (2n)  | (3c)  |
| (3)-31 | (IVb) | (1y)   | (2o)  | (3f)  |
| (3)-32 | (IVb) | (1z)   | (2p)  | (3k)  |
| (3)-33 | (IVb) | (1ee)  | (2q)  | (3n)  |
| (3)-34 | (IVb) | (1ff)  | (2l)  | (3s)  |
| (3)-35 | (IVb) | (1gg)  | (2m)  | (3v)  |
| (3)-36 | (IVb) | (1ii)  | (2n)  | (3y)  |
| (3)-37 | (IVb) | (1jj)  | (2o)  | (3aa) |
| (3)-38 | (IVb) | (1kk)  | (2p)  | (3ee) |
| (3)-39 | (IVb) | (1ll)  | (2q)  | (3c)  |
| (3)-40 | (IVb) | (1mm)  | (2r)  | (3f)  |
| (3)-41 | (IVc) | (1a)   | (2r)  | (3k)  |
| (3)-42 | (IVc) | (1b)   | (2y)  | (3z)  |
| (3)-43 | (IVc) | (1c)   | (2z)  | (3aa) |
| (3)-44 | (IVc) | (1d)   | (2aa) | (3bb) |
| (3)-45 | (IVc) | (1f)   | (2dd) | (3ee) |
| (3)-46 | (IVc) | (1n)   | (2ee) | (3ff) |
| (3)-47 | (IVc) | (1r)   | (2ff) | (3ii) |
| (3)-48 | (IVc) | (1s)   | (2ii) | (3y)  |
| (3)-49 | (IVc) | (1v)   | (2jj) | (3z)  |
| (3)-50 | (IVc) | (1x)   | (2ll) | (3aa) |
| (3)-51 | (IVc) | (1y)   | (2nn) | (3bb) |
| (3)-52 | (IVc) | (1z)   | (2ff) | (3ee) |
| (3)-53 | (IVc) | (1ee)  | (2jj) | (3ff) |
| (3)-54 | (IVc) | (1ff)  | (2n)  | (3ii) |
| (3)-55 | (IVc) | (1gg)  | (2p)  | (3y)  |
| (3)-56 | (IVc) | (1ii)  | (2r)  | (3z)  |
| (3)-57 | (IVc) | (1jj)  | (2ff) | (3aa) |
| (3)-58 | (IVc) | (1kk)  | (2jj) | (3bb) |
| (3)-59 | (IVc) | (1ll)  | (2n)  | (3ee) |
| (3)-60 | (IVc) | (1mm)  | (2p)  | (3ff) |
| (3)-61 | (IVd) | (1a)   | (2l)  | (3ii) |
| (3)-62 | (IVd) | (1b)   | (2m)  | (3y)  |
| (3)-63 | (IVd) | (1c)   | (2n)  | (3z)  |
| (3)-64 | (IVd) | (1d)   | (2o)  | (3aa) |
| (3)-65 | (IVd) | (1f)   | (2p)  | (3y)  |
| (3)-66 | (IVd) | (1n)   | (2q)  | (3z)  |
| (3)-67 | (IVd) | (1r)   | (2r)  | (3aa) |
| (3)-68 | (IVd) | (1s)   | (2l)  | (3bb) |
| (3)-69 | (IVd) | (1v)   | (2m)  | (3ee) |
| (3)-70 | (IVd) | (1x)   | (2n)  | (3ff) |
| (3)-71 | (IVd) | (1y)   | (2o)  | (3ii) |
| (3)-72 | (IVd) | (1z)   | (2p)  | (3y)  |
| (3)-73 | (IVd) | (1ee)  | (2q)  | (3z)  |
| (3)-74 | (IVd) | (1ff)  | (2l)  | (3aa) |
| (3)-75 | (IVd) | (1gg)  | (2m)  | (3bb) |
| (3)-76 | (IVd) | (1ii)  | (2n)  | (3ee) |
| (3)-77 | (IVd) | (1jj)  | (2o)  | (3ff) |
| (3)-78 | (IVd) | (1kk)  | (2p)  | (3ii) |
| (3)-79 | (IVd) | (1ll)  | (2q)  | (3y)  |
| (3)-80 | (IVd) | (1mm)  | (2r)  | (3z)  |
| (3)-81 | (IVe) | (1a)   | (2ff) | (3aa) |
| (3)-82 | (IVe) | (1b)   | (2ii) | (3bb) |
| (3)-83 | (IVe) | (1c)   | (2jj) | (3ee) |
| (3)-84 | (IVe) | (1d)   | (2ll) | (3ff) |
| (3)-85 | (IVe) | (1f)   | (2ff) | (3ii) |
| (3)-86 | (IVe) | (1n)   | (2jj) | (3y)  |
| (3)-87 | (IVe) | (1r)   | (2ff) | (3z)  |
| (3)-88 | (IVe) | (1s)   | (2jj) | (3aa) |
| (3)-89 | (IVe) | (1v)   | (2p)  | (3y)  |
| (3)-90 | (IVe) | (1x)   | (2r)  | (3z)  |
| (3)-91 | (IVe) | (1y)   | (2y)  | (3aa) |
| (3)-92 | (IVe) | (1z)   | (2n)  | (3bb) |
| (3)-93 | (IVe) | (1ee)  | (2p)  | (3ee) |
| (3)-94 | (IVe) | (1ff)  | (2r)  | (3ff) |
| (3)-95 | (IVe) | (1gg)  | (2y)  | (3ii) |
| (3)-96 | (IVe) | (1ii)  | (2z)  | (3y)  |
| (3)-97 | (IVe) | (1jj)  | (2aa) | (3z)  |
| (3)-98 | (IVe) | (1kk)  | (2dd) | (3aa) |
| (3)-99 | (IVe) | (1ll)  | (2ee) | (3bb) |
| (3)-100| (IVe) | (1mm)  | (2ff) | (3ee) |
| (3)-101| (IVf) | (1a)   | (2ii) | X     |
| (3)-102| (IVf) | (1b)   | (2jj) | X     |
| (3)-103| (IVf) | (1c)   | (2ll) | X     |
| (3)-104| (IVf) | (1d)   | (2nn) | X     |
| (3)-105| (IVf) | (1f)   | (2ff) | X     |
| (3)-106| (IVf) | (1n)   | (2jj) | X     |
| (3)-107| (IVf) | (1r)   | (2p)  | X     |
| (3)-108| (IVf) | (1s)   | (2r)  | X     |
| (3)-109| (IVf) | (1v)   | (2y)  | X     |
| (3)-110| (IVf) | (1x)   | (2jj) | X     |
| (3)-111| (IVf) | (1y)   | (2n)  | X     |
| (3)-112| (IVf) | (1z)   | (2p)  | X     |
| (3)-113| (IVf) | (1ee)  | (2r)  | X     |
| (3)-114| (IVf) | (1ff)  | (2p)  | X     |
| (3)-115| (IVf) | (1gg)  | (2r)  | X     |
| (3)-116| (IVf) | (1ii)  | (2y)  | X     |
| (3)-117| (IVf) | (1jj)  | (2z)  | X     |
| (3)-118| (IVf) | (1kk)  | (2aa) | X     |
| (3)-119| (IVf) | (1ll)  | (2dd) | X     |
| (3)-120| (IVf) | (1mm)  | (2ee) | X     |
| (3)-121| (IVg) | (1a)   | (2r)  | X     |
| (3)-122| (IVg) | (1b)   | (2y)  | X     |
| (3)-123| (IVg) | (1c)   | (2z)  | X     |
| (3)-124| (IVg) | (1d)   | (2aa) | X     |
| (3)-125| (IVg) | (1f)   | (2dd) | X     |
| (3)-126| (IVg) | (1n)   | (2ee) | X     |
| (3)-127| (IVg) | (1r)   | (2ff) | X     |
| (3)-128| (IVg) | (1s)   | (2ii) | X     |
| (3)-129| (IVg) | (1v)   | (2jj) | X     |
| (3)-130| (IVg) | (1x)   | (2ll) | X     |
| (3)-131| (IVg) | (1y)   | (2nn) | X     |
| (3)-132| (IVg) | (1z)   | (2ff) | X     |
| (3)-133| (IVg) | (1ee)  | (2jj) | X     |
| (3)-134| (IVg) | (1ff)  | (2n)  | X     |
| (3)-135| (IVg) | (1gg)  | (2p)  | X     |
| (3)-136| (IVg) | (1ii)  | (2r)  | X     |
| (3)-137| (IVg) | (1jj)  | (2ff) | X     |
| (3)-138| (IVg) | (1jj)  | (2jj) | X     |
| (3)-139| (IVg) | (1kk)  | (2n)  | X     |
| (3)-140| (IVg) | (1ll)  | (2p)  | X     |
| (3)-141| (IVh) | (1mm)  | (2r)  | X     |
| (3)-142| (IVh) | (1a)   | (2n)  | X     |
| (3)-143| (IVh) | (1b)   | (2p)  | X     |
| (3)-144| (IVh) | (1c)   | (2r)  | X     |

-continued

|   | (IV) | A | Z | R/R' |
|---|---|---|---|---|
| (3)-145 | (IVh) | (1d) | (2y) | X |
| (3)-146 | (IVh) | (1f) | (2z) | X |
| (3)-147 | (IVh) | (1n) | (2aa) | X |
| (3)-148 | (IVh) | (1r) | (2dd) | X |
| (3)-149 | (IVh) | (1s) | (2ee) | X |
| (3)-150 | (IVh) | (1v) | (2ff) | X |
| (3)-151 | (IVh) | (1x) | (2ii) | X |
| (3)-152 | (IVh) | (1y) | (2jj) | X |
| (3)-153 | (IVh) | (1z) | (2ll) | X |
| (3)-154 | (IVh) | (1ee) | (2nn) | X |
| (3)-155 | (IVh) | (1ff) | (2r) | X |
| (3)-156 | (IVh) | (1gg) | (2y) | X |
| (3)-157 | (IVh) | (1ii) | (2z) | X |
| (3)-158 | (IVh) | (1n) | (2aa) | X |
| (3)-159 | (IVh) | (1r) | (2dd) | X |
| (3)-160 | (IVh) | (1s) | (2ee) | X |
| (3)-161 | (IVi) | (1n) | (2ff) | (3a) |
| (3)-162 | (IVi) | (1r) | (2ii) | (3b) |
| (3)-163 | (IVi) | (1s) | (2jj) | (3c) |
| (3)-164 | (IVi) | (1v) | (2ll) | (3f) |
| (3)-165 | (IVi) | (1x) | (2ff) | (3k) |
| (3)-166 | (IVi) | (1y) | (2jj) | (3n) |
| (3)-167 | (IVi) | (1z) | (2ff) | (3a) |
| (3)-168 | (IVi) | (1ee) | (2jj) | (3b) |
| (3)-169 | (IVi) | (1ff) | (2p) | (3c) |
| (3)-170 | (IVi) | (1gg) | (2r) | (3f) |
| (3)-171 | (IVi) | (1ii) | (2y) | (3k) |
| (3)-172 | (IVi) | (1jj) | (2n) | (3n) |
| (3)-173 | (IVi) | (1kk) | (2p) | (3s) |
| (3)-174 | (IVi) | (1ll) | (2r) | (3v) |
| (3)-175 | (IVi) | (1ll) | (2y) | (3y) |
| (3)-176 | (IVi) | (1a) | (2z) | (3aa) |
| (3)-177 | (IVi) | (1b) | (2aa) | (3ee) |
| (3)-178 | (IVi) | (1c) | (2dd) | (3c) |
| (3)-179 | (IVi) | (1d) | (2ee) | (3f) |
| (3)-180 | (IVi) | (1f) | (2ff) | (3k) |
| (3)-181 | (Ivj) | (1n) | (2ii) | (3n) |
| (3)-182 | (Ivj) | (1r) | (2jj) | (3s) |
| (3)-183 | (Ivj) | (1s) | (2ll) | (3b) |
| (3)-184 | (Ivj) | (1v) | (2nn) | (3c) |
| (3)-185 | (Ivj) | (1x) | (2ff) | (3a) |
| (3)-186 | (Ivj) | (1y) | (2jj) | (3b) |
| (3)-187 | (Ivj) | (1z) | (2p) | (3a) |
| (3)-188 | (Ivj) | (1ee) | (2r) | (3b) |
| (3)-189 | (Ivj) | (1ff) | (2y) | (3c) |
| (3)-190 | (Ivj) | (1gg) | (2jj) | (3f) |
| (3)-191 | (Ivj) | (1ii) | (2n) | (3k) |
| (3)-192 | (Ivj) | (1jj) | (2p) | (3n) |
| (3)-193 | (Ivj) | (1kk) | (2r) | (3s) |
| (3)-194 | (Ivj) | (1kk) | (2p) | (3v) |
| (3)-195 | (Ivj) | (1kk) | (2r) | (3y) |
| (3)-196 | (Ivj) | (1a) | (2y) | (3aa) |
| (3)-197 | (Ivj) | (1b) | (2z) | (3ee) |
| (3)-198 | (Ivj) | (1c) | (2aa) | (3c) |
| (3)-199 | (Ivj) | (1d) | (2dd) | (3f) |
| (3)-200 | (Ivj) | (1f) | (2ee) | (3k) |

In some embodiments, the compound of formulae (IV) or (IVa)-(IVj) is one of the following compounds (or a pharmaceutically acceptable salt, prodrug, or N-oxide thereof, or a solvate or hydrate thereof): 1, 5, 8, 22, 25, 29, 33, 40, 42, 43, 46, 47.

In some embodiments, the compound of formulae (IV) or (IVa)-(IVj) is one of the following compounds (or a pharmaceutically acceptable salt, prodrug, or N-oxide thereof, or a solvate or hydrate thereof): 29, 42, 46, 47.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I), (Ia)-(Io), (II), (IIa)-(IIn), (III), (IV) and (IVa)-(IVj) described above are useful as kinase inhibitors and/or inhibitors of cytokine signaling. Exemplary kinases inhibited by the presently disclosed compounds include, without limitation, ACVR1; ACVR1B (ALK-4); ACVR1C; ACVR2A; ACVR2B; ACVRL1; BMPR1A; BMPR1B; BMPR2; TGFBR1 (ALK-5), PI3K and MAP4K4 (HGK). Exemplary cytokines, the signaling of which is inhibited by the present compounds include, without limitation, TGF-β superfamily, including Activin, Nodal, TGF-β1, and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, $^{18}F$ etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^{2}H$) may afford certain therapeutic advantages that result from greater metabolic stability. Substitution with positron emitting isotopes, such as 18F can be useful in Positron Emission Tomography (PET) studies. By way of example, deuterium ($^2$H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care anti-proliferative treatments of cancer. The amount of a compound disclosed herein for use in the combination therapy is an amount sufficient to inhibit signaling by members of the TGF-β superfamily, such as Nodal and Activin, which promote the survival and/or differentiation of cancer stem cells and thereby enhance the efficacy of the therapeutic treatment. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

Among the CTLA 4 antibodies that can be used in the present invention is ipilimumab, marketed as YERVOY® by Bristol-Myers Squibb.

Other chemotherapeutic agents for combination with the presently disclosed TGF-β signaling inhibitors include checkpoint pathway inhibitors, e.g., PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TGF-β signaling inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
| --- | --- |
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit signaling by members of the TGF-β superfamily, such as Nodal and Activin, in order to identify cancers and, more specifically, tumors. In one embodiment, neoplasms susceptible to such combination therapy can be identified by testing for Nodal and Activin signaling activity using techniques known to those skilled in the art, including, for example, assays described in Lonardo, E. et al. (2011) Cell Stem Cell 9, 433-446 (which is hereby incorporated by reference in its entirety). Optionally in this embodiment, where the tested compound is found to inhibit signaling of a member of the TGF-β superfamily, such as Nodal and Activin, in the tested neoplasm, the compound is subsequently used in a combination therapy for treatment of the neoplasm, as described herein.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions on with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$O, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, NR$^{71}$C(S)R$^{71}$, —NR$^{71}$CO$_2^-$M$^+$, —NR$^{71}$CO$_2$R$^{71}$, —NR$^{71}$C(S)OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$alkyl) or (C$_1$-C$_6$fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$alkyl substitution. Each M$^+$ may independently be, for example, an alkali ion, such as K$^+$, Na$^+$, Li+; an ammonium ion, such as $^+$N(R$^{60}$)$_4$; Or an alkaline earth ion, such as [Ca$^{2+}$]$_{0.5}$, [Mg$^{2+}$]$_{0.5}$, or [Ba$^{2+}$]$_{0.5}$("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$V$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)—R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—(C$_1$-C$_4$alkyl), —O—(C$_1$-C$_4$haloalkyl), —N(C$_0$-C$_4$ alkyl)(C$_0$-C$_4$alkyl), —SH, —S(O)$_{0-2}$—(C$_1$-C$_4$alkyl), —(C$_1$-C$_4$alkyl), —(C$_1$-C$_4$haloalkyl), —C(O)—(C$_0$-C$_4$alkyl), —C(O)N(C$_0$-C$_4$alkyl)(C$_0$-C$_4$alkyl), —N(C$_0$-C$_4$alkyl)C(O)(C$_0$-C$_4$alkyl)(C$_0$-C$_4$alkyl), —C(O)O—(C$_0$-C$_4$alkyl), —OC(O)—(C$_0$-C$_4$alkyl), S(O)$_2$—O(C$_0$-C$_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., modulation or inhibition of GDF-8 or TGF-β1).

Manifestation of amelioration of a disease condition by inhibiting GDF-8 or TGF-β1 may require the concomitant or sequential administration of additional therapeutic agents, such as antineoplastic agents in the case of cancer, or antiretroviral agents in the case of viral diseases. For example, administration of GDF-8 and TGF-β1 inhibitors for the treatment of cancer does not always produce a direct antitumor effect when used as a single agent. However, when combined with chemotherapeutic drugs (antineoplastic) the antitumor effect observed is higher than the sum of effects of each agent alone In one embodiment the present compounds are used as immunomodulators to increase an immune response or to abrogate a tumor's ability to evade the immune response. In one embodiment of a method for using the present compounds, one or more inhibitor of TGF-β receptor superfamily signaling is used in combination with an immunooncology treatment.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(IV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(IV).

In the pharmaceutical compositions disclosed herein, one or more compounds of structural formulae (I)-(IV) may be present in association with one or more pharmaceutically acceptable carriers, diluents or excipients, and, if desired, other active ingredients. The pharmaceutical compositions containing compounds of structural formulae (I)-(IV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(IV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(IV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1 and 2 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(IV) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

The following examples are intended to further illustrate certain embodiments and are not intended to limit the scope of the presently disclosed compounds.

Examples

Example 1: Synthesis and Characterization

Scheme 1: General Scheme for the Preparation of Aminoindazoles and Aminoaza-Indazole Anilines with Pyrimidines

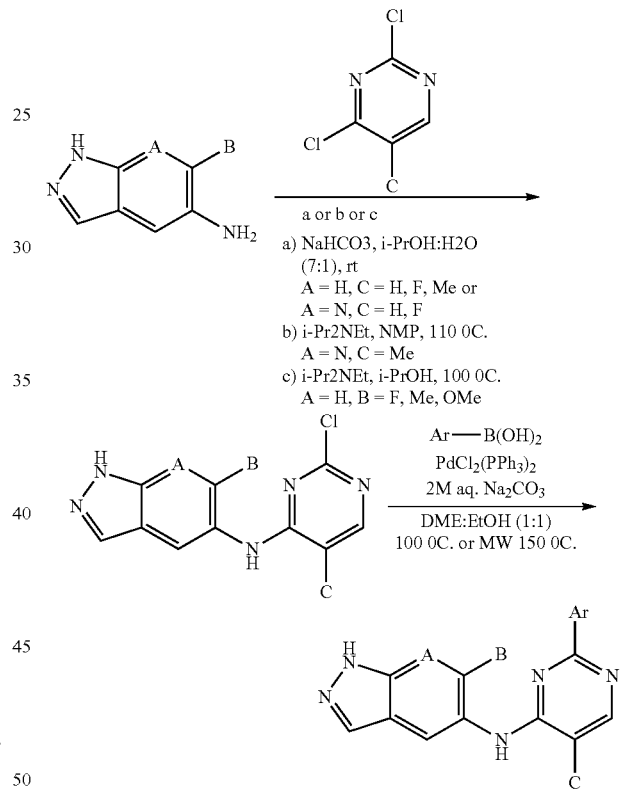

Scheme 2: General Scheme for the Preparation of Aminoindazoles and Aminoaza-Indazoles with Non-Substituted Pyrimidines

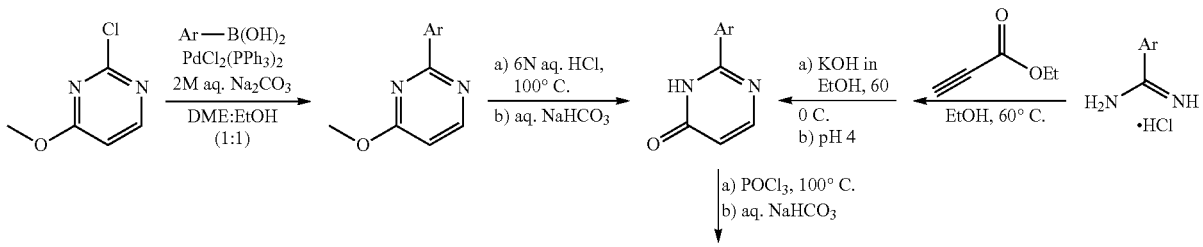

-continued
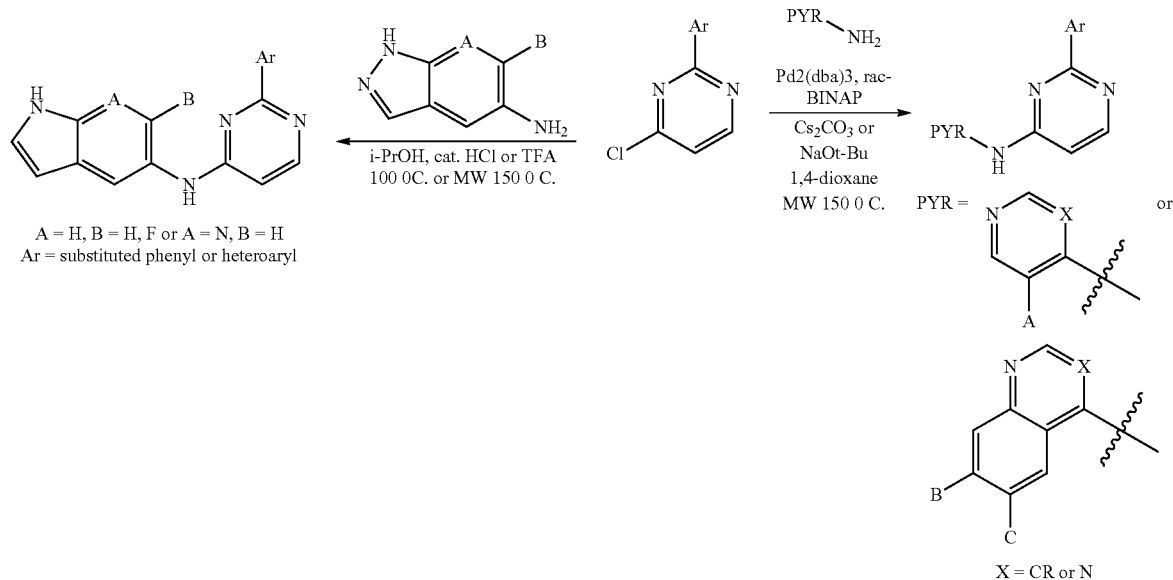
Scheme 3: General Scheme for the Preparation of Aminoindazoles and Aminoaza-Indazoles with Quinazolines
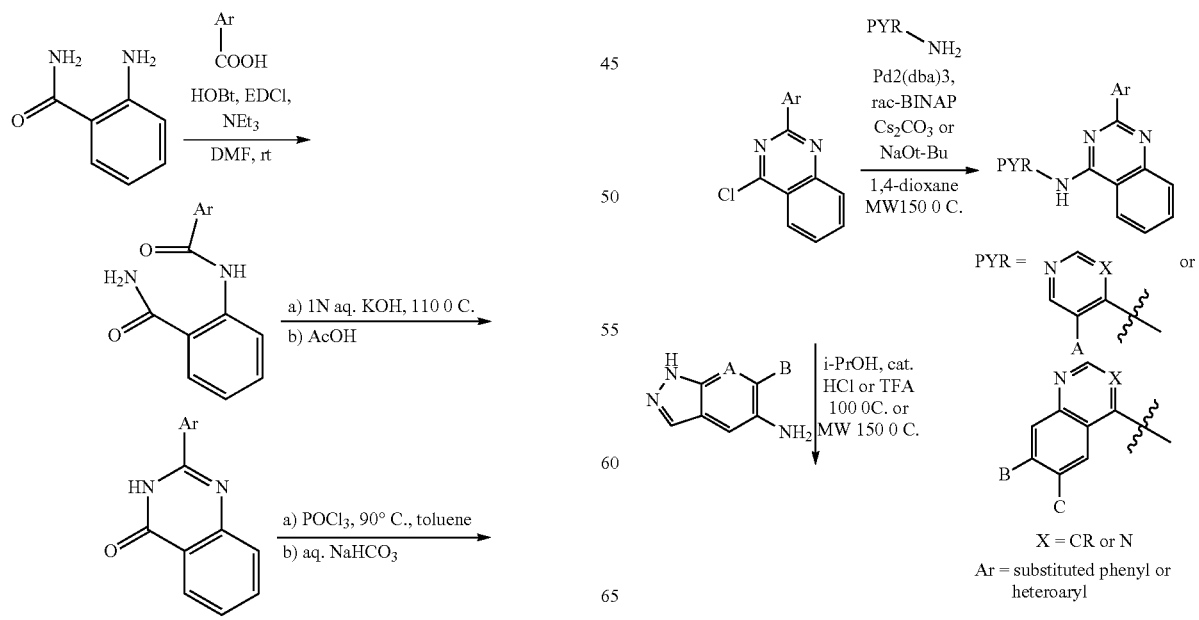

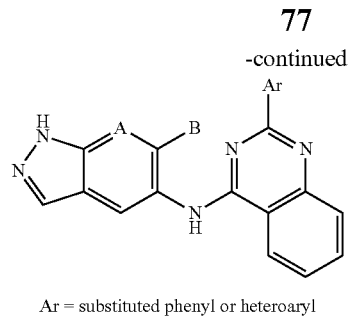

Ar = substituted phenyl or heteroaryl

A = CH, B = F, Me, OMe
A = N, B = H

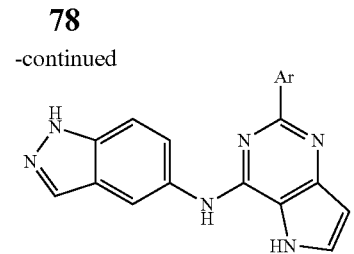

Scheme 5: General Scheme for the Alkylation of Aminoindazoles

Scheme 4: General Scheme for the Preparation of N-(1H-indazol-5-yl)-2-aryl-7H-pyrrolo[2,3-d]pyrimidin-4-amines or N-(1H-indazol-5-yl)-2-aryl-5H-pyrrolo[3,2-d]pyrimidin-4-amines

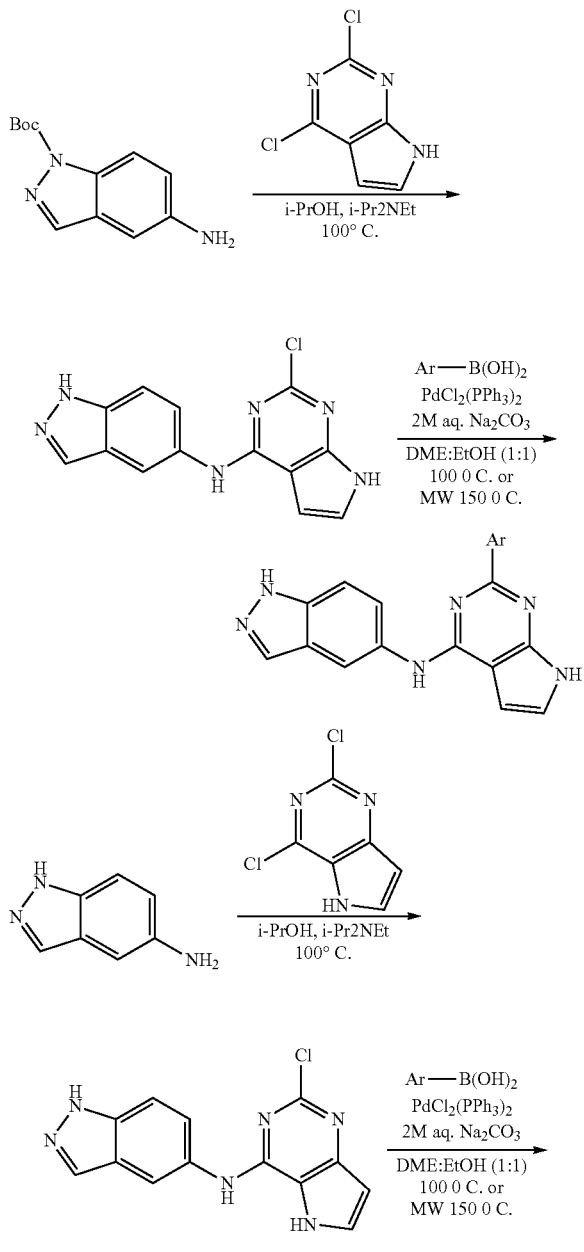

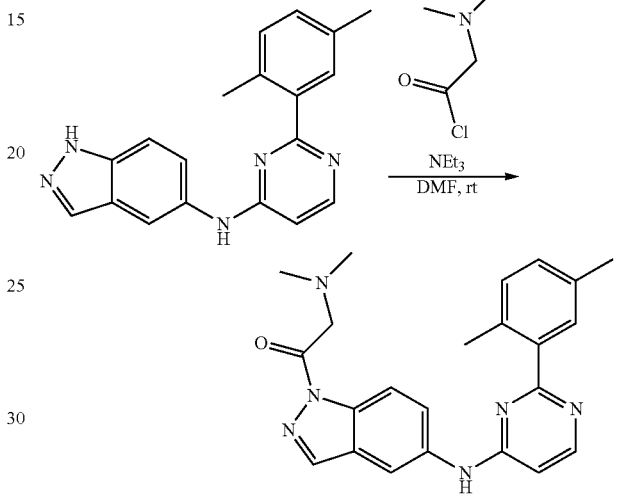

LC/MC Method

LC/MS: rt (Method A or Method B), rt=peak retention time

Method A: Column: Luna 5 μm C8 (100×4.6 mm), Flow rate 1.0 mL/min, Mobile phase: A: $H_2O$ 0.05% TFA, B: $CH_3CN$ 0.05% TFA Method B: Column: Gemini 5 μm C18 (100×4.6 mm), Flow rate 1.5 mL/min, Mobile phase: A: $H_2O$ 0.05% HCOOH, B: $CH_3CN$ 0.05% HCOOH Compound 1: 2-(Dimethylamino)-1-(5-((2-(2,5-dimethylphenyl)pyrimidin-4-yl)amino)-1H-indazol-1-yl)ethan-1-one. $^1$H NMR (300 MHz, DMSO-$d_6$) δ 9.55 (s, 1H), 8.32 (d, J=7.0 Hz, 1H), 8.12-8.04 (m, 1H), 7.98 (s, 1H), 7.60-7.36 (m, 3H), 7.15-7.14 (m, 2H), 6.65 (d, J=7.2 Hz, 1H), 3.22 (s, 2H), 2.56 (s, 6H), 2.41 (s, 3H), 2.31 (s, 3H). LCMS: rt min (A), purity %, MS (m/e) 401 MH$^+$.

Compound 2: 2-(6-Methylpyridin-2-yl)-N-(1H-pyrazolo[3,4-b]pyridin-5-yl)quinazolin-4-amine. $^1$H NMR (300 MHz, DMSO-$d_6$) δ 13.73 (s, 1H), 11.04 (s, 1H), 8.97 (d, J=2.3 Hz, 1H), 8.87 (d, J=2.3 Hz, 1H), 8.78 (d, J=8.3 Hz, 1H), 8.21 (s, 1H), 8.15 (d, J=8.4 Hz, 1H), 8.06 (d, J=7.7 Hz, 1H), 8.00 (t, J=7.6 Hz, 1H), 7.89 (t, J=7.7 Hz, 1H), 7.77 (t, J=7.4 Hz, 1H), 7.47 (d, J=7.7 Hz, 1H), 2.65 (s, 3H). LCMS: rt 4.92 min (A), purity 99%, MS (m/e) 354 MH$^+$.

Compound 3: N-(2-(3,4-Difluorophenyl)pyrimidin-4-yl)-1H-pyrazolo[3,4-b]pyridin-5-amine. LCMS: rt 4.14 min (B), purity 98%, MS (m/e) 325 MH$^+$.

Compound 4: N-(2-(4-Fluorophenyl)pyrimidin-4-yl)-1H-pyrazolo[3,4-b]pyridin-5-amine. LCMS: rt 3.07 min (A), purity 99%, MS (m/e) 307 MH$^+$.

Compound 5: 2-(4-Fluorophenyl)-N-(1H-indazol-5-yl)-7H-pyrrolo[2,3-d]pyrimidin-4-amine. $^1$H NMR (300 MHz, DMSO-$d_6$) δ 11.79 (s, 1H), 9.49 (s, 1H), 8.37 (app dd, J=8.7, 5.8 Hz, 2H), 8.28 (s, 1H), 8.08 (d, J=0.9 Hz, 1H), 7.79-7.69 (m, 1H), 7.57 (d, J=9.0 Hz, 1H), 7.29 (app t, J=8.8 Hz, 2H), 7.22 (t, J=2.9 Hz, 1H), 6.67 (s, 1H). $^{19}$F NMR (282 MHz, DMSO-d$_6$) δ−112.76. LCMS: rt 5.32 min (A), purity 99%, MS (m/e) 345 MH$^+$.

Compound 6: 2-(3,4-Difluorophenyl)-N-(1H-indazol-5-yl)-7H-pyrrolo[2,3-d]pyrimidin-4-amine. LCMS: rt 6.02 min (A), purity 99%, MS (m/e) 363 MH$^+$.

Compound 7: 2-(2,4-Difluorophenyl)-N-(1H-indazol-5-yl)-7H-pyrrolo[2,3-d]pyrimidin-4-amine. LCMS: rt 5.07 min (A), purity 99%, MS (m/e) 363 MH$^+$.

Compound 8: 2-(4-Fluoro-3-methylphenyl)-N-(1H-indazol-5-yl)-7H-pyrrolo[2,3-d]pyrimidin-4-amine. LCMS: rt 5.63 min (A), purity 99%, MS (m/e) 359 MH$^+$.

Compound 9: N-(1H-Indazol-5-yl)-2-(3-methylphenyl)-7H-pyrrolo[2,3-d]pyrimidin-4-amine. LCMS: rt 5.22 min (B), purity 99%, MS (m/e) 341 MH$^+$.

Compound 10: 2-(4-Fluorophenyl)-N-(1H-indazol-5-yl)-5H-pyrrolo[3,2-d]pyrimidin-4-amine. $^1$H NMR (300 MHz, DMSO-d$_6$) δ 13.20 (s, 1H), 11.78 (s, 1H), 10.38 (s, 1H), 8.34-8.21 (m, 3H), 8.14 (s, 1H), 7.85 (s, 1H), 7.74-7.59 (m, 2H), 7.42 (app t, J=8.7 Hz, 2H), 6.62 (s, 1H). LCMS: rt 5.28 min (A), purity 97%, MS (m/e) 345 MH$^+$.

Compound 11: N-(1H-Indazol-5-yl)-2-(3-methylphenyl)-5H-pyrrolo[3,2-d]pyrimidin-4-amine. LCMS: rt 5.48 min (A), purity 99%, MS (m/e) 341 MH$^+$.

Compound 12: N-(5-Fluoro-2-(4-fluoro-2-methylphenyl)pyrimidin-4-yl)-1H-pyrazolo[3,4-b]pyridin-5-amine. $^1$H NMR (300 MHz, DMSO-d$_6$) δ 13.64 (s, 1H), 9.83 (s, 1H), 8.73 (s, 1H), 8.48 (d, J=3.7 Hz, 1H), 8.41 (d, J=2.3 Hz, 1H), 8.11 (s, 1H), 7.74 (dd, J=9.1, 6.2 Hz, 1H), 7.16-7.00 (m, 2H), 2.37 (s, 3H). LCMS: rt 5.42 min (A), purity 99%, MS (m/e) 339 MH$^+$.

Compound 13: N-(2-(3-Fluorophenyl)-5-methylpyrimidin-4-yl)-1H-pyrazolo[3,4-b]pyridin-5-amine. $^1$H NMR (300 MHz, DMSO-d$_6$) δ 13.63 (s, 1H), 9.00 (s, 1H), 8.78 (d, J=2.3 Hz, 1H), 8.40 (d, J=2.3 Hz, 1H), 8.29 (s, 1H), 8.15 (s, 1H), 8.00 (d, J=7.8 Hz, 1H), 7.85 (dt, J=11.0, 2.2 Hz, 1H), ), 7.48 (td, J=8.0, 6.1 Hz, 1H),), 7.28 (td, J=8.5, 2.6 Hz, 1H), 2.27 (s, 3H). LCMS: rt 4.47 min (A), purity 99%, MS (m/e) 321 MH$^+$.

Compound 14: N-(2-(4-Fluorophenyl)-5-methylpyrimidin-4-yl)-1H-pyrazolo[3,4-b]pyridin-5-amine. LCMS: rt 4.50 min (A), purity 99%, MS (m/e) 320 MH$^+$.

Compound 15: N-(2-(3,4-Difluorophenyl)-5-methylpyrimidin-4-yl)-1H-pyrazolo[3,4-b]pyridin-5-amine. $^1$H NMR (300 MHz, DMSO-d$_6$) δ 13.52 (s, 1H), 9.15 (s, 1H), 8.76 (d, J=2.3 Hz, 1H), 8.38 (d, J=2.3 Hz, 1H), 8.29 (s, 1H), 8.16 (s, 1H), 8.09-7.92 (m, 2H), 7.53 (dt, J=10.4, 8.3 Hz, 1H), 2.27 (s, 3H). LCMS: rt 4.75 min (A), purity 99%, MS (m/e) 339 MH$^+$.

Compound 16: N-(2-(3-Methylphenyl)-5-methylpyrimidin-4-yl)-1H-pyrazolo[3,4-b]pyridin-5-amine. LCMS: rt 2.82 min (B), purity 99%, MS (m/e) 317 MH$^+$.

Compound 17: N-(2-(2-Fluorophenyl)pyrimidin-4-yl)-1H-indazol-5-amine. $^1$H NMR (300 MHz, DMSO-d$_6$) δ 12.97 (s, 1H), 9.64 (s, 1H), 8.34 (d, J=5.9 Hz, 1H), 8.20 (s, 1H), 8.05-7.87 (m, 2H), 7.54-7.47 (s, 3H), 7.30 (app t, J=8.8 Hz, 2H), 6.70 (d, J=5.9 Hz, 1H). $^{19}$F NMR (282 MHz, DMSO-d$_6$) δ−114.71 (ddd, J=12.0, 7.8, 5.0 Hz). LCMS: rt min (A), purity %, MS (m/e) 306 MH$^+$.

Compound 18: N-(2-(3-Fluorophenyl)pyrimidin-4-yl)-1H-indazol-5-amine. $^1$H NMR (300 MHz, DMSO-d$_6$) δ12.97 (s, 1H), 10.29 (s, 1H), 8.35 (d, J=6.3 Hz, 1H), 8.12-8.09 (app m, 2H), 7.98 (d, J=10.4 Hz, 1H), 7.61-7.44 (m, 3H), 7.47-7.10 (m, 2H), 6.79 (d, J=6.2 Hz, 1H). $^{19}$F NMR (282 MHz, DMSO-d$_6$) δ−112.60 (q, J=8.7 Hz), −114.42-114.80 (m). LCMS: rt 4.77 min (A), purity 98%, MS (m/e) 306 MH$^+$.

Compound 19: N-(2-(3-Methoxyphenyl)pyrimidin-4-yl)-1H-indazol-5-amine. LCMS: rt 2.72 min (A), purity 98%, MS (m/e) 318 MH$^+$.

Compound 20: N-(2-Phenylpyrimidin-4-yl)-1H-indazol-5-amine. LCMS: rt 2.40 min (A), purity 95%, MS (m/e) 288 MH$^+$.

Compound 21: N-(2-(2-Methylphenyl)pyrimidin-4-yl)-1H-indazol-5-amine. LCMS: rt 2.22 min (A), purity 96%, MS (m/e) 302 MH$^+$.

Compound 22: N-(2-(3,4-Difluorophenyl)pyrimidin-4-yl)-1H-indazol-5-amine. $^1$H NMR (300 MHz, DMSO-d$_6$) δ 12.82 (s, 1H), 10.55 (s, 1H), 8.36 (d, J=6.5 Hz, 1H), 8.12 (s, 1H), 8.08-7.98 (m, 2H), 7.64-7.36 (m, 3H), 7.29 (td, J=8.9, 2.7 Hz, 1H), 6.84 (d, J=6.5 Hz, 1H). $^{19}$F NMR (282 MHz, DMSO-d$_6$) δ−105.31(s), −108.95 (q, J=10.2 Hz). LCMS: rt 4.67 min (A), purity 98%, MS (m/e) 324 MH$^+$.

Compound 23: 6-Fluoro-N-(2-(2-fluorophenyl)pyrimidin-4-yl)-1H-indazol-5-amine. LCMS: rt 4.55 min (A), purity 98%, MS (m/e) 324 MH$^+$.

Compound 24: N-(5-Fluoro-2-(2-fluorophenyl)pyrimidin-4-yl)-1H-indazol-5-amine. LCMS: rt 5.45 min (A), purity 99%, MS (m/e) 324 MH$^+$.

Compound 25: N-(2-(3,4-Difluorophenyl)pyrimidin-4-yl)-1H-indazol-5-amine. $^1$H NMR (300 MHz, DMSO-d$_6$) δ 13.11 (s, 1H), 9.76 (s, 1H), 8.40 (d, J=5.9 Hz, 1H), 8.34-8.19 (m, 2H), 8.14 (d, J=5.8 Hz, 2H), 7.75-7.48 (m, 3H), 6.75 (d, J=5.9 Hz, 1H). $^{19}$F NMR (282 MHz, DMSO-d$_6$) δ−136.27-136.66 (m), −138.23 (dt, J=21.8, 10.5 Hz). LCMS: rt 5.07 min (A), purity 98%, MS (m/e) 324 MH$^+$.

Compound 26: N-(2-(5-fluoro-2-methylphenyl)pyrimidin-4-yl)-1H-indazol-5-amine. LCMS: rt 5.02 min (A), purity 100%, MS (m/e) 320 MH$^+$.

Compound 27: N-(2-(3,5-Difluorophenyl)pyrimidin-4-yl)-1H-indazol-5-amine. $^1$H NMR (300 MHz, DMSO-d$_6$) δ 13.06 (s, 1H), 9.73 (s, 1H), 8.34 (d, J=5.9 Hz, 1H), 8.04 (s, 2H), 7.87 (d, J=6.7 Hz, 2H), 7.57 (d, J=8.9 Hz, 1H), 7.51 (d, J=8.5 Hz, 1H), 7.37 (t, J=9.1 Hz, 1H), 6.71 (d, J=5.9 Hz, 1H). $^{19}$F NMR (282 MHz, DMSO-d$_6$) δ−109.42 (t, J=8.7 Hz). LCMS: rt 5.33 min (A), purity 100%, MS (m/e) 324 MH$^+$.

Compound 28: N-(2-(3-Fluoro-4-methoxyphenyl)pyrimidin-4-yl)-1H-indazol-5-amine. LCMS: rt 5.12 min (A), purity 99%, MS (m/e) 336 MH$^+$.

Compound 29: N-(2-(3-Cyanophenyl)pyrimidin-4-yl)-1H-indazol-5-amine. $^1$H NMR (300 MHz, DMSO-d$_6$) δ 13.09 (s, 1H), 9.81 (s, 1H), 8.64-8.54 (m, 2H), 8.37 (d, J=6.0 Hz, 1H), 8.09 (s, 1H), 8.05 (d, J=0.8 Hz, 1H), 7.97 (dt, J=7.6, 1.4 Hz, 1H), 7.74 (td, J=7.6, 0.8 Hz, 1H), 7.59-7.50 (m, 2H), 6.73 (d, J=6.0 Hz, 1H). LCMS: rt 4.70 min (A), purity 98%, MS (m/e) 313 MH$^+$.

Compound 30: N-(2-(2,5-Dimethylphenyl)pyrimidin-4-yl)-1H-indazol-5-amine. $^1$H NMR (300 MHz, DMSO-d$_6$) δ 12.97 (s, 1H), 9.54 (s, 1H), 8.32 (dd, J=5.9, 0.7 Hz, 1H), 8.08 (s, 1H), 7.98 (s, 1H), 7.56 (s, 1H), 7.51 (d, J=8.9 Hz, 1H), 7.44 (dd, J=8.9, 1.4 Hz, 1H), 7.13 (s, 2H), 6.65 (d, J=6.4 Hz, 1H), 2.41 (s, 3H), 2.31 (s, 3H). LCMS: rt 5.05 min (A), purity 98%, MS (m/e) 316 MH$^+$.

Compound 31: N-(2-(3-Aminophenyl)pyrimidin-4-yl)-1H-indazol-5-amine. $^1$H NMR (300 MHz, DMSO-d$_6$) δ 12.98 (s, 1H), 9.53 (s, 1H), 8.29 (d, J=5.8 Hz, 1H), 8.21 (s, 1H), 8.09 (s, 1H), 7.63-7.42 (m, 4H), 7.12 (t, J=7.8 Hz, 1H), 6.67 (dd, J=7.9, 1.4 Hz, 1H), 6.63 (d, J=5.9 Hz, 1H), 5.18 (s, 2H). LCMS: rt 3.65 min (A), purity 99%, MS (m/e) 303 MH$^+$.

Compound 32: N-(2-(3-Methylphenyl)pyrimidin-4-yl)-1H-indazol-5-amine. LCMS: rt 5.23 min (A), purity 99%, MS (m/e) 302 MH$^+$.

Compound 33: N-(2-(4-Fluorophenyl)pyrimidin-4-yl)-1H-indazol-5-amine. LCMS: rt 4.80 min (A), purity 99%, MS (m/e) 306 MH$^+$.

Compound 34: N-(5-Fluoro-2-(methylphenyl)pyrimidin-4-yl)-1H-indazol-5-amine. LCMS: rt 5.00 min (A), purity 99%, MS (m/e) 320 MH$^+$.

Compound 35: N-(2-(3,4-Difluorophenyl)-5-fluoropyrimidin-4-yl)-1H-indazol-5-amine. $^1$H NMR (300 MHz, DMSO-d$_6$) δ 13.09 (s, 1H), 9.76 (s, 1H), 8.43 (d, J=3.8 Hz, 1H), 8.17-7.91 (m, 4H), 7.73-7.62 (m, 1H), 7.62-7.45 (m, 3H). $^{19}$F NMR (282 MHz, DMSO-d$_6$) δ−136.62-137.12 (m), −138.13 (dt, J=21.3, 10.1 Hz), −153.58 (s). LCMS: rt 7.25 min (A), purity 98%, MS (m/e) 342 MH$^+$.

Compound 36: N-(5-Fluoro-2-(3-fluorophenyl)pyrimidin-4-yl)-1H-indazol-5-amine. LCMS: rt 6.72 min (A), purity 99%, MS (m/e) 324 MH$^+$.

Compound 37: N-(5-Fluoro-2-phenylpyrimidin-4-yl)-1H-indazol-5-amine. LCMS: rt 5.58 min (A), purity 99%, MS (m/e) 306 MH$^+$.

Compound 38: N-(2-(2-Fluorophenyl)-5-methylpyrimidin-4-yl)-1H-indazol-5-amine. $^1$H NMR (300 MHz, DMSO-d$_6$) δ 12.90 (s, 1H), 8.58 (s, 1H), 8.23 (d, J=1.1 Hz, 1H), 8.13 (dd, J=2.1, 0.8 Hz, 1H), 7.99 (d, J=1.0 Hz, 1H), 7.90 (td, J=7.7, 1.9 Hz, 1H), 7.65 (dd, J=8.9, 2.0 Hz, 1H), 7.56-7.37 (m, 2H), 7.30-7.15 (m, 2H), 2.25 (s, 3H). $^{19}$F NMR (282 MHz, DMSO-d$_6$) δ−138.42 (app dt, J=21.4, 10.5 Hz), −138.91-139.20 (m). LCMS: rt 4.53 min (A), purity 99%, MS (m/e) 320 MH$^+$.

Compound 39: N-(2-(2-Methylphenyl)-5-methylpyrimidin-4-yl)-1H-indazol-5-amine. LCMS: rt 4.67 min (A), purity 100%, MS (m/e) 316 MH$^+$.

Compound 40: N-(2-(3,4-Difluorophenyl)-5-methylpyrimidin-4-yl)-1H-indazol-5-amine. LCMS: rt 5.05 min (A), purity 99%, MS (m/e) 338 MH$^+$.

Compound 41: N-(2-(2,5-Dimethylphenyl)-5-methylpyrimidin-4-yl)-1H-indazol-5-amine. $^1$H NMR (300 MHz, DMSO-d$_6$) δ 12.96 (s, 1H), 8.53 (s, 1H), 8.26-8.14 (m, 1H), 7.98 (s, 2H), 7.58-7.41 (m, 3H), 7.06 (d, J=1.1 Hz, 2H), 2.31 (s, 3H), 2.26 (s, 3H), 2.23 (s, 3H). LCMS: rt 5.05 min (A), purity 96%, MS (m/e) 330 MH$^+$.

Compound 42: N-(2-(4-Fluoro-2-methylphenyl)pyrimidin-4-yl)-1H-indazol-5-amine. LCMS: rt 4.78 min (A), purity 98%, MS (m/e) 320 MH$^+$.

Compound 43: N-(2-(4-Fluoro-3-methylphenyl)pyrimidin-4-yl)-1H-indazol-5-amine. LCMS: rt 5.30 min (A), purity 98%, MS (m/e) 320 MH$^+$.

Compound 44: N-(2-(2-Aminophenyl)pyrimidin-4-yl)-1H-indazol-5-amine. LCMS: rt 4.38 min (A), purity 99%, MS (m/e) 303 MH$^+$.

Compound 45: N-(2-(3-Trifluoromethylphenyl)pyrimidin-4-yl)-1H-indazol-5-amine. LCMS: rt 5.48 min (A), purity 97%, MS (m/e) 356 MH$^+$.

Compound 46: N-(2-(4-Methoxy-2-methylphenyl)pyrimidin-4-yl)-1H-indazol-5-amine. LCMS: rt 4.88 min (A), purity 99%, MS (m/e) 332 MH$^+$.

Compound 47: N-(2-(4-Fluoro-2-methylphenyl)pyrimidin-4-yl)-6,7-dimethoxyquinolin-4-amine. $^1$H NMR (300 MHz, DMSO-d$_6$) δ 10.66 (s, 1H), 8.83 (d, J=5.7 Hz, 1H), 8.78 (d, J=6.7 Hz, 1H), 8.59 (d, J=6.7 Hz, 1H), 8.00 (s, 1H), 7.89 (dd, J=8.6, 6.2 Hz, 1H), 7.46 (s, 1H), 7.41 (d, J=5.7 Hz, 1H), 7.25-7.08 (m, 2H), 4.04 (s, 3H), 4.00 (s, 3H), 2.53 (s, 3H). $^{19}$F NMR (282 MHz, DMSO-d$_6$) δ−112.41-112.64 (m). LCMS: rt 5.38 min (A), purity 99%, MS (m/e) 391 MH$^+$.

Compound 48: N-(2-(2-Fluoro-5-methylphenyl)pyrimidin-4-yl)-1H-indazol-5-amine. LCMS: rt 4.87 min (A), purity 98%, MS (m/e) 320 MH$^+$.

Compound 49: N-(2-(4-Fluoro-3-methylphenyl)-5-methylpyrimidin-4-yl)-1H-pyrazolo[3,4-b]pyridin-5-amine. $^1$H NMR (300 MHz, DMSO-d$_6$) δ 13.49 (s, 1H), 8.84-8.79 (m, 1H), 8.78 (d, J=2.4 Hz, 1H), 8.45 (d, J=2.4 Hz, 1H), 8.23 (d, J=1.0 Hz, 1H), 8.15 (s, 1H), 8.12 (d, J=7.8 Hz, 1H), 8.00 (td, J=5.7, 2.7 Hz, 1H), 7.31-7.02 (m, 1H), 2.25 (s, 6H). LCMS: rt 4.83 min (A), purity 99%, MS (m/e) 335 MH$^+$.

Compound 50: N-(2-(4-Fluorophenyl)-7H-pyrrolo[2,3-d]pyrimidin-4-yl)-1H-pyrazolo[3,4-b]pyridin-5-amine. $^1$H NMR (300 MHz, DMSO-d$_6$) δ 1323 (s, 1H), 11.82 (s, 1H), 9.62 (s, 1H), 8.91 (d, J=2.4 Hz, 1H), 8.65 (d, J=2.3 Hz, 1H), 8.34 (dd, J=8.7, 5.9 Hz, 2H), 8.16 (s, 1H), 7.41-7.12 (m, 3H), 6.73 (dd, J=3.5, 1.6 Hz, 1H). $^{19}$F NMR (282 MHz, DMSO-d$_6$) δ−112.86 (app s). LCMS: rt 4.35 min (A), purity 97%, MS (m/e) 346 MH$^+$.

Compound 51: N-(2-(4-Fluoro-3-methylphenyl)-5-methylpyrimidin-4-yl)-6-methyl-1H-indazol-5-amine. $^1$H NMR (300 MHz, DMSO-d$_6$) δ 13.08 (s, 1H), 9.33 (s, 1H), 8.28 (s, 1H), 8.04 (d, J=1.0 Hz, 1H), 7.76 (d, J=7.9 Hz, 1H), 7.69 (s, 1H), 7.68-7.61 (m, 1H), 7.51 (d, J=5.1 Hz, 1H), 7.49-7.41 (m, 1H), 7.37-7.26 (m, 1H), 2.29 (s, 3H), 2.28 (s, 3H). LCMS: rt 4.92 min (A), purity 99%, MS (m/e) 334 MH$^+$.

Compound 52: N-(2-(3-Methylphenyl)-5-methylpyrimidin-4-yl)-6-methyl-1H-indazol-5-amine. LCMS: rt 5.13 min (A), purity 99%, MS (m/e) 330 MH$^+$.

Compound 53: N-(2-(4-Fluorophenyl)-5-methylpyrimidin-4-yl)-6-methyl-1H-indazol-5-amine. LCMS: rt 4.93 min (A), purity 99%, MS (m/e) 334 MH$^+$.

Compound 54: N-(2-(3,4-Difluorophenyl)-5-methylpyrimidin-4-yl)-6-methyl-1H-indazol-5-amine. LCMS: rt 5.12 min (A), purity 99%, MS (m/e) 352 MH$^+$.

Compound 55: N-(2-(2,5-Dimethylphenyl)-5-methylpyrimidin-4-yl)-6-methyl-1H-indazol-5-amine. $^1$H NMR (300 MHz, DMSO-d$_6$) δ 13.20 (s, 1H), 9.96 (s, 1H), 8.35 (s, 1H), 8.01 (s, 1H), 7.64 (s, 1H), 7.45 (s, 1H), 7.35-7.30 (m, 1H), 7.23-7.15 (m, 1H), 7.08 (d, J=7.5 Hz, 1H), 2.33 (s, 3H), 2.27 (s, 3H), 2.25 (s, 3H), 2.00 (s, 3H). LCMS: rt 5.18 min (A), purity 99%, MS (m/e) 344 MH$^+$.

Compound 56: N-(2-(4-Fluoro-3-methylphenyl)-5-methylpyrimidin-4-yl)-6-methyl-1H-indazol-5-amine. LCMS: rt 5.30 min (A), purity 97%, MS (m/e) 348 MH$^+$.

Compound 57: 6-Fluoro-N-(2-(3-fluorophenyl)-5-methylpyrimidin-4-yl)-1H-indazol-5-amine. LCMS: rt 4.90 min (A), purity 99%, MS (m/e) 338 MH$^+$.

Compound 58: 6-Fluoro-N-(2-(3-methylphenyl)-5-methylpyrimidin-4-yl)-1H-indazol-5-amine. LCMS: rt 5.08 min (A), purity 99%, MS (m/e) 334 MH$^+$.

Compound 59: 6-Fluoro-N-(2-(2,5-dimethylphenyl)-5-methylpyrimidin-4-yl)-1H-indazol-5-amine. LCMS: rt 5.17 min (A), purity 99%, MS (m/e) 348 MH$^+$.

Compound 60: 6-Fluoro-N-(2-(3,4-difluorophenyl)-5-methylpyrimidin-4-yl)-1H-indazol-5-amine. LCMS: rt 5.12 min (A), purity 97%, MS (m/e) 356 MH$^+$.

Compound 61: 6-Fluoro-N-(2-(4-fluoro-3-methylphenyl)-5-methylpyrimidin-4-yl)-1H-indazol-5-amine. LCMS: rt 5.23 min (A), purity 99%, MS (m/e) 352 MH$^+$.

Compound 62: N-(2-(2-Fluorophenyl)-5-methylpyrimidin-4-yl)-6-methoxy-1H-indazol-5-amine. $^1$H NMR (300 MHz, DMSO-d$_6$) δ 9.33 (s, 1H), 8.33 (s, 1H), 7.99 (s, 1H), 7.96 (s, 1H), 7.76-7.64 (m, 1H), 7.64-7.50 (m, 1H), 7.43-7.24 (m, 2H), 7.08 (s, 1H), 3.86 (s, 3H), 2.30 (s, 3H). $^{19}$F NMR (282 MHz, DMSO-d$_6$) δ−114.46 (dt, J=12.0, 6.0 Hz). LCMS: rt 4.70 min (A), purity 99%, MS (m/e) 350 MH$^+$.

Compound 63: N-(2-(3,4-Difluorophenyl)-5-methylpyrimidin-4-yl)-6-methoxy-1H-indazol-5-amine. LCMS: rt 5.27 min (A), purity 99%, MS (m/e) 368 MH+.

Example 2: AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

1× Lysis buffer: 1 ml of 5× Lysis buffer was diluted with 4 ml of sterile water. After dilution, excess 1× Lysis buffer can be frozen and thawed up to 5 times without loss in activity.

P-SMAD-3 (Ser423/425) SureFire® Assay Protocols
Step A: Preparation of Buffers

Activation buffer: The buffer was warmed slowly to 37° C. and gently mixed to re-suspend. Activation buffer can be stored at room temperature with no loss in activity.

Reaction buffer: The buffer was kept at 4° C. while in use.

AlphaScreen® Protein A IgG Kit: The kit was stored at 4° C. in the dark.

Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture was discarded.

Dilution buffer+AlphaScreen® Donor beads: Dilution buffer (20 parts) and Donor beads (1 part) were mixed and the mixture was stored at room temperature and used the same day. Excess mixture was discarded.

Assay control samples: After reconstitution in 250 1 of water, lysates were at −20° C. in single use aliquots.
Step B: Preparation of Samples and Cells 96-well Assay Protocol for 293FT and RMS13 adherent cells can be carried out manually or in high throughput with liquid handling robots.

The cells (80 µL of cells for 96 well plates) were plated in collagen coated tissue culture plates in RPMI or FreeStyle medium (Invitrogen) and incubated overnight. For manual analysis, 6 plates for GDF8, 6 plates for TGFβ, and optionally 6 plates for Alk5ca(ALK5 constitutively active) were used.

The compound dilution plates were prepared as follows: 12 µL of DMSO was transferred into first column of 96-well plate, and 16 µL of DMSO was transferred into columns 2-12 of the 96-well plate. 12 µL of compound solution was transferred into first column of the DMSO-containing 96-well plate. Three-fold dilution was performed up to column 10 of the DMSO-containing 96-well plate.
Step C: Treatment and Analysis The plate containing cells were treated with compounds for about 10 minutes, and then ligand was added. GDF8 or TGFb was added to plates to stimulate. 293FL cells were stimulated for 90 minutes at 37° C.; and RMS13 cells were stimulated for 60 minutes at 37° C. The medium was then removed from the cells, and 1× Lysis Buffer (about 25 µL) was added and the plate was gently agitated on plate shaker for 5-10 minutes.

The lysate (5 µL) was then placed into 384-well shallow plates avoiding the generation of bubbles. To this, the Reaction Buffer+Activation Buffer+AlphaScreen® Acceptor beads mixture (5 µL) was added. The plate was sealed with adhesive cover and shielded from light (e.g., with metal foil), and agitated gently on plate shaker for 2 hours at room temperature.

Dilution buffer+AlphaScreen® Donor beads (2 µL) was then added, and the plate was intubated on the plate shaker for an additional 1½ hours. After completion, the plate was read on Synergy-4 or Enspire plate reader, using AlphaScreen® pSMAD3® settings.

Representative results for inhibition of GDF8 (data=GDF pSMAD (MPC11) (µM)) and TGF-β (data=TGF-β pSMAD (MPC-11) (µM)) signaling are shown in Table 1:

| No. | GDF8 | TGF-β |
|---|---|---|
| 1 | 0.0472 | 0.5596 |
| 2 | 0.1436 | 0.3176 |
| 3 | 0.3822 | 1.534 |
| 4 | 0.1709 | 0.8395 |
| 5 | 0.0661 | 0.7507 |
| 6 | 0.2637 | 1.683 |
| 7 | 0.1191 | 0.8735 |
| 8 | 0.0842 | 0.7467 |
| 9 | 0.3361 | 1.459 |
| 10 | 0.6445 | 5.131 |
| 11 | 0.9174 | 5.329 |
| 12 | 0.4813 | 1.59 |
| 13 | 0.8827 | 2.72 |
| 14 | 0.3056 | 0.7316 |
| 15 | 0.6849 | 0.8757 |
| 16 | 0.2893 | 0.41 |
| 17 | 0.2199 | 2.167 |
| 18 | 0.1541 | 1.36 |
| 19 | 0.7665 | 4.055 |
| 20 | 0.3584 | 1.744 |
| 21 | 0.2014 | 1.231 |
| 22 | 0.0321 | 0.1115 |
| 23 | 0.2568 | 1.317 |
| 24 | 0.8461 | 3.988 |
| 25 | 0.0911 | 0.326 |
| 26 | 0.1259 | 1 |
| 27 | 0.2867 | 2.203 |
| 28 | 0.3633 | 2.145 |
| 29 | 0.0215 | 0.0853 |
| 30 | 0.1933 | 0.8423 |
| 31 | 0.4631 | 2.707 |
| 32 | 0.1155 | 0.5533 |
| 33 | 0.0251 | 0.2034 |
| 34 | 0.4274 | 2.342 |
| 35 | 0.2579 | 1.996 |
| 36 | 0.5548 | 3.061 |
| 37 | 0.4594 | 3.256 |
| 38 | 0.1252 | 0.3392 |
| 39 | 0.2037 | 0.4364 |
| 40 | 0.0586 | 0.1735 |
| 41 | 0.1049 | 0.1682 |
| 42 | 0.0076 | 0.0533 |
| 43 | 0.041 | 0.1851 |
| 44 | 0.2088 | 1.843 |
| 45 | 0.6518 | 4.366 |
| 46 | 0.011 | 0.0659 |
| 47 | 0.0344 | 0.0444 |
| 48 | 0.1918 | 0.5949 |
| 49 | 0.5447 | 0.3486 |
| 50 | 1.054 | 3.491 |
| 51 | 0.7774 | 0.8289 |
| 52 | 0.2342 | 0.3216 |
| 53 | 0.5398 | 0.5433 |
| 54 | 0.4915 | 0.6624 |
| 55 | 0.2603 | 0.6288 |
| 56 | 0.1844 | 0.2807 |
| 57 | 0.8525 | 1.82 |
| 58 | 0.3937 | 0.8083 |
| 59 | 0.332 | 0.5577 |

85
-continued

| No. | GDF8 | TGF-β |
|---|---|---|
| 60 | 0.4537 | 1.04 |
| 61 | 0.2413 | 0.5354 |
| 62 | 0.3353 | 0.3811 |
| 63 | 0.3117 | 0.3954 |

What is claimed:

1. A compound having the structure of formula (IV):

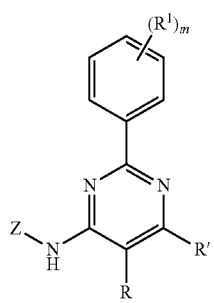
(IV)

or a pharmaceutically acceptable salt, prodrug, or N-oxide thereof, or a solvate or hydrate thereof,
wherein
Z is:
  a)

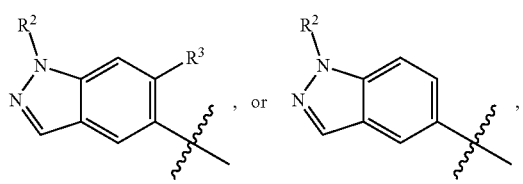

wherein
  $R^2$ is —C(O)CH$_2$NR$^b_2$,
    wherein R$^b$ is C$_{1-6}$ alkyl; and
  $R^3$ is C$_{1-6}$ alkyl; or
  b)

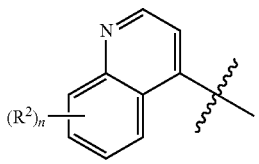

wherein
  $R^2$ is hydrogen or —OR$^b$,
    wherein R$^b$ is hydrogen or C$_{1-6}$ alkyl; and
  n is 0, 1 or 2;
R and R' are independently hydrogen or C$_{1-6}$ alkyl;
$R^1$ is halogen, cyano, or C$_{1-6}$ alkyl; and
m is 0, 1 or 2.

2. The compound of claim 1, wherein the compound has the structure

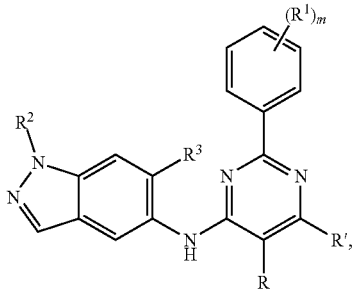
(IVa)

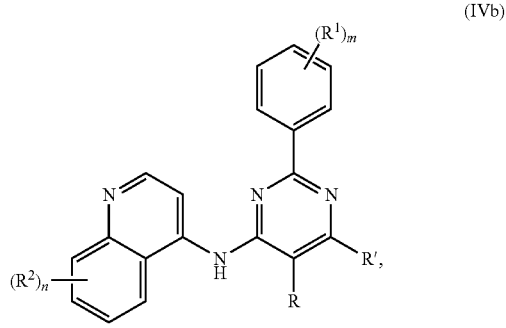
(IVb)

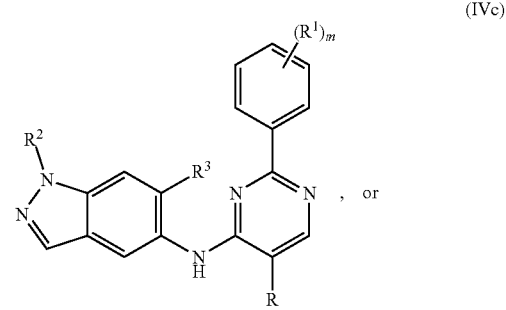
(IVc)

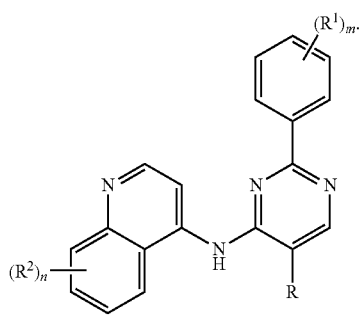
(IVd)

3. A compound having the structure of formula (II):

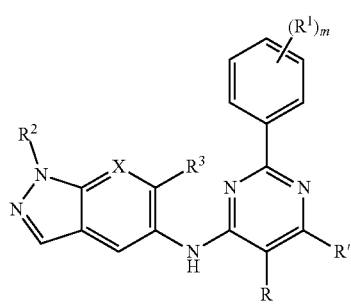

or a pharmaceutically acceptable salt, prodrug, or N-oxide thereof, or a solvate or hydrate thereof,
wherein
R and R' are independently hydrogen, halogen, $C_{1-6}$ alkyl or $C_{1-6}$ haloalkyl;
$R^1$ is halogen, cyano, —$SR^a$, —$N(R^a)_2$, $C_{1-6}$ alkyl, $C_{1-6}$haloalkyl or $C_{3-8}$cycloalkyl,
wherein each $R^a$ is independently hydrogen, $C_{1-6}$ alkyl or $C_{1-6}$ haloalkyl;
m is 0, 1, 2, 3 or 4;
X is N or C(H);
$R^2$ is hydrogen, —C(O)CH$_2$NR$^b{}_2$, —CH$_2$—OP(O)(OR$^c$)$_2$, $C_{1-6}$ alkyl, $C_{1-6}$haloalkyl, or heteroaryl,
wherein each $R^b$ is independently hydrogen or $C_{1-6}$ alkyl, and
wherein each $R^c$ is independently hydrogen or $C_{1-6}$ alkyl; and
$R^3$ is halogen, $C_{1-6}$ alkyl, $C_{1-6}$ haloalkyl, cycloalkyl or heteroaryl.

4. The compound of claim 3, having the structure of formula (IIa):

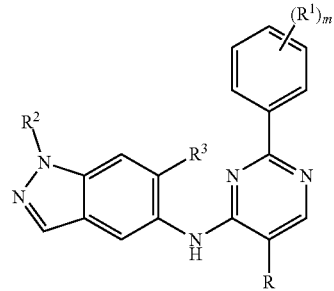

wherein
R is hydrogen, halogen, $C_{1-6}$ alkyl or $C_{1-6}$ haloalkyl;
$R^1$ is halogen, cyano, $C_{1-6}$ alkyl, —NH$_2$, $C_{1-6}$ haloalkyl or $C_{3-6}$ cycloalkyl;
m is 0, 1, 2, 3 or 4;
$R^2$ is hydrogen, $C_{1-6}$ alkyl, —C(O)CH$_2$NR$^b{}_2$, —CH$_2$OP(O)(OR$^c$)$_2$, $C_{1-6}$ haloalkyl, or $C_{5-6}$ heteroaryl,
wherein each $R^b$ is independently hydrogen or $C_{1-6}$ alkyl, and
wherein each $R^c$ is independently hydrogen or $C_{1-6}$ alkyl; and
$R^3$ is halogen, $C_{1-6}$ alkyl or $C_{1-6}$ haloalkyl.

5. The compound of claim 4, wherein
R is hydrogen, halogen, $C_{1-6}$ alkyl or $C_{1-6}$ haloalkyl;
$R^1$ is halogen, cyano, $C_{1-6}$ alkyl or —NH$_2$,
wherein $R^a$ is $C_{1-6}$ alkyl;
m is 0, 1, 2, 3 or 4;
$R^2$ is hydrogen, $C_{1-6}$ alkyl, —C(O)CH$_2$NR$^b{}_2$, or —CH$_2$OP(O)(OR$^c$)$_2$,
wherein each $R^b$ is independently hydrogen or $C_{1-6}$ alkyl, and
wherein each $R^c$ is independently hydrogen or $C_{1-6}$ alkyl; and
$R^3$ is halogen or $C_{1-6}$ alkyl.

6. The compound of claim 3, wherein the compound has the structure

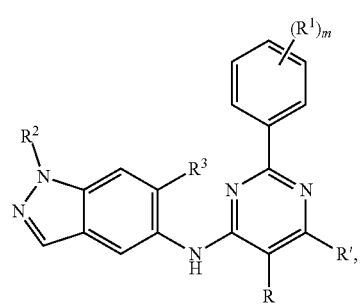

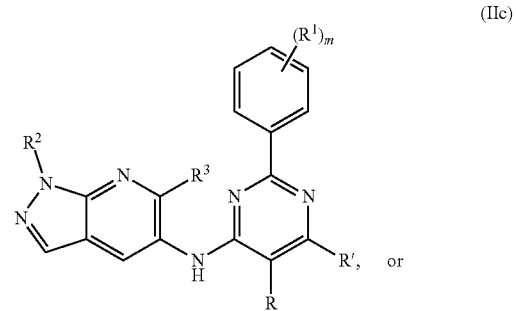

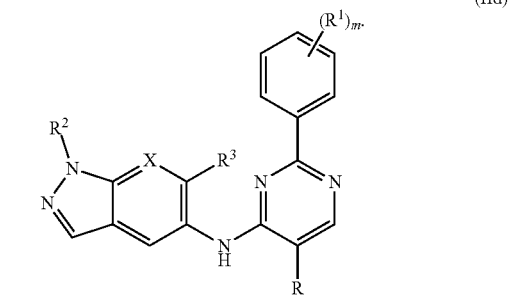

7. A compound selected from:
2-(Dimethylamino)-1-(5-((2-(2,5-dimethylphenyl)pyrimidin-4-yl)amino)-1H-indazol-1-yl)ethan-1-one;
N-(2-(3,4-Difluorophenyl)pyrimidin-4-yl)-1H-pyrazolo[3,4-b]pyridin-5-amine;
N-(2-(4-Fluorophenyl)pyrimidin-4-yl)-1H-pyrazolo[3,4-b]pyridin-5-amine;
N-(5-Fluoro-2-(4-fluoro-2-methylphenyl)pyrimidin-4-yl)-1H-pyrazolo[3,4-b]pyridin-5-amine;
N-(2-(3-Fluorophenyl)-5-methylpyrimidin-4-yl)-1H-pyrazolo[3,4-b]pyridin-5-amine;
N-(2-(4-Fluorophenyl)-5-methylpyrimidin-4-yl)-1H-pyrazolo[3,4-b]pyridin-5-amine;

N-(2-(3,4-Difluorophenyl)-5-methylpyrimidin-4-yl)-1H-pyrazolo[3,4-b]pyridin-5-amine;
N-(2-(3-Methylphenyl)-5-methylpyrimidin-4-yl)-1H-pyrazolo[3,4-b]pyridin-5-amine;
N-(2-(2-Fluorophenyl)pyrimidin-4-yl)-1H-indazol-5-amine;
N-(2-(3-Fluorophenyl)pyrimidin-4-yl)-1H-indazol-5-amine;
N-(2-Phenylpyrimidin-4-yl)-1H-indazol-5-amine;
N-(2-(2-Methylphenyl)pyrimidin-4-yl)-1H-indazol-5-amine;
6-Fluoro-N-(2-(2-fluorophenyl)pyrimidin-4-yl)-1H-indazol-5-amine;
N-(5-Fluoro-2-(2-fluorophenyl)pyrimidin-4-yl)-1H-indazol-5-amine;
N-(2-(5-fluoro-2-methylphenyl)pyrimidin-4-yl)-1H-indazol-5-amine;
N-(2-(3,5-Difluorophenyl)pyrimidin-4-yl)-1H-indazol-5-amine;
N-(2-(3-Fluoro-4-methoxyphenyl)pyrimidin-4-yl)-1H-indazol-5-amine;
N-(2-(3-Cyanophenyl)pyrimidin-4-yl)-1H-indazol-5-amine;
N-(2-(2,5-Dimethylphenyl)pyrimidin-4-yl)-1H-indazol-5-amine;
N-(2-(3-Aminophenyl)pyrimidin-4-yl)-1H-indazol-5-amine;
N-(2-(3-Methylphenyl)pyrimidin-4-yl)-1H-indazol-5-amine;
N-(2-(4-Fluorophenyl)pyrimidin-4-yl)-1H-indazol-5-amine;
N-(5-Fluoro-2-(methylphenyl)pyrimidin-4-yl)-1H-indazol-5-amine;
N-(2-(3,4-Difluorophenyl)-5-fluoropyrimidin-4-yl)-1H-indazol-5-amine;
N-(5-Fluoro-2-(3-fluorophenyl)pyrimidin-4-yl)-1H-indazol-5-amine;
N-(5-Fluoro-2-phenylpyrimidin-4-yl)-1H-indazol-5-amine;
N-(2-(2-Fluorophenyl)-5-methylpyrimidin-4-yl)-1H-indazol-5-amine;
N-(2-(2-Methylphenyl)-5-methylpyrimidin-4-yl)-1H-indazol-5-amine;
N-(2-(3,4-Difluorophenyl)-5-methylpyrimidin-4-yl)-1H-indazol-5-amine;
N-(2-(2,5-Dimethylphenyl)-5-methylpyrimidin-4-yl)-1H-indazol-5-amine;
N-(2-(4-Fluoro-2-methylphenyl)pyrimidin-4-yl)-1H-indazol-5-amine;
N-(2-(4-Fluoro-3-methylphenyl)pyrimidin-4-yl)-1H-indazol-5-amine;
N-(2-(2-Aminophenyl)pyrimidin-4-yl)-1H-indazol-5-amine;
N-(2-(3-Trifluoromethylphenyl)pyrimidin-4-yl)-1H-indazol-5-amine;
N-(2-(4-Methoxy-2-methylphenyl)pyrimidin-4-yl)-1H-indazol-5-amine;
N-(2-(4-Fluoro-2-methylphenyl)pyrimidin-4-yl)-6,7-dimethoxyquinolin-4-amine;
N-(2-(2-Fluoro-5-methylphenyl)pyrimidin-4-yl)-1H-indazol-5-amine;
N-(2-(4-Fluoro-3-methylphenyl)-5-methylpyrimidin-4-yl)-1H-pyrazolo[3,4-b]pyridin-5-amine;
N-(2-(4-Fluoro-3-methylphenyl)-5-methylpyrimidin-4-yl)-6-methyl-1H-indazol-5-amine;
N-(2-(3-Methylphenyl)-5-methylpyrimidin-4-yl)-6-methyl-1H-indazol-5-amine;
N-(2-(4-Fluorophenyl)-5-methylpyrimidin-4-yl)-6-methyl-1H-indazol-5-amine;
N-(2-(3,4-Difluorophenyl)-5-methylpyrimidin-4-yl)-6-methyl-1H-indazol-5-amine;
N-(2-(2,5-Dimethylphenyl)-5-methylpyrimidin-4-yl)-6-methyl-1H-indazol-5-amine;
N-(2-(4-Fluoro-3-methylphenyl)-5-methylpyrimidin-4-yl)-6-methyl-1H-indazol-5-amine;
6-Fluoro-N-(2-(3-fluorophenyl)-5-methylpyrimidin-4-yl)-1H-indazol-5-amine;
6-Fluoro-N-(2-(3-methylphenyl)-5-methylpyrimidin-4-yl)-1H-indazol-5-amine;
6-Fluoro-N-(2-(2,5-dimethylphenyl)-5-methylpyrimidin-4-yl)-1H-indazol-5-amine;
6-Fluoro-N-(2-(3,4-difluorophenyl)-5-methylpyrimidin-4-yl)-1H-indazol-5-amine;
6-Fluoro-N-(2-(4-fluoro-3-methylphenyl)-5-methylpyrimidin-4-yl)-1H-indazol-5-amine;
N-(2-(2-Fluorophenyl)-5-methylpyrimidin-4-yl)-6-methoxy-1H-indazol-5-amine;
N-(2-(3,4-Difluorophenyl)-5-methylpyrimidin-4-yl)-6-methoxy-1H-indazol-5-amine;
or a pharmaceutically acceptable salt, prodrug, or N-oxide thereof, or a solvate or hydrate thereof.

8. A pharmaceutical composition comprising a pharmaceutically acceptable diluent, carrier, or excipient and a compound according to claim 3.

* * * * *